United States Patent
Desai et al.

(10) Patent No.: US 10,682,420 B2
(45) Date of Patent: *Jun. 16, 2020

(54) BREAST CANCER THERAPY BASED ON HORMONE RECEPTOR STATUS WITH NANOPARTICLES COMPRISING TAXANE

(71) Applicant: Abraxis BioScience, LLC, Los Angeles, CA (US)

(72) Inventors: Neil P. Desai, Pacific Palisades, CA (US); Patrick Soon-Shiong, Los Angeles, CA (US)

(73) Assignee: Abraxis BioScience, LLC, Summit, NJ (US)

( * ) Notice: Subject to any disclaimer, the term of this patent is extended or adjusted under 35 U.S.C. 154(b) by 194 days.

This patent is subject to a terminal disclaimer.

(21) Appl. No.: 15/593,155

(22) Filed: May 11, 2017

(65) Prior Publication Data

US 2017/0340599 A1 Nov. 30, 2017

Related U.S. Application Data

(63) Continuation of application No. 12/519,126, filed as application No. PCT/US2007/025645 on Dec. 14, 2007, now Pat. No. 9,675,578.

(60) Provisional application No. 60/875,004, filed on Dec. 14, 2006.

(51) Int. Cl.
| | | |
|---|---|---|
| *A61K 38/38* | (2006.01) | |
| *A61K 47/64* | (2017.01) | |
| *A61K 31/704* | (2006.01) | |
| *A61K 31/7068* | (2006.01) | |
| *A61K 39/395* | (2006.01) | |
| *A61K 31/282* | (2006.01) | |
| *A61K 31/475* | (2006.01) | |
| *A61K 31/5377* | (2006.01) | |
| *A61K 31/513* | (2006.01) | |
| *A61K 31/664* | (2006.01) | |
| *A61K 9/00* | (2006.01) | |
| *A61K 9/51* | (2006.01) | |
| *A61K 47/42* | (2017.01) | |
| *A61P 35/00* | (2006.01) | |
| *A61K 31/337* | (2006.01) | |
| *A61K 31/505* | (2006.01) | |
| *A61K 31/661* | (2006.01) | |
| *A61K 31/7034* | (2006.01) | |

(52) U.S. Cl.
CPC .......... *A61K 47/643* (2017.08); *A61K 9/0019* (2013.01); *A61K 9/5169* (2013.01); *A61K 31/282* (2013.01); *A61K 31/337* (2013.01); *A61K 31/475* (2013.01); *A61K 31/505* (2013.01); *A61K 31/513* (2013.01); *A61K 31/5377* (2013.01); *A61K 31/661* (2013.01); *A61K 31/664* (2013.01); *A61K 31/704* (2013.01); *A61K 31/7034* (2013.01); *A61K 31/7068* (2013.01); *A61K 39/39558* (2013.01); *A61K 47/42* (2013.01); *A61K 47/64* (2017.08); *A61P 35/00* (2018.01)

(58) Field of Classification Search
None
See application file for complete search history.

(56) References Cited

U.S. PATENT DOCUMENTS

| | | |
|---|---|---|
| 5,362,478 A | 11/1994 | Desai et al. |
| 5,439,686 A | 8/1995 | Desai et al. |
| 5,470,571 A | 11/1995 | Herlyn et al. |
| 5,498,421 A | 3/1996 | Grinstaff et al. |
| 5,505,932 A | 4/1996 | Grinstaff et al. |
| 5,508,021 A | 4/1996 | Grinstaff et al. |
| 5,512,268 A | 4/1996 | Grinstaff et al. |
| 5,558,864 A | 9/1996 | Bendig et al. |
| 5,560,933 A | 10/1996 | Soon-Shiong et al. |
| 5,635,207 A | 6/1997 | Grinstaff et al. |
| 5,639,473 A | 6/1997 | Grinstaff et al. |
| 5,650,156 A | 7/1997 | Grinstaff et al. |
| 5,665,382 A | 9/1997 | Grinstaff et al. |
| 5,665,383 A | 9/1997 | Grinstaff et al. |
| 5,690,928 A | 11/1997 | Heimbrook et al. |
| 5,859,018 A | 1/1999 | Brown et al. |
| 5,916,596 A | 6/1999 | Desai et al. |
| 5,997,904 A | 12/1999 | Magdassi et al. |
| 6,096,331 A | 8/2000 | Desai et al. |

(Continued)

FOREIGN PATENT DOCUMENTS

| | | |
|---|---|---|
| WO | WO-94/18954 A1 | 9/1994 |
| WO | WO-98/14174 A1 | 4/1998 |

(Continued)

OTHER PUBLICATIONS

US 8,968,752 B2, 03/2015, Desai et al. (withdrawn)
Bryan, B.B. et al. (2006, e-pub. Mar. 10, 2006). "Ductal Carcinoma In Situ With Basal-Like Phenotype: A Possible Precursor to Invasive Basal-Like Breast Cancer," Modern Pathology 19:617-621.
Extended European Search Report and Search Opinion dated Mar. 20, 2019, for European Patent Application No. 18190377.4, 9 pages.
Final Office Action dated May 31, 2018, for U.S. Appl. No. 15/183,636, filed Jun. 15, 2016, 37 pages.

(Continued)

*Primary Examiner* — Michael D Pak
(74) *Attorney, Agent, or Firm* — Morrison & Foerster LLP

(57) ABSTRACT

The present invention relates to methods and kits for the treatment of breast cancer based on hormone receptor status of progesterone receptor and estrogen receptor comprising the administration of a taxane alone, in combination with at least one other and other therapeutic agents, as well as other treatment modalities useful in the treatment of breast cancer. In particular, the invention relates to the use of nanoparticles comprising paclitaxel and albumin (such as Abraxane®) either alone or in combination with other chemotherapeutic agents or radiation, which may be used for the treatment of breast cancer which does not express estrogen receptor and/or progesterone receptor.

19 Claims, 11 Drawing Sheets

(56) References Cited

U.S. PATENT DOCUMENTS

| | | |
|---|---|---|
| 6,506,405 B1 | 1/2003 | Desai et al. |
| 6,528,067 B1 | 3/2003 | Magdassi et al. |
| 6,537,579 B1 | 3/2003 | Desai et al. |
| 6,565,842 B1 | 5/2003 | Desai et al. |
| 6,566,405 B2 | 5/2003 | Weidner et al. |
| 6,652,884 B2 | 11/2003 | Falciani |
| 6,749,868 B1 | 6/2004 | Desai et al. |
| 6,753,006 B1 | 6/2004 | Desai et al. |
| 7,758,891 B2 | 7/2010 | Desai et al. |
| 7,771,751 B2 | 8/2010 | Desai et al. |
| 7,780,984 B2 | 8/2010 | Desai et al. |
| 7,820,788 B2 | 10/2010 | Desai et al. |
| 7,923,536 B2 | 4/2011 | Desai et al. |
| 7,981,445 B2 | 7/2011 | De et al. |
| 8,034,375 B2 | 10/2011 | Desai et al. |
| 8,034,765 B2 | 10/2011 | De et al. |
| 8,137,684 B2 | 3/2012 | Desai et al. |
| 8,138,229 B2 | 3/2012 | Desai et al. |
| 8,257,733 B2 | 9/2012 | Desai et al. |
| 8,268,348 B2 | 9/2012 | Trieu et al. |
| 8,314,156 B2 | 11/2012 | Desai et al. |
| 8,735,394 B2 | 5/2014 | Desai et al. |
| 8,846,771 B2 | 9/2014 | Desai et al. |
| 8,853,260 B2 | 10/2014 | Desai et al. |
| 8,911,786 B2 | 12/2014 | Desai et al. |
| 8,927,019 B2 | 1/2015 | Desai et al. |
| 8,999,396 B2 | 4/2015 | Desai et al. |
| 9,012,518 B2 | 4/2015 | Desai et al. |
| 9,012,519 B2 | 4/2015 | Desai et al. |
| 9,061,014 B2 | 6/2015 | Seward et al. |
| 9,101,543 B2 | 8/2015 | Desai et al. |
| 9,149,455 B2 | 10/2015 | Desai et al. |
| 9,308,180 B2 | 4/2016 | De et al. |
| 9,370,494 B2 | 6/2016 | Yeo et al. |
| 9,393,318 B2 | 7/2016 | Desai et al. |
| 9,399,071 B2 | 7/2016 | Desai et al. |
| 9,399,072 B2 | 7/2016 | Desai et al. |
| 9,446,003 B2 | 9/2016 | Desai et al. |
| 9,511,046 B2 | 12/2016 | Desai et al. |
| 9,561,288 B2 | 2/2017 | Desai et al. |
| 9,585,960 B2 | 3/2017 | Foss et al. |
| 9,597,409 B2 | 3/2017 | Desai et al. |
| 9,675,578 B2 | 6/2017 | Desai et al. |
| 9,724,232 B2 | 8/2017 | Desai et al. |
| 9,820,949 B2 | 11/2017 | Desai et al. |
| 9,855,220 B2 | 1/2018 | Desai et al. |
| 9,884,013 B2 | 2/2018 | Seward et al. |
| 9,962,373 B2 | 5/2018 | Desai et al. |
| 10,076,501 B2 | 9/2018 | Foss et al. |
| 10,258,565 B2 | 4/2019 | Seward |
| 10,328,031 B2 | 6/2019 | Desai |
| 10,413,531 B2 | 9/2019 | Desai |
| 2003/0199425 A1 | 10/2003 | Desai et al. |
| 2004/0143004 A1 | 7/2004 | Fargnoli et al. |
| 2005/0004002 A1 | 1/2005 | Desai et al. |
| 2006/0003931 A1 | 1/2006 | Eigenbrot, Jr. et al. |
| 2006/0013819 A1 | 1/2006 | Kelsey |
| 2007/0087022 A1 | 4/2007 | Desai et al. |
| 2007/0093547 A1 | 4/2007 | Desai et al. |
| 2007/0116774 A1 | 5/2007 | Desai et al. |
| 2007/0129448 A1 | 6/2007 | Desai et al. |
| 2007/0166388 A1 | 7/2007 | Desai et al. |
| 2008/0213370 A1 | 9/2008 | Desai et al. |
| 2008/0280987 A1 | 11/2008 | Desai et al. |
| 2009/0258096 A1 | 10/2009 | Cohen |
| 2009/0263483 A1 | 10/2009 | Desai et al. |
| 2009/0304805 A1 | 12/2009 | Desai et al. |
| 2010/0035800 A1 | 2/2010 | Desai et al. |
| 2010/0048499 A1 | 2/2010 | Desai et al. |
| 2010/0112077 A1 | 5/2010 | Desai et al. |
| 2010/0166869 A1 | 7/2010 | Desai et al. |
| 2010/0183728 A1 | 7/2010 | Desai et al. |
| 2010/0215751 A1 | 8/2010 | Desai et al. |
| 2010/0297243 A1 | 11/2010 | Desai et al. |
| 2011/0052708 A1 | 3/2011 | Soon-Shiong et al. |
| 2011/0118342 A1 | 5/2011 | De et al. |
| 2011/0151012 A1 | 6/2011 | Desai et al. |
| 2011/0165256 A1 | 7/2011 | Desai et al. |
| 2011/0196026 A1 | 8/2011 | De et al. |
| 2011/0301248 A1 | 12/2011 | Desai et al. |
| 2012/0070502 A1 | 3/2012 | Desai et al. |
| 2012/0076862 A1 | 3/2012 | Desai et al. |
| 2012/0128732 A1 | 5/2012 | Trieu et al. |
| 2012/0189701 A1 | 7/2012 | Desai et al. |
| 2012/0231082 A1 | 9/2012 | Desai et al. |
| 2012/0283205 A1 | 11/2012 | Desai et al. |
| 2012/0308612 A1 | 12/2012 | De et al. |
| 2013/0045240 A1 | 2/2013 | Tao et al. |
| 2013/0071438 A1 | 3/2013 | Desai et al. |
| 2013/0115296 A1 | 5/2013 | Yeo et al. |
| 2013/0195922 A1 | 8/2013 | Desai et al. |
| 2013/0195983 A1 | 8/2013 | Desai et al. |
| 2013/0195984 A1 | 8/2013 | Desai et al. |
| 2013/0202709 A1 | 8/2013 | Desai et al. |
| 2013/0209518 A1 | 8/2013 | Desai et al. |
| 2013/0244952 A1 | 9/2013 | Desai et al. |
| 2013/0266659 A1 | 10/2013 | Desai et al. |
| 2013/0280336 A1 | 10/2013 | Desai et al. |
| 2013/0280337 A1 | 10/2013 | Desai et al. |
| 2014/0017315 A1 | 1/2014 | Desai et al. |
| 2014/0017316 A1 | 1/2014 | Desai et al. |
| 2014/0017323 A1 | 1/2014 | Desai et al. |
| 2014/0023717 A1 | 1/2014 | Desai et al. |
| 2014/0039069 A1 | 2/2014 | Desai et al. |
| 2014/0039070 A1 | 2/2014 | Desai et al. |
| 2014/0056986 A1 | 2/2014 | Desai et al. |
| 2014/0072630 A1 | 3/2014 | Tao et al. |
| 2014/0072631 A1 | 3/2014 | Trieu et al. |
| 2014/0072643 A1 | 3/2014 | Desai et al. |
| 2014/0079787 A1 | 3/2014 | Yeo et al. |
| 2014/0079788 A1 | 3/2014 | Desai et al. |
| 2014/0079793 A1 | 3/2014 | Desai et al. |
| 2014/0080901 A1 | 3/2014 | Desai et al. |
| 2014/0134257 A1 | 5/2014 | Desai et al. |
| 2014/0155344 A1 | 6/2014 | Desai et al. |
| 2014/0170228 A1 | 6/2014 | Desai et al. |
| 2014/0186447 A1 | 7/2014 | Desai |
| 2014/0199403 A1 | 7/2014 | Desai et al. |
| 2014/0199404 A1 | 7/2014 | Heise et al. |
| 2014/0199405 A1 | 7/2014 | Pierce et al. |
| 2014/0271871 A1 | 9/2014 | Desai et al. |
| 2014/0296279 A1 | 10/2014 | Seward et al. |
| 2014/0296353 A1 | 10/2014 | Desai et al. |
| 2014/0302157 A1 | 10/2014 | Desai et al. |
| 2015/0050356 A1 | 2/2015 | Desai et al. |
| 2015/0079177 A1 | 3/2015 | Desai et al. |
| 2015/0079181 A1 | 3/2015 | Desai et al. |
| 2015/0104521 A1 | 4/2015 | Desai et al. |
| 2015/0111960 A1 | 4/2015 | Desai et al. |
| 2015/0157722 A1 | 6/2015 | Foss et al. |
| 2015/0165047 A1 | 6/2015 | Desai et al. |
| 2015/0190519 A1 | 7/2015 | Desai et al. |
| 2015/0313866 A1 | 11/2015 | Desai et al. |
| 2016/0008330 A1 | 1/2016 | Desai et al. |
| 2016/0015681 A1 | 1/2016 | Desai et al. |
| 2016/0015817 A1 | 1/2016 | Benettaib et al. |
| 2016/0151325 A1 | 6/2016 | Desai et al. |
| 2016/0228401 A1 | 8/2016 | Desai et al. |
| 2016/0374952 A1 | 12/2016 | Yeo et al. |
| 2017/0014373 A1 | 1/2017 | Desai et al. |
| 2017/0020824 A1 | 1/2017 | Desai et al. |
| 2017/0049711 A1 | 2/2017 | Desai et al. |
| 2017/0100344 A1 | 4/2017 | Desai et al. |
| 2017/0105951 A1 | 4/2017 | Desai et al. |
| 2017/0157035 A1 | 6/2017 | Seward et al. |
| 2017/0172975 A1 | 6/2017 | Desai et al. |
| 2017/0181988 A1 | 6/2017 | Desai et al. |
| 2017/0202782 A1 | 7/2017 | Pierce et al. |
| 2017/0224627 A1 | 8/2017 | Foss et al. |
| 2017/0333384 A1 | 11/2017 | Desai et al. |
| 2017/0340599 A1 | 11/2017 | Desai et al. |
| 2018/0015181 A1 | 1/2018 | Desai et al. |
| 2018/0064679 A1 | 3/2018 | Pierce et al. |
| 2018/0133157 A1 | 5/2018 | Desai et al. |

(56) References Cited

U.S. PATENT DOCUMENTS

| | | |
|---|---|---|
| 2018/0147139 A1 | 5/2018 | Seward et al. |
| 2018/0153820 A1 | 6/2018 | Desai et al. |
| 2018/0153863 A1 | 6/2018 | Desai |
| 2018/0169017 A1 | 6/2018 | Desai et al. |
| 2018/0177770 A1 | 6/2018 | Desai |
| 2018/0177771 A1 | 6/2018 | Desai |
| 2018/0214425 A1 | 8/2018 | Desai |
| 2018/0256551 A1 | 9/2018 | Desai et al. |
| 2018/0289620 A1 | 10/2018 | Desai et al. |
| 2018/0374583 A1 | 12/2018 | Goldstein et al. |
| 2019/0022020 A1 | 1/2019 | Desai et al. |
| 2019/0054033 A1 | 2/2019 | Foss et al. |
| 2019/0147986 A1 | 5/2019 | Luo |
| 2019/0167629 A1 | 6/2019 | Desai |
| 2019/0175564 A1 | 6/2019 | Desai |
| 2019/0183789 A1 | 6/2019 | Seward |
| 2019/0184031 A1 | 6/2019 | Desai |
| 2019/0192477 A1 | 6/2019 | Desai |
| 2019/0247357 A1 | 8/2019 | Foss |
| 2019/0307732 A1 | 10/2019 | Desai |

FOREIGN PATENT DOCUMENTS

| | | |
|---|---|---|
| WO | WO-98/14175 A1 | 4/1998 |
| WO | WO-99/00113 A1 | 1/1999 |
| WO | WO-00/64437 A1 | 11/2000 |
| WO | WO-00/71079 A2 | 11/2000 |
| WO | WO-00/71079 A3 | 11/2000 |
| WO | WO-01/89522 A1 | 11/2001 |
| WO | WO-02/087545 A1 | 11/2002 |
| WO | WO-03/096944 A1 | 11/2003 |
| WO | WO-2004/052401 A2 | 6/2004 |
| WO | WO-2004/052401 A3 | 6/2004 |
| WO | WO-2005/000900 A1 | 1/2005 |
| WO | WO-2005/117978 A2 | 12/2005 |
| WO | WO-2005/117978 A3 | 12/2005 |
| WO | WO-2005/117986 A2 | 12/2005 |
| WO | WO-2005/117986 A3 | 12/2005 |
| WO | WO-2006/089290 A1 | 8/2006 |
| WO | WO-2007/027819 A2 | 3/2007 |
| WO | WO-2007/027819 A3 | 3/2007 |
| WO | WO-2007/027941 A2 | 3/2007 |
| WO | WO-2007/027941 A3 | 3/2007 |
| WO | WO-2008/027055 A1 | 3/2008 |
| WO | WO-2008/057562 A1 | 5/2008 |
| WO | WO-2008/076373 A1 | 6/2008 |

OTHER PUBLICATIONS

U.S. Appl. No. 15/796,578, filed Oct. 27, 2017, for Desai et al. (U.S. Patent Application is not submitted herewith pursuant to the waiver of 37 C.F.R. § 1.98(a)(2)(iii) issued by the Office on Sep. 21, 2004.).

U.S. Appl. No. 16/101,027, filed Aug. 10, 2018, for Desai et al. (U.S. Patent Application is not submitted herewith pursuant to the waiver of 37 C.F.R. § 1.98(a)(2)(iii) issued by the Office on Sep. 21, 2004.).

U.S. Appl. No. 16/107,419, filed Aug. 21, 2018, for Foss et al. (U.S. Patent Application is not submitted herewith pursuant to the waiver of 37 C.F.R. § 1.98(a)(2)(iii) issued by the Office on Sep. 21, 2004.).

U.S. Appl. No. 16/170,522, filed Oct. 25, 2018, for Desai et al. (U.S. Patent Application is not submitted herewith pursuant to the waiver of 37 C.F.R. § 1.98(a)(2)(iii) issued by the Office on Sep. 21, 2004.).

U.S. Appl. No. 16/284,995, filed Feb. 25, 2019, for Desai et al. (U.S. Patent Application is not submitted herewith pursuant to the waiver of 37 C.F.R. § 1.98(a)(2)(iii) issued by the Office on Sep. 21, 2004.).

U.S. Appl. No. 16/274,632, filed Feb. 13, 2019, for Desai et al.(U.S. Patent Application is not submitted herewith pursuant to the waiver of 37 C.F.R. § 1.98(a)(2)(iii) issued by the Office on Sep. 21, 2004.).

Untch, M. et al. (Mar. 2016, e-pub. Feb. 8, 2016). "Nab-Paclitaxel Versus Solvent-Based Paclitaxel in Neoadjuvant Chemotherapy for Early Breast Cancer (GeparSepto—GBG 69): A Randomised, Phase 3 Trial," The Lancet Oncology 17(3):345-356, 12 pages.

Altundag, K. et al. (Apr. 1, 2007). "Potential Chemotherapy Options in the Triple Negative Subtype of Breast Cancer," *J. Clin. Oncol.* 25(10):1294-1295.

American Cancer Society. (Sep. 2006). "Breast Cancer Treatment Guidelines for Patients", Publication from the American Cancer Society and National Comprehensive Cancer Network, Version VIII, located at < http://screening.iarc.fr/doc/Breast_VIII.pdf> 92 pages.

Berry, D.A. et al. (Apr. 12, 2006). "Estrogen-Receptor Status and Outcomes of Modern Chemotherapy for Patients with Node-Positive Breast Cancer," *Journal of the American Medical Association* 295(14):1658-1667.

Bertolini, F. et al. (Aug. 1, 2003). "Maximum Tolerable Dose and Low-Dose Metronomic Chemotherapy Have Opposite Effects on the Mobilization and Viability of Circulating Endothelial Progenitor Cells," *Cancer Res.* 63(15):4342-4346.

Blum, J. L. et al. (Jul. 15, 2004). "Long Term Diseases Control in Taxane-Refractor Metastatic Breast Cancer Treated with nab Paclitaxel," *Pro. Am. Soc. Clin. Oncol.*, 2004 ASCO Annual Meeting Proceedings, 40$^{th}$ Annual Meeting, Jun. 5-8, 2004, New Orleans, 22(14 Suppl.), p. 13S, Abstract 543.

Bocci, G. et al. (Dec. 1, 2002). "Protracted Low-Dose Effects on Human Endothelial Cell Proliferation and Survival in Vitro reveal a Selective Antiangiogenic Window for Various Chemotherapeutic Drugs," *Cancer Res.* 62:6938-6943.

Bocci, G. et al. (Oct. 28, 2003). "Thrombospondin 1, a Mediator of the Antiangiogenic Effects of Low-dose Metronomic Chemotherapy," *Proc. Nat. Acad. Sci. USA* 100(22):12917-12922.

Business Wire (Dec. 6, 2005), "NCCN Announces Two New Breast Cancer Resources," Article located at http:www.nccn.org/about/news/newsinfo.asp?NewsIDS=60, last visited on Apr. 14, 2011, one page.

Buzdar, A. U. et al. (2003). "Pathological Complete Response to Chemotherapy is Related to Hormone Receptor Status," *Breast Cancer Research and Treatment* 82(Suppl. 1):S69, Abstract No. 302.

Carmeliet, P. et al. (Sep. 14, 2000). "Angiogenesis in Cancer and Other Diseases," *Nature* 407(6801):249-257.

Chan, A. C. et al. (Jun. 1996). "Regulation of Antigen Receptor Signal Transduction by Protein Tyrosine Kinases," *Curr. Opin. Immunol.* 8(3):394-401.

Charfare, H. et al. (2005). "Neoadjuvant Chemotherapy in Breast Cancer," *British Journal of Surgery* 92:14-23.

Chia, K. et al. (Sep. 1, 2007). "Triple-Negative Breast Cancer: An Update," *Advances in Breast Cancer* 4(3):75-80.

Colleoni, M. et al. (Aug. 2000). "Response to Primary Chemotherapy in Breast Cancer Patients With Tumors not Expressing Estrogen and Progesterone," *Annals of Oncology* 11(8):1057-1059.

Cooper, J. A. (Dec. 1994). "Membrane-Associated Tyrosine Kinases as Molecular Switches," *Semin.Cell Biol.* 5(6):377-387.

Courtneidge, S. A. et al. (1993). "The Src Family of Protein Tyrosine Kinases: Regulation and Functions," *Dev. Suppl.* pp. 57-64.

Desai, N. et al. (Dec. 2003). "Evidence of Greater Antitumor Activity and Red Cell Partitioning and Superior Antitumor Activity of Cremophor Free Nanoparticle Paclitaxel (ABI-007) Compared to Taxol," *Breast Cancer Research and Treatment, 26$^{th}$Annual San Antonio Breast Cancer Symposium (SABCS),* San Antonio, Texas, 82(Supp. 1): Abstract No. 348, pp. S82-S83.

Desai, N. et al. (Sep. 2004). "Increased Transport of Nanoparticle Albumin-Bound Paclitaxel (ABI-007) by Endothelial gp60-Mediated Caveolar Transcystosis: A Pathway Inhibited by Taxol," *16$^{th}$EORTC-NCI-AACR, European Journal of Ccancer Supplements, Symposium on Molecular Targets and Cancer Therapeutics, 2004 Annual Meeting of the American Association for Cancer Research* (AACR) 2(8): p. 182, Abstract No. 601.

Elferink, Oude, R.F.M. et al. (Feb. 1991). "Short-term in Vitro drug testing of mamma tumors: Relation to estrogen and progesterone receptor levels, age, and proliferation rate," *Journal of Surgical Research* 50(2):135-138.

Estevez, L. G. et al. (Aug. 2007). "Evidence-Based Use of Taxanes in the Adjuvant Setting of Breast Cancer. A Review of Randomized Phase III Trials," *Cancer Treatment Reviews,* 33(5):474-483.

(56) References Cited

OTHER PUBLICATIONS

Folkman, J. (Feb. 1986). "How is Blood Vessel Growth Regulated in Normal and Neoplastic Tissue? G. H. A. Clowes Memorial Award Lecture," *Cancer Res.* 46(2):467-473.
Folkman, J. (Jan. 3, 1990). "What is the Evidence that Tumors Are Angiogenesis Dependent," *J. Nat. Cancer Inst.* 82(1):4-6.
Folkman, J. et al. (1995). "Tumor Angiogenesis," in Chapter 10 of *The Molecular Basis of Cancer,* Mendelsohn, J. H. et al. eds. *The Molecular Basis of Cancer,* $1^{st}$ edition, W. B. Saunders Company, publisher, Philadelphia, pp. 206-232.
Garces, C.A. et al. (Jul. 2004). "Neoadjuvant Chemotherapy of Breast Cancer" *The American Surgeon* 70(7):565-569.
Gelderblom, H. et al. (Apr. 2002). "Influence of Cremophor EL on the Bioavailability of Interperitoneal Paclitaxel," *Clin. Cancer Res.* 8(4):1237-124 1.
Georges, E. et al. (1990). "Multidrug Resistance and Chemosensitization: Therapeutic Implications for Cancer Chemotherapy," *Adv. in Pharmacology* 21:185-220.
Gianni, L. et al. (2002). "First Report of the European Cooperative Trial in Operable Breast Cancer (ECTO) Effects of Primary Systemic Therapy (PST) on Local-Regional Disease," *Proceeding of ASCO* 21, (abstract 132).
Gradishar, W. J. et al. (Nov. 1, 2005). "Phase III Trial of Nanoparticle Albumin-Bound Paclitaxel Compared with Polyethylated Castor Oil-Based Paclitaxel in Women With Breast Cancer," *J. Clin. Oncol.* 23(31):7794-7803.
Grant, D. S. et al. (Mar. 10, 2003). "Comparison of AntiAngiogenic Activities Using Paclitaxel (Taxol) and Docetaxel (Taxotere)," *Int. J. Cancer* 104(1):121-129.
Heinemann, V. (Jul. 1, 2006). "Systemische Chemotherapie Beim Metastasierten Mammakarzinom," *Onkologe* 12(7):683-698 and English Abstract.
Henderson, B. E. et al. (Jan. 15, 1988). "Estrogens as a Cause of Human Cancer: The Richard and Hinda Rosenthal Foundation Award Lecture," *Cancer Res.* 48(2):246-253.
Hudis, C.A. et al. (2011). "Triple-Negative Breast Cancer: An Unmet Medical Need," *The Oncologist* 16(Supp. 1):1-11.
Jaulin-Bastard, F. et al. (May 4, 2001, e-pub. Feb. 5, 2001). "The ERBB2/HER2 Receptor Differentially Interacts with ERBIN and PICK1 PSD-95/DLG/ZO-1 Domain Proteins," *The Journal of Biological Chemistry* 276(18):15256-15263.
Jimenez, J. et al. (Jan. 15, 1992). "Protection from 1-β-D-Arabinofuranosylcytosine-Induced Alopecia by Epidermal Growth Factor and Fibroblast Growth Factor in the Rat Model," *Cancer Research* 52(2):413-415.
Johnston, S.R.D. et al. (Oct. 2006). *Handbook of Metastatic Breast Cancer,* Informa Healthcare, London, United Kingdom, pp. 1-232.
Kauraniemi, P. et al. (Nov. 15, 2001). "New Applified and Highly Expressed Genes Discovered in the ERBB2 Amplicon in Breast Cancer by cDNA Microarrays," *Cancer Research* 61:8235-8240.
Konecny, G. et al. (Jan. 15, 2003). "Quantitative Association Between HER-2/neu and Steroid Hormone Receptors in Hormone Receptor-Positive Primary Breast Cancer," *J. Natl. Cancer Inst.* 95(2):142-153.
Kononen, J. et al. (Jul. 1998). "Tissue Microarrays for High-Throughput Molecular Profiling of Tumor Specimens," *Nature Med.* 4(7):844-847.
Kubota, T. et al. (1995). "Growth Regulation by Estradiol, Progesterone and Recombinant Human Epidermal Growth Factor of Human Breast Carcinoma Xenografts Grown Serially in Nude Mice," *Anticancer Research* 15:1275-1278.
Kuerer, H. M. et al. (Feb. 1999). "Clinical Course of Breast Cancer Patients With Complete Pathologic Primary Tumor and Axillary Lymph Node Response to Doxorubicin-Based Neoadjuvant Chemotherapy," *J. Clin. Oncol.* 17(2):460-469.
Link, J.S. et al. (2007). "Bevacizumab and Albumin-Bound Paclitaxel Treatment in Metastatic Breast Cancer," *Clinical Breast Cancer* 7(10):779-783.
Lobo, C.F. et al. (Jun. 20, 2006). "Nanoparticle Albumin-bound (Nab) Paclitaxel (P) in Combination with Bevacizumab (B) with and Without Gemcitabine (G): Early Experience at the Braman Family Breast Cancer institute," *Journal of Clinical Oncology,* 23(185):10748, 1 page. (Abstact Only.).
Lobo, C. et al. (Oct. 2007, e-pub Sep. 12, 2007). "Paclitaxel Albumin-Bound Particles (Abraxane™) in Combination With Bevacizumab With or Without Gemcitabine: Early Experience at the University of Miami/Braman Family Breast Cancer Institute," *Biomedicine & Pharmacotherapy* 61(9):531-533.
Lorenz, W. et al. (Mar. 1977). "Histamine Release in Dogs by Cremophor E1® and its Derivatives: Oxethylated Oleic Acid is the Most Effective Constituents," *Agents Actions* 7(1):63-67.
MacGrogan, G. et al. (Nov. 1996). "Primary Chemotherarpy in Breast Invasive Carcinoma. Predicitve Value of the Immunolhisotochemical Detection of the Hormonal Receptors, p53, C-erbB-2, MIB1, pS2 and $GST_{TT}$," *Brtish Journal of Cancer* 74(9):1458-1465.
Makris, A. et al. (Apr. 1997). « Prediction of Response to Neoadjuvant Chemoenoctrine Therapy in Primary Breast Carcinomas, *Clinical Cancer Research* 3(4):593-600.
Mano, M. S. et al. (Apr. 2005). "Adjuvant Anthracycline-Based Chemotherapy for Early Breast Cancer: Do the Does and Schedule Matter?" *Cancer Treatment Reviews* 31(2):69-78.
Mamounas, E. et al. (Jun. 1, 2005). "Paclitaxel After Doxorubicin Plus Cyclophosphamide as Adjuvant Chemotherapy for Node-Positive Breast Cancer: Results From NSABP B-28," *Journal of Clinical Oncology* 23(16):3686-3696.
Mauriac, L. et al. (1999). "Neoadjuvant Chemotherapy for Operable Breast Carcinoma Larger Than 3 cm: A unicentre Radomized Trial with a 124-Month Median Follow-Up," *Annals of Oncology* 10:47-52.
Minderman, H. et al. (May 2004, e-pub. Jan. 27, 2004). "Broad-Spectrum Modulation of ATP-Binding Cassette Transport Proteins by the Taxane Derivatives Ortataxel (IDN-5109, BAY 59-8862) and tRA96023," *Cancer Chemother. Pharmacol.* 53(5):363-369.
Müller, B.G. et al. (1996). "Albumin Nanospheres as Carriers for Passive Drug Targeting: An Optimized Manufacturing Technique," *Pharmaceutical Research* 13(1):32-37.
Ng, S. S. W. et al. (Feb. 1, 2004). "Taxane-Mediated Antiangiogenesis in Vitro: Influence of Formulation Vehicles and Binding Proteins," *Cancer Res.* 64:821-824.
O'Reilly, M.S. et al. (Oct. 21, 1994). "Angiostatin: A Novel Angiogenesis Inhibitor That Mediates the Suppression of Metastases by a Lewis Lung Carcinoma," *Cell* 79(2):315-328.
O'Reilly, M.S. et al. (Jan. 24, 1997). "Endostatin: An Endogenous Inhibitor of Angiogenesis and Tumor Growth," *Cell* 88(2):277-285.
O'Shaughnessy, J. et al. (2003). "ABI-007 (ABRAXANE$^{IM}$), A Nanoparticle Albumin-Bound (nab) Paclitaxel Demonstrates Superior Efficacy vs Taxol in MBC: A Phase III Trial," *Breast Cancer Res. Treat, Proceedings of the $26^{th}$ Annual San Antonio Breast Cancer Symposium (SABCS),* San Antonio, Texas, Dec. 3-6, 2003, 82(Suppl. 1):3, Abstract No. 44, p. 182, total of three pages.
Paulson, R. F. et al. (Aug. 1995). "Receptor Tyrosine Kinase and the Regulation of Hematopoiesis," *Semin. Immunol.* 7(4):267-277.
Pike, M. C. et al. (1993). "Estrogens, Progestogens, Normal Breast Cell Proliferation, and Breast Cancer Risk," *Epidemiologic Reviews* 15(1):17-35.
Purcell, M. et al. (Mar. 16, 2000). "Interaction of Taxol with Human Serum Albumin," *Biochim. Biophys. Acta* 1478(1):61-68.
Ring, A.E. et al. (2004, e-pub. Nov. 23, 2004). "Oestrogen Receptor Status, Pathological Complete Response and Prognosis in Patients Receiving Neoadjuvant Chemotherapy for Early Breast Cancer, " *British Journal of Cancer* 91:2012-2017.
Schein, P.S. et al. (Jun. 1, 2006). "Barriers to Efficient Development of Cancer Therapeutics," *Clinical Cancer Research* 12:3243-3248.
Semlglazov, V.F. et al. (Dec. 2002). "Breast Conserving Surgery After Neoadjuvant Chemotherapy Paclitaxel + Doxorubicin vs Fluorouracil + Doxorubicin + Cyclophosphamide in Locally Advanced Breast Cancer," *Breast Cancer Research and Treatment* 76(Supp. 1):S52, Abstract 159.
Shaked, Y. et al. (Jan. 2005). "Genetic Heterogeneity of the Vasculogenic Phenotype Parallels Angiogenesis; Implications for Cellular Surrogate Marker Analysis of Antiangiogenesis," *Cancer Cell* 7(1):101-111.

(56) References Cited

OTHER PUBLICATIONS

Taguchi, T. et al. (2001). "Special Edition. Carcinostatic Substance," *Breast Cancer Therapy of Today* 50(2):268-273. (Machine Translation, 7 pages.).

Teischer, B. A. et al. (Jun. 15, 1994). "Potentiation of Cytotoxic Cancer Therapies by TNP-470 Alone and with Other Anti-Angiogenic Agents," *Int. J. Cancer* 57(6):920-925.

Urien, S. et al. (May 1996). "Docetaxel Serum Protein Binding with High Affinity of Alpha$_1$-Acid Glycoprotein," *Invest. New Drugs* 14(2):147-151.

Van Poznak, C. et al. (May 1, 2002). "Assessment of Molecular Markers of Clinical Sensitivity to Single-Agent Taxane Therapy for Metastatic Breast Cancer," *Journal of Clinical Oncology* 20(9):2319-2326.

Vuga, M. (2005). "Sequential Therapy in Metastatic Breast Cancer: Survival Analysis With Time Dependent Covariates," MSc. Thesis, University of Pittsburg, located at <http://d-scholarship.pitt.edu/10249/1/VugaM_2005>, 51 pages.

Weidner, N. et al. (Jan. 3, 1991). "Tumor Angiogenesis and Metastasis—Correlation in Invasive Breast Carcinoma," *New Eng. J. Med.* 324(1):1-8.

Weiss, R. B. et al. (Jul. 1990). "Hypersensitivity Reactions from Taxol," *J. Clin. Oncol.* 8(7):1263-1268.

Wilks, A. (1990). "Structure and Function of the Protein Tyrosine Kinases," *Prog. Growth Factor Res.* 2(2):97-111.

Zhang, F. et al. (2003). "Correlation Between HER-2 Expression and Response to Neoadjuvant Chemotherapy With 5-Fluorouracil, Doxorubicin, and Cyclophosphamide in Patients With Breast Carcinoma," *Cancer* 97(1758-1765).

International Search Report dated May 19, 2008, for PCT Patent Application No. PCT/US07/025645 filed on Dec. 14, 2007, published on Jun. 26, 2008, as WO 2008/076373, 5 pages.

Written Opinion dated May 19, 2008, for PCT Patent Application No. PCT/US07/025645 filed on Dec. 14, 2007, published on Jun. 26, 2008, as WO 2008/076373, 8 pages.

Non-Final Office Action dated Oct. 12, 2011, for U.S. Appl. No. 12/519,126, filed Oct. 28, 2009, 8 pages.

Final Office Action dated Oct. 11, 2012, for U.S. Appl. No. 12/519,126, filed Oct. 28, 2009, 9 pages.

Non-Final Office Action dated Feb. 11, 2015, for U.S. Appl. No. 13/701,001, internationally filed on May 20, 2011, 15 pages.

Non-Final Office Action dated Feb. 12, 2015, for U.S. Appl. No. 13/782,992, filed Mar. 1, 2013, 15 pages.

U.S. Appl. No. 12/479,710, filed Jun. 5, 2009 for Desai et al.

U.S. Appl. No. 13/781,480, filed Feb. 28, 2013, for Yeo et al.

U.S. Appl. No. 15/399,366, filed Jan. 5, 2017, for Pierce et al.

U.S. Appl. No. 15/412,897, filed Jan. 23, 2017, for Foss et al.

U.S. Appl. No. 15/462,361, filed Mar. 17, 2017, for Tao et al.

U.S. Appl. No. 15/593,155, filed May 11, 2017, for Desai et al.

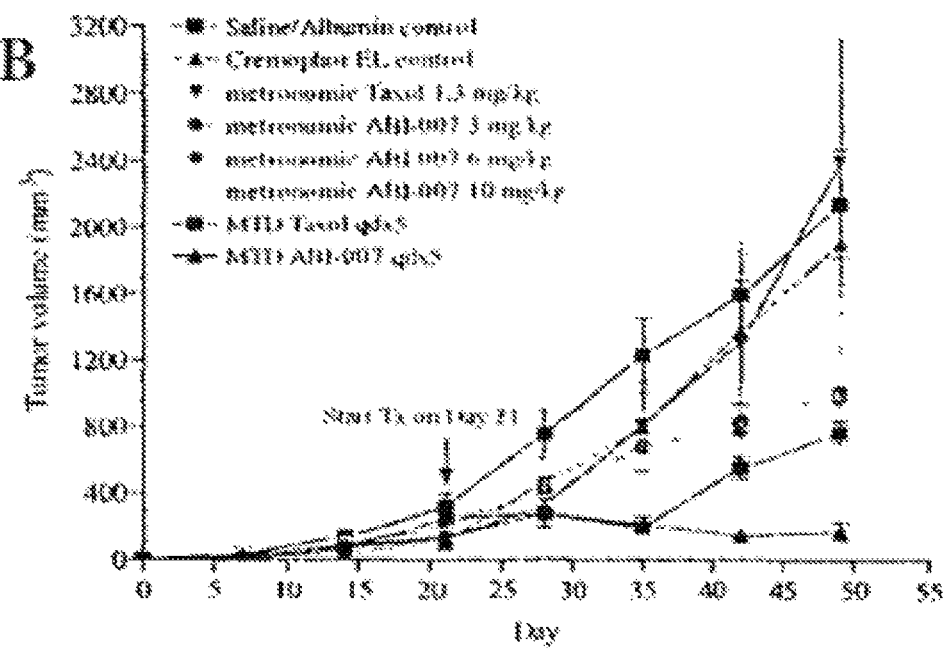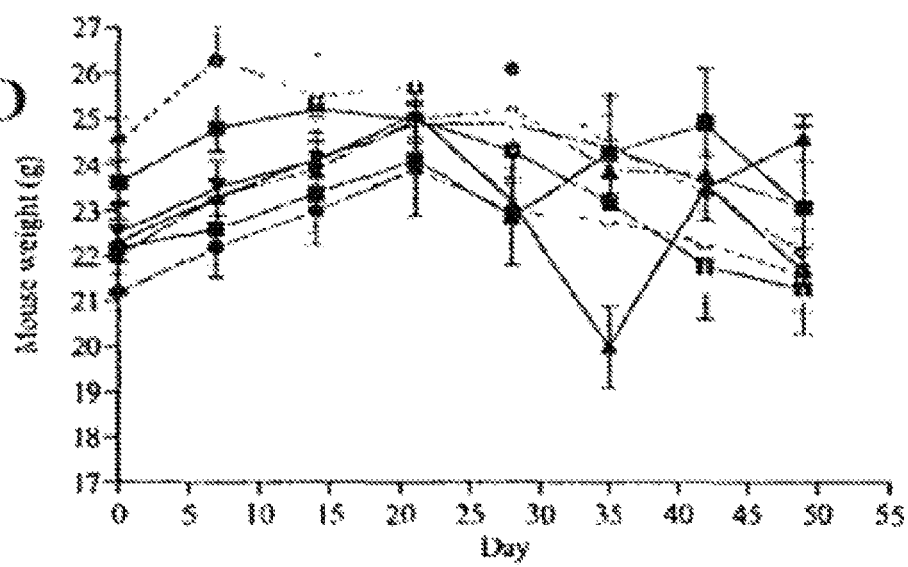

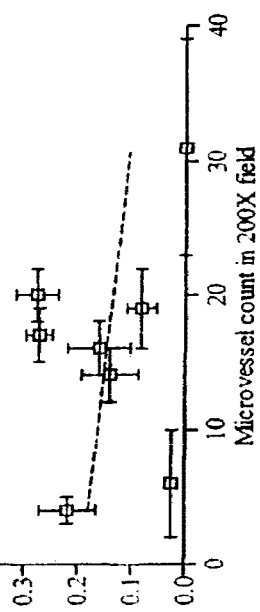
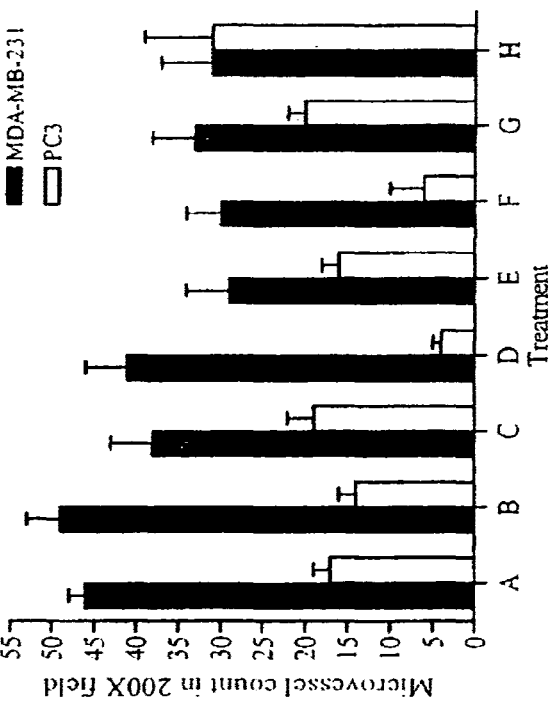
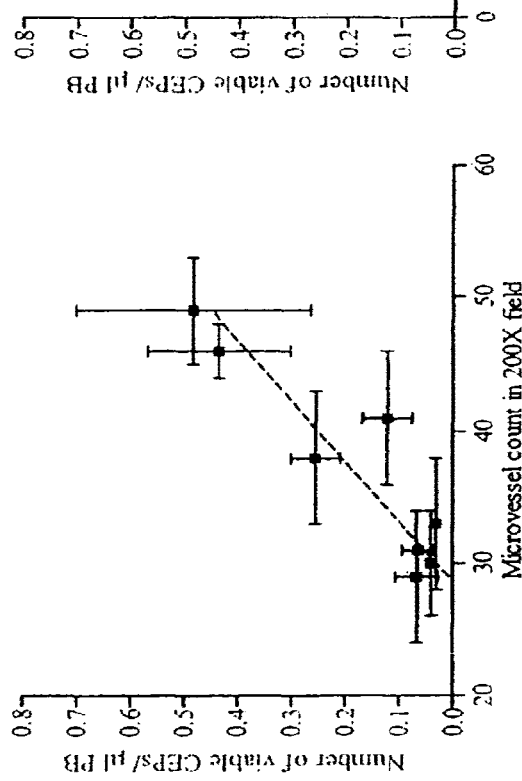
FIG. 5A
FIG. 5B
FIG. 5C

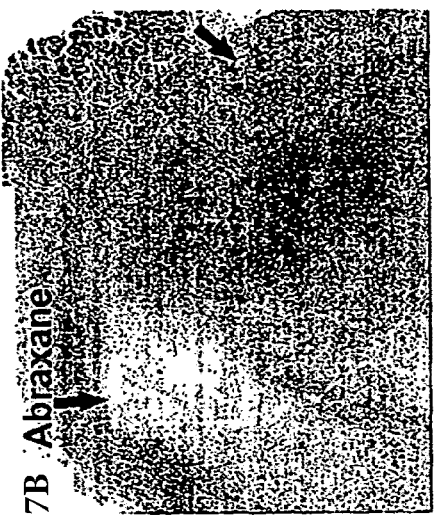
FIG. 7B Abraxane
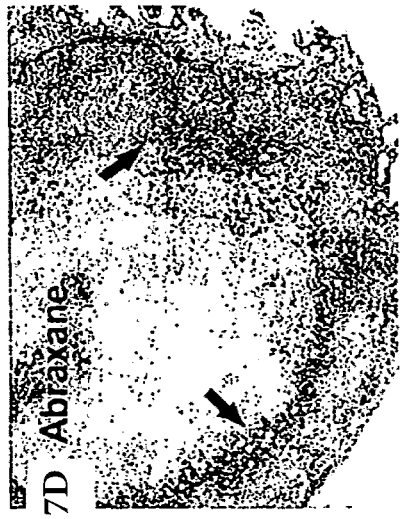
FIG. 7D Abraxane
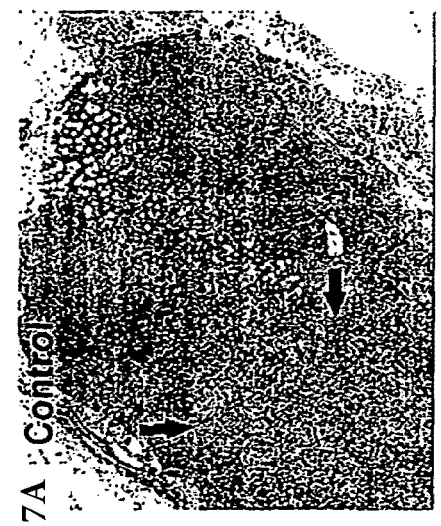
FIG. 7A Control
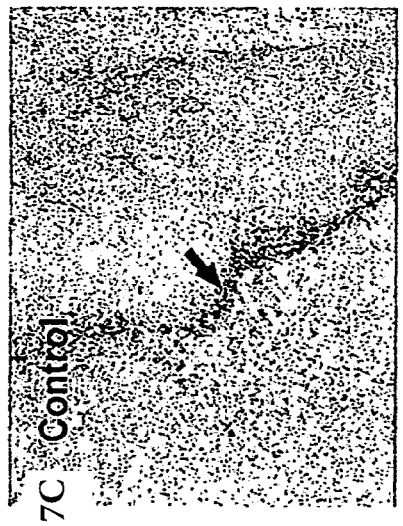
FIG. 7C Control

BREAST CANCER THERAPY BASED ON HORMONE RECEPTOR STATUS WITH NANOPARTICLES COMPRISING TAXANE

RELATED APPLICATIONS

This application is a continuation of U.S. patent application Ser. No. 12/519,126, filed Oct. 28, 2009, which is a National Phase filing under 35 U.S.C. § 371 of International Application No. PCT/US2007/025645 having an international filing date of Dec. 14, 2007, which claims priority benefit to the providional application 60/875,004, filed Dec. 14, 2006, the entire content of each of which is incorporated herein by reference.

TECHNICAL FIELD

The present invention relates to methods and kits for the treatment of breast cancer based on hormone receptor status of the progesterone receptor and the estrogen receptor comprising the administration of a taxaric alone, in combination with at least one other and other therapeutic agents, as well as other treatment modalities useful in the treatment of breast cancer. In particular, the invention relates to the use of nanoparticles comprising paclitaxel and albumin (such as Abraxane®) either alone or in combination with other chemotherapeutic agents or radiation, which may be used for the treatment of breast cancer which does not express the estrogen receptor and/or progesterone receptor.

BACKGROUND

The failure of a significant number of tumors to respond to drug and/or radiation therapy is a serious problem in the treatment of cancer. In fact, this is one of the main reasons why many of the most prevalent forms of human cancer still resist effective chemotherapeutic intervention, despite certain advances in the field of chemotherapy.

Cancer is now primarily treated with one or a combination of three types of therapies: surgery, radiation, and chemotherapy. Surgery is a traditional approach in which all or part of a tumor is removed from the body. Surgery generally is only effective for treating the earlier stages of cancer. While surgery is sometimes effective in removing tumors located at certain sites, for example, in the breast, colon, and skin, it cannot be used in the treatment of tumors located in other areas, inaccessible to surgeons, nor in the treatment of disseminated neoplastic conditions such as leukemia. For more than 50% of cancer individuals, by the time they are diagnosed they are no longer candidates for effective surgical treatment. Surgical procedures may increase tumor metastases through blood circulation during surgery. Most of cancer individuals do not die from the cancer at the time of diagnosis or surgery, but rather die from the metastasis and the recurrence of the cancer.

Other therapies are also often ineffective. Radiation therapy is only effective for individuals who present with clinically localized disease at early and middle stages of cancer, and is not effective for the late stages of cancer with metastasis. Radiation is generally applied to a defined area of the subject's body which contains abnormal proliferative tissue, in order to maximize the dose absorbed by the abnormal tissue and minimize the dose absorbed by the nearby normal tissue. However, it is difficult (if not impossible) to selectively administer therapeutic radiation to the abnormal tissue. Thus, normal tissue proximate to the abnormal tissue is also exposed to potentially damaging doses of radiation throughout the course of treatment. There are also some treatments that require exposure of the subject's entire body to the radiation, in a procedure called "total body irradiation", or "TBI." The efficacy of radiotherapeutic techniques in destroying abnormal proliferative cells is therefore balanced by associated cytotoxic effects on nearby normal cells. Because of this, radiotherapy techniques have an inherently narrow therapeutic index which results in the inadequate treatment of most tumors. Even the best radiotherapeutic techniques may result in incomplete tumor reduction, tumor recurrence, increasing tumor burden, and induction of radiation resistant tumors.

Chemotherapy involves the disruption of cell replication or cell metabolism. Chemotherapy can be effective, but there are severe side effects, e.g., vomiting, low white blood cells (WBC), loss of hair, loss of weight and other toxic effects. Because of the extremely toxic side effects, many cancer individuals cannot successfully finish a complete chemotherapy regime. Chemotherapy-induced side effects significantly impact the quality of life of the individual and may dramatically influence individual compliance with treatment. Additionally, adverse side effects associated with chemotherapeutic agents are generally the major dose-limiting toxicity (DLT) in the administration of these drugs. For example, mucositis is one of the major dose limiting toxicity for several anticancer agents, including the antimetabolite cytotoxic agents 5-FU, methotrexate, and antitumor antibiotics, such as doxorubicin. Many of these chemotherapy-induced side effects if severe may lead to hospitalization, or require treatment with analgesics for the treatment of pain. Some cancer individuals die from the chemotherapy due to poor tolerance to the chemotherapy. The extreme side effects of anticancer drugs are caused by the poor target specificity of such drugs. The drugs circulate through most normal organs of individuals as well as intended target tumors. The poor target specificity that causes side effects also decreases the efficacy of chemotherapy because only a fraction of the drugs is correctly targeted. The efficacy of chemotherapy is further decreased by poor retention of the anti-cancer drugs within the target tumors.

Due to the severity and breadth of neoplasm, tumor and cancer, there is a great need for effective treatments of such diseases or disorders that overcome the shortcomings of surgery, chemotherapy, and radiation treatment.

Problems of Chemotherapeutic Agents

The drug resistance problem is a reason for the added importance of combination chemotherapy, as the therapy both has to avoid the emergence of resistant cells and to kill pre-existing cells which are already drug resistant.

Drug resistance is the name given to the circumstance when a disease does not respond to a treatment drug or drugs. Drug resistance can be either intrinsic, which means the disease has never been responsive to the drug or drugs, or it can be acquired, which means the disease ceases responding to a drug or drugs that the disease had previously been responsive to. Multidrug resistance (MDR) is a specific type of drug resistance that is characterized by cross-resistance of a disease to more than one functionally and/or structurally unrelated drugs. Multidrug resistance in the field of cancer is discussed in greater detail in "Detoxification Mechanisms and Tumor Cell Resistance to Anticancer Drugs," by Kuzmich and Tew, particularly section VII "The Multidrug-Resistant Phenotype (MDR),"*Med. Research Rev.* 11(2): 185-217, (Section VII is at pp. 208-213) (1991); and in "Multidrug Resistance and Chemosensitization:

Therapeutic Implications for Cancer Chemotherapy," by Georges, Sharom and Ling, *Adv. in Pharmacology* 21: 185-220 (1990).

One form of multi-drug resistance (MDR) is mediated by a membrane bound 170-180 kD energy-dependent efflux pump designated as P-glycoprotein (P-gp). P-glycoprotein has been shown to play a major role in the intrinsic and acquired resistance of a number of human tumors against hydrophobic, natural product drugs. Drugs that act as substrates for and are consequently detoxified by P-gp include the vinca alkaloids (vincristine and vinblastine), anthracyclines (Adriamycin), and epipodophyllotoxins (etoposide). While P-gp associated MDR is a major determinant in tumor cell resistance to chemotherapeutic agents, it is clear that the phenomenon of MDR is multifactorial and involves a number of different mechanisms.

A major complication of cancer chemotherapy and of antiviral chemotherapy is damage to bone marrow cells or suppression of their function. Specifically, chemotherapy damages or destroys hematopoietic precursor cells, primarily found in the bone marrow and spleen, impairing the production of new blood cells (granulocytes, lymphocytes, erythrocytes, monocytes, platelets, etc.). Treatment of cancer individuals with 5-fluorouracil, for example, reduces the number of leukocytes (lymphocytes and/or granulocytes), and can result in enhanced susceptibility of the individuals to infection. Many cancer individuals die of infection or other consequences of hematopoietic failure subsequent to chemotherapy. Chemotherapeutic agents can also result in subnormal formation of platelets which produces a propensity toward hemorrhage. Inhibition of erythrocyte production can result in anemia. For some cancer individuals, the risk of damage to the hematopoietic system or other important tissues frequently limits the opportunity for chemotherapy dose escalation of chemotherapy agents high enough to provide good antitumor or antiviral efficacy. Repeated or high dose cycles of chemotherapy may be responsible for severe stem cell depletion leading to serious long-term hematopoietic sequelea and marrow exhaustion.

Prevention of, or protection from, the side effects of chemotherapy would be a great benefit to cancer individuals. For life-threatening side effects, efforts have concentrated on altering the dose and schedules of the chemotherapeutic agent to reduce the side effects. Other options are becoming available, such as the use of granulocyte colony stimulating factor (G-CSF), granulocyte-macrophage-CSF (GM-CSF), epidermal growth factor (EGF), interleukin 11, erythropoietin, thrombopoietin, megakaryocyte development and growth factor, pixykines, stem cell factor, FLT-ligand, as well as interleukins 1, 3, 6, and 7, to increase the number of normal cells in various tissues before the start of chemotherapy (See Jimenez and Yunis, *Cancer Research* 52: 413-415 (1992)). The mechanisms of protection by these factors, while not fully understood, are most likely associated with an increase in the number of normal critical target cells before treatment with cytotoxic agents, and not with increased survival of cells following chemotherapy.

Chemotherapeutic Targeting For Tumor Treatment

Both the growth and metastasis of solid tumors are angiogenesis-dependent (Folkman, *J. Cancer Res.* 46: 467-73 (1986); Folkman, *J Nat. Cancer Inst.* 82: 4-6 (1989); Folkman et al., "Tumor Angiogenesis," Chapter 10, pp. 206-32, in The Molecular Basis of *Cancer*, Mendelsohn et al., eds. (W. B. Saunders, 1995)). It has been shown, for example, that tumors which enlarge to greater than 2 mm in diameter must obtain their own blood supply and do so by inducing the growth of new capillary blood vessels. After these new blood vessels become embedded in the tumor, they provide nutrients and growth factors essential for tumor growth as well as a means for tumor cells to enter the circulation and metastasize to distant sites, such as liver, lung or bone (Weidner, *New Eng. J. Med.* 324(1): 1-8 (1991)). When used as drugs in tumor-bearing animals, natural inhibitors of angiogenesis can prevent the growth of small tumors (O'Reilly et al., *Cell* 79: 315-28 (1994)). Indeed, in some protocols, the application of such inhibitors leads to tumor regression and dormancy even after cessation of treatment (O'Reilly et al., *Cell* 88: 277-85 (1997)). Moreover, supplying inhibitors of angiogenesis to certain tumors can potentiate their response to other therapeutic regimes (e.g., chemotherapy) (see, e.g., Teischer et al., *Int J. Cancer* 57: 920-25 (1994)).

Protein tyrosine kinases catalyze the phosphorylation of specific tyrosyl residues in various proteins involved in the regulation of cell growth and differentiation (A. F. Wilks, *Progress in Growth Factor Research* (1990) 2: 97-111; S. A. Courtneidge, *Dev. Suppl.* (1993) 57-64; J. A. Cooper, *Semin. Cell Biol.* (1994) 5(6): 377-387; R. F. Paulson, *Semin. Immunol.* (1995) 7(4): 267-277; A. C. Chan, *Curr. Opin. Immunol.* (1996) 8(3): 394-401). Protein tyrosine kinases can be broadly classified as receptor (e.g., EGFr, c-erbB-2, c-met, tie-2, PDGFr, FGFr) or non-receptor (e.g., c-src, Ick, Zap70) kinases. Inappropriate or uncontrolled activation of many of these kinases, i.e., aberrant protein tyrosine kinase activity, for example by over-expression or mutation, has been shown to result in uncontrolled cell growth. For example, elevated epidermal growth factor receptor (EGFR) activity has been implicated in non-small cell lung, bladder and head and neck cancers, and increased c-erbB-2 activity in breast, ovarian, gastric and pancreatic cancers. Thus, inhibition of protein tyrosine kinases should be useful as a treatment for tumors such as those outlined above.

Growth factors are substances that induce cell proliferation, typically by binding to specific receptors on cell surfaces. Epidermal growth factor (EGF) induces proliferation of a variety of cells in vivo, and is required for the growth of most cultured cells. The EGF receptor is a 170-180 kD membrane-spanning glycoprotein, which is detectable on a wide variety of cell types. The extracellular N-terminal domain of the receptor is highly glycosylated and binds EGF antibodies that selectively bind to EGFR. Agents that competitively bind to EGFR have been used to treat certain types of cancer, since many tumors of mesodermal and ectodermal origin overexpress the EGF receptor. For example, the EGF receptor has been shown to be overexpressed in many gliomas, squamous cell carcinomas, breast carcinomas, melanomas, invasive bladder carcinomas and esophageal cancers. Attempts to exploit the EGFR system for anti-tumor therapy have generally involved the use of monoclonal antibodies against the EGFR. In addition, studies with primary human mammary tumors have shown a correlation between high EGFR expression and the presence of metastases, higher rates of proliferation, and shorter individual survival.

Herlyn et al., in U.S. Pat. No. 5,470,571, disclose the use of radiolabeled Mab 425 for treating gliomas that express EGFR. Herlyn et al. report that anti-EGFR antibodies may either stimulate or inhibit cancer cell growth and proliferation. Other monoclonal antibodies having specificity for EGFR, either alone or conjugated to a cytotoxic compound, have been reported as being effective for treating certain types of cancer. Bendig et al., in U.S. Pat. No. 5,558,864, disclose therapeutic anti-EGFR Mab's for competitively binding to EGFR. Heimbrook et al., in U.S. Pat. No.

5,690,928, disclose the use of EGF fused to a *Pseudomonas* species-derived endotoxin for the treatment of bladder cancer. Brown et al., in U.S. Pat. No. 5,859,018, disclose a method for treating diseases characterized by cellular hyperproliforation mediated by, inter alia, EGF.

Chemotherapeutic Modes of Administration

People diagnosed as having cancer are frequently treated with single or multiple chemotherapeutic agents to kill cancer cells at the primary tumor site or at distant sites to where cancer has metastasized. Chemotherapy treatment is typically given either in a single or in several large doses or over variable times of weeks to months. However, repeated or high dose cycles of chemotherapy may be responsible for increased toxicities and severe side effects.

New studies suggest that metronomic chemotherapy, the low-dose and frequent administration of cytotoxic agents without prolonged drug-free breaks, targets activated endothelial cells in the tumor vasculature. A number of preclinical studies have demonstrated superior anti-tumor efficacy, potent antiangiogenic effects, and reduced toxicity and side effects (e.g., myelosuppression) of metronomic regimes compared to maximum tolerated dose (MID) counterparts (Bocci et al., *Cancer Res* 62: 6938-6943 (2002); Bocci et al., *PNAS* 100(22): 12917-12922 (2003); and Bertolini et al., *Cancer Res* 63(15): 4342-4346 (2003)). It remains unclear whether all chemotherapeutic drugs exert similar effects or whether some are better suited for such regimes than others. Nevertheless, metronomic chemotherapy appears to be effective in overcoming some of the major shortcomings associated with chemotherapy.

Chemotherapeutic Agents

Paclitaxel has been shown to have significant antineoplastic and anticancer effects in drug-refractory ovarian cancer and has shown excellent antitumor activity in a wide variety of tumor models, and also inhibits angiogenesis when used at very low doses (Grant et al., *Int. J. Cancer,* 2003). The poor aqueous solubility of paclitaxel, however, presents a problem for human administration. Indeed, the delivery of drugs that are inherently insoluble or poorly soluble in an aqueous medium can be seriously impaired if oral delivery is not effective. Accordingly, currently used paclitaxel formulations (e.g., Taxol®) require a Cremophor® to solubilize the drug. The presence of Cremophor® in this formulation has been linked to severe hypersensitivity reactions in animals (Lorenz et al., *Agents Actions* 7: 63-67 (1987)) and humans (Weiss et al., *J. Clin. Oncol.* 8: 1263-68 (1990)) and consequently requires premedication of individuals with corticosteroids (dexamethasone) and antihistamines. It was also reported that clinically relevant concentrations of the formulation vehicle Cremophor® EL in Taxol® nullify the antiangiogenic activity of paclitaxel, suggesting that this agent or other anticancer drugs formulated in Cremophor® EL may need to be used at much higher doses than anticipated to achieve effective metronomic chemotherapy (Ng et al., *Cancer Res.* 64: 821-824 (2004)). As such, the advantage of the lack of undesirable side effects associated with low-dose paclitaxel regimes vs. conventional MTD chemotherapy may be compromised. See also U.S. Patent Pub. No. 2004/0143004; WO00/64437.

Abraxane® is a Cremophor® EL-Free Nanoparticle Albumin-Bound Paclitaxel

Preclinical models have shown significant improvement in the safety and efficacy of Abraxane® compared with Taxol® (Desai et al., EORTC-NCI-AACR, 2004) and in individuals with metastatic breast cancer (O'Shaughnessy et al., San Antonio Breast Cancer Symposium, Abstract #1122, December 2003). This is possibly due to the absence of surfactants (e.g., Cremophor® or Tween® 80, used in Taxol® and Taxotere®, respectively) in Abraxane®, and/or preferential utilization of an albumin-based transport mechanism utilizing gp60/caveolae on microvascular endothelial cells (Desai et al., EORTC-NCI-AACR, 2004). In addition, both Cremophor® and Tween® 80 have been shown to strongly inhibit the binding of paclitaxel to albumin, possibly affecting albumin based transport (Desai et al., EORTC-NCI-AACR, 2004).

IDN5109 (Ortataxel) is a new taxane, currently in phase II, selected for its lack of cross-resistance in tumor cell lines expressing the multidrug resistant phenotype (MDR/Pgp) and inhibition of P-glycoprotein (Pgp) (Minderman; *Cancer Chemother. Pharmacol.* 2004; 53: 363-9). Due to its hydrophobicity, IDN5109 is currently formulated in the surfactant Tweed® 80 (same vehicle as Taxotere®). Removal of surfactants from taxane formulations e.g., in the case of nanoparticle albumin-bound paclitaxel (Abraxane®) showed improvements in safety and efficacy over their surfactant containing counterparts (O'Shaughnessy et al., San Antonio Breast Cancer Symposium, Abstract #1122, December 2003). Tween® 80 also strongly inhibited the binding of the taxane, paclitaxel, to albumin, possibly compromising albumin based drug transport via the gp60 receptor on microvessel endothelial cells (Desai et al., EORTC-NCI-AACR, 2004).

The antitumor activity of colchicine, which is the major alkaloid of the autumn crocus, *Colchicum autumnale,* and the African climbing lily, *Gloriosa superba,* was first reported at the beginning of the 20$^{th}$ century. The elucidation of its structure was finally completed from X-ray studies and a number of total syntheses (see Shiau et al., *J. Pharm. Sci.* (1978) 67(3): 394-397). *Colchicine* is thought to be a mitotic poison, particularly in tyhmic, intestinal, and hermatopoietic cells, which acts as a spindle poison and blocks the kinesis. Its effect on the mitotic spindle is thought to represent a special case of its effects on various organized, labile, fibrillar systems concerned with structure and movement.

Thiocolchicine dimer IDN5404 was selected for its activity in human ovarian sublime resistant to cisplatin and topotecan A2780-CIS and A2780-TOP. This effect was related to dual mechanisms of action, i.e., microtubule activity as in Vinca alkaloids and a topoisomerase I inhibitory effect different from camptothecin. (Raspaglio, *Biochemical Pharmacology* 69: 113-121 (2005)).

It has been found that nanoparticle compositions of a taxane (such as albumin bound paclitaxel (Abraxane®)) have significantly lower toxicities than other taxanes like Taxol® and Taxotere® with significantly improved outcomes in both safety and efficacy.

Combination chemotherapy, e.g., combining one or more chemotherapeutic agents or other modes of treatment, e.g., combining for example, chemotherapy with radiation or surgery and chemotherapy, have been found to be more successful than single agent chemotherapeutics or individual modes of treatment respectively.

Other references include U.S. Pub. No. 2006/0013819; U.S. Pub. No. 2006/0003931; WO05/117986; WO05/117978; and WO05/000900.

More effective treatments for proliferative diseases, especially cancer, are needed.

The disclosures of all publications, patents, patent applications and published patent applications referred to herein are hereby incorporated herein by reference in their entirety.

BRIEF SUMMARY OF THE INVENTION

The present invention provides methods of treating breast cancer based on hormone receptor status (e.g., whether an individual's cell (e.g., breast cancer cells) express or do not express the estrogen receptor and/or progesterone receptor) with nanoparticles comprising a taxane and a carrier protein (such as albumin)

The invention provides a method for treating breast cancer in an individual, method includes: (a) determining hormone receptor status of estrogen receptor and/or progesterone receptor; and (b) administering to the individual an effective amount of a composition comprising nanoparticles comprising a taxane and a carrier protein.

The invention also provides a method for treating breast cancer in an individual, the method includes administering to the individual an effective amount of a composition comprising nanoparticles comprising a taxane and a carrier protein, wherein hormone receptor status of estrogen receptor and/or progesterone receptor is used as a basis for selecting the individual to receive treatment.

The invention provides a method of identifying an individual suitable for breast cancer treatment, the method includes determining hormone receptor status of estrogen receptor and/or progesterone receptor, wherein the individual is identified as suitable for breast cancer treatment with nanoparticles comprising a taxane and a carrier protein if hormone receptor status is negative for both estrogen receptor and progesterone receptor.

The invention further provides a method of assessing responsiveness of an individual to a breast cancer therapy, the method includes determining hormone receptor status of estrogen receptor and/or progesterone receptor, wherein the breast cancer therapy comprises administering a composition comprising nanoparticles comprising a taxane and a carrier protein and wherein (a) the individual is likely more responsive to the therapy if hormone receptor status is negative for both estrogen receptor and progesterone receptor and (b) the individual is likely less responsive to therapy if the hormone receptor status is positive for estrogen receptor and/or progesterone receptor.

In some embodiments of any of the above methods, the hormone receptor status of estrogen receptor and/or progesterone receptor is determined using breast cancer tissue and/or cells. In some embodiments, the hormone receptor status of the individual is negative for both estrogen receptor and progesterone receptor. In some embodiments, the breast cancer is locally advanced breast cancer. In some embodiments, the breast cancer expresses HER2 (HER2+). In some embodiments, the breast cancer does not express HER2 (HER2−). In some embodiments, the individual is human.

In some embodiments of any of the above methods, the method further includes administering to the individual an effective amount of at least one other chemotherapeutic agent. In some embodiments, the at least one other chemotherapeutic agent comprises 5-fluorouracil, epirubicin, and cyclosphosphamide. In some embodiments, the composition comprising nanoparticles (also referred to as "nanoparticle composition") and the chemotherapeutic agent are administered simultaneously, either in the same composition or in separate compositions. In some embodiments, the nanoparticle composition and the chemotherapeutic agent are administered sequentially, i.e., the nanoparticle composition is administered either prior to or after the administration of the chemotherapeutic agent. In some embodiments, the administration of the nanoparticle composition and the chemotherapeutic agent are concurrent, i.e., the administration period of the nanoparticle composition and that of the chemotherapeutic agent overlap with each other. In some embodiments, the administration of the nanoparticle composition and the chemotherapeutic agent are non-concurrent. For example, in some embodiments, the administration of the nanoparticle composition is terminated before the chemotherapeutic agent is administered. In some embodiments, the administration of the chemotherapeutic agent is terminated before the nanoparticle composition is administered.

In some embodiments of any of the above methods, the method further includes a second therapy including radiation therapy, surgery, or combinations thereof. In some embodiments, the second therapy is radiation therapy. In some embodiments, the second therapy is surgery. In some embodiments, the first therapy is carried out prior to the second therapy. In some embodiments, the first therapy is carried out after the second therapy.

In some embodiments of any of the above methods, the method further includes metronomic therapy regimes. In some embodiments, there is provided a method of administering a composition comprising nanoparticles comprising a taxane and a carrier protein (such as albumin), wherein the nanoparticle composition is administered over a period of at least one month, wherein the interval between each administration is no more than about a week, and wherein the dose of taxane at each administration is about 0.25% to about 25% of its maximum tolerated dose following a traditional dosing regime. In some embodiments, there is provided a method of administering a composition comprising nanoparticles comprising paclitaxel and an albumin (such as Abraxane®), wherein the nanoparticle composition is administered over a period of at least one month, wherein the interval between each administration is no more than about a week, and wherein the dose of paclitaxel at each administration is about 0.25% to about 25% of its maximum tolerated dose following a traditional dosing regime. In some embodiments, the dose of the taxane (such as paclitaxel, for example Abraxane®) per administration is less than about any of 1%, 2%, 3%, 4%, 5%, 6%, 7%. 8%, 9%, 10%, 11%, 12%, 13%, 14%, 15%, 18%, 20%, 22%, 24%, or 25% of the maximum tolerated dose. In some embodiments, the nanoparticle composition is administered at least about any of 1×, 2×, 3×, 4×, 5×, 6×, 7× (i.e., daily) a week. In some embodiments, the intervals between each administration are less than about any of 7 days, 6 days, 5 days, 4 days, 3 days, 2 days, and 1 day. In some embodiments, the nanoparticle composition is administered over a period of at least about any of 2, 3, 4, 5, 6, 7, 8, 9, 10, 11, 12, 18, 24, 30 and 36 months.

The methods of the invention generally comprise administration of a composition comprising nanoparticles comprising a taxane and a carrier protein. In some embodiments, the nanoparticle composition comprises nanoparticles comprising paclitaxel and an albumin. In some embodiments, the paclitaxel albumin nanoparticles have an average diameter of no greater than about 200 nm. In some embodiments, the paclitaxel/albumin nanoparticle composition is substantially free (such as free) of surfactant (such as Cremophor). In some embodiments, the weight ratio of the albumin to paclitaxel in the composition is about 18:1 or less, such as about 9:1 or less. In some embodiments, the paclitaxel is coated with albumin. In some embodiments, the albumin is human serum albumin. In some embodiments, the paclitaxel/albumin nanoparticles have an average diameter of no greater than about 200 nm and the paclitaxel/albumin composition is substantially free (such as free) of surfactant (such as Cremophor), In some embodiments, the paclitaxel/albumin nanoparticles have an average diameter of no greater than about 200 nm and the paclitaxel is coated with albumin. Other combinations of the above characteristics are also contemplated. In some embodiments, the nanoparticle composition is Abraxane®. Nanoparticle compositions comprising other taxanes (such as docetaxel and ortataxel) may also comprise one or more of the above characteristics. In some embodiments, the nanoparticles comprising a taxane and a carrier protein is the nanoparticle albumin bound paclitaxel, described, for example, in U.S. Pat. No. 6,566,405, and commercially available under the tradename Abraxane®. In addition, the nanoparticles comprising a taxane and a carrier protein is considered to be nanoparticle albumin bound docetaxel described for example in U.S. Patent Application Publication 2005/0004002A1.

In some embodiments, there is provided a method of administering a composition comprising nanoparticles comprising a taxane and a carrier protein (such as albumin), wherein the taxane is administered over a period of at least one month, wherein the interval between each administration is no more than about a week, and wherein the dose of the taxane at each administration is about 0.25 ng/m' to about 25 mg/m$^2$. In some embodiments, there is provided a method of administering a composition comprising nanoparticles comprising paclitaxel and an albumin (such as Abraxane®) and a carrier protein (such as albumin), wherein the paclitaxel is administered over a period of at least one month, wherein the interval between each administration is no more than about a week, and wherein the dose of the taxane at each administration is about 0.25 mg/m$^2$ to about 25 mg/m$^2$. In some embodiments, the dose of the taxane (such as paclitaxel, for example Abraxane®) per administration is less than about any of 2, 3, 4, 5, 6, 7, 8, 9, 10, 11, 12, 13, 14, 15, 18, 20, 22, and 25 mg/m$^2$. In some embodiments, the nanoparticle composition is administered at least about any of 1×, 2×, 3×, 4×, 5×, 6×, 7× (i.e., daily) a week. In some embodiments, the intervals between each administration are less than about any of 7 days, 6 days, 5 days, 4 days, 3 days, 2 days, and 1 day. In some embodiments, the nanoparticle composition is administered over a period of at least about any of 2, 3, 4, 5, 6, 7, 8, 9, 10, 11, 12, 18, 24, 30 and 36 months.

The invention also provides a kit comprising: (a) an agent for detecting hormone receptor status of estrogen receptor and/or progesterone receptor of a breast cancer patient; and (b) a composition comprising nanoparticles comprising a taxane and a carrier protein.

The invention further provides a kit comprising: (a) an agent for detecting hormone receptor status of estrogen receptor and/or progesterone receptor of a breast cancer patient; and (b) instructions for assessing likely responsiveness to therapy for treating breast cancer based on hormone receptor status of estrogen receptor and/or progesterone receptor, wherein the therapy comprises administering a composition comprising nanoparticles comprising a taxane and a carrier protein. In some embodiments, the instructions further provide instructions for administering to the patient an effective amount of the composition.

In some embodiments of any of the kits, the hormone receptor status of estrogen receptor and/or progesterone receptor is determined using breast cancer tissue and/or cells. In some embodiments, the hormone receptor status of the individual is negative for both estrogen receptor and progesterone receptor. In some embodiments, the breast cancer is locally advanced breast cancer. In some embodiments, the breast cancer expresses HER2 (HER2+). In some embodiments, the breast cancer does not express HER2 (HER2−). In some embodiments, the kit further includes at least one other chemotherapeutic agent. In some embodiments, the at least one other chemotherapeutic agent comprises 5-fluorouracil, epirubicin, and cyclophosphamide.

In some embodiments, the kits comprise a composition comprising nanoparticles comprising a taxane and a carrier protein. In some embodiments, the nanoparticle composition comprises nanoparticles comprising paclitaxel and an albumin. In some embodiments, the paclitaxel/albumin nanoparticles have an average diameter of no greater than about 200 nm. In some embodiments, the paclitaxel/albumin nanoparticle composition is substantially free (such as free) of surfactant (such as Cremophor). In some embodiments, the weight ratio of the albumin to paclitaxel in the composition is about 18:1 or less, such as about 9:1 or less. In some embodiments, the paclitaxel is coated with albumin. In some embodiments, the albumin is human serum albumin. In some embodiments, the paclitaxel/albumin nanoparticles have an average diameter of no greater than about 200 run and the paclitaxel/albumin composition is substantially free (such as free) of surfactant (such as Cremophor). In some embodiments, the paclitaxel/albumin nanoparticles have an average diameter of no greater than about 200 nm and the paclitaxel is coated with albumin. Other combinations of the above characteristics are also contemplated. In some embodiments, the nanoparticle composition is Abraxane®. Nanoparticle compositions comprising other taxanes (such as docetaxel and ortataxel) may also comprise one or more of the above characteristics. In some embodiments, the nanoparticles comprising a taxane and a carrier protein is the nanoparticle albumin bound paclitaxel, described, for example, in U.S. Pat. No. 6,566,405, and commercially available under the tradename Abraxane®. In addition, the nanoparticles comprising a taxane and a carrier protein is considered to be nanoparticle albumin bound docetaxel described for example in U.S. Patent Application Publication 2005/0004002A1.

These and other aspects and advantages of the present invention will become apparent from the subsequent detailed description and the appended claims. It is to be understood that one, some, or all of the properties of the various embodiments described herein may be combined to form other embodiments of the present invention.

BRIEF DESCRIPTION OF FIGURES

FIGS. 3A and 3B show the effects of ABI-007 and Taxol® used in metronomic or MTD regimes on MDA-MB-231 (FIG. 3A) and PC3 (FIG. 3B) tumor growth tumor-bearing SCID mice. FIGS. 3C and 3D show the effects of ABI-007 and Taxol® used in metronomic or MTD regimes on the body weight of MDA-MB-231 (FIG. 3C) and PC3 (FIG. 3D) tumor-bearing SCID mice.

Bars, mean±SE. [a] Significantly (p<0.05) different from saline/albumin vehicle control. [b] Significantly (p<0.05) different from Cremophor EL vehicle control.

FIG. 5A shows intratumoral microvessel density of MDA-MB-231 (■) and PC3 (□) xenografts treated with A, saline/albumin; B, Cremophor EL control; C, metronomic Taxol® 1.3 mg/kg; D, E, and F, metronomic ABI-007 3, 6, and 10 mg/kg, respectively; G, MTD Taxol; H, MTD ABI-007. Bars, mean±SE. FIGS. 5B and 5C show the correlation between intratumoral microvessel density and the number of viable CEPs in peripheral blood in MDA-MB-231 (FIG. 5B) and PC3 (FIG. 5C) tumor-bearing SCID mice.

Figure 6:
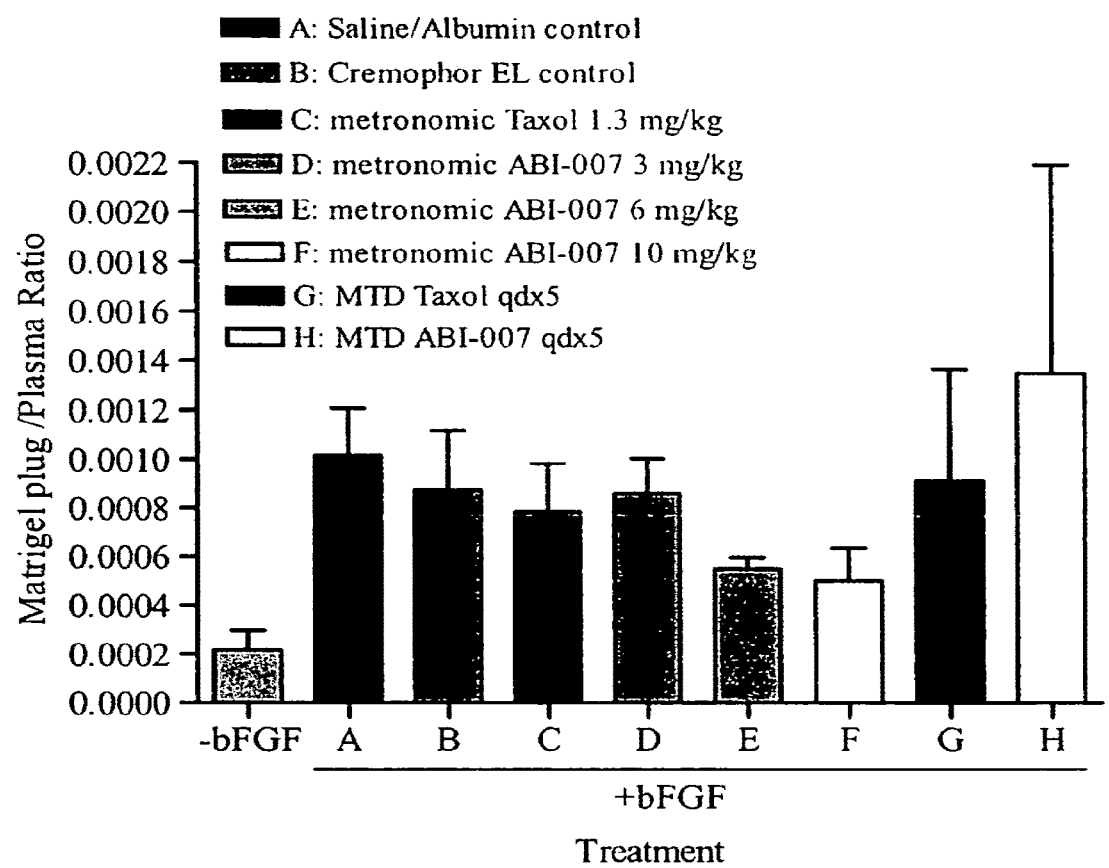

FIG. 6 shows the effects of ABI-007 or Taxol used in metronomic or MTD regimes on basic fibroblast growth factor (bFGF)-induced angiogenesis in matrigel plugs injected subcutaneously into the flanks of Balb/cJ mice. Treatments-A, saline/albumin; B, Cremophor EL control; C, metronomic Taxol 1.3 mg/kg; D, E, and F, metronomic ABI-007 3, 6, and 10 mg/kg, respectively; G, MTD Taxol; H, MTD ABI-007. Matrigel implanted without bFGF (−bFGF) served as negative control. Bars, mean±SE.

FIGS. 7A and 7B show necrosis in MDA-MB-231 tumor cells after treatment with saline control or Abraxane®. FIGS. 7C and 7D show hypoxia in MDA-MB-231 cells after treatment with saline control or Abraxane®. Arrows indicate sites of necrosis (FIGS. 7A and 7B) or sites of hypoxia (FIGS. 7C and 7D).

Figure 8B:
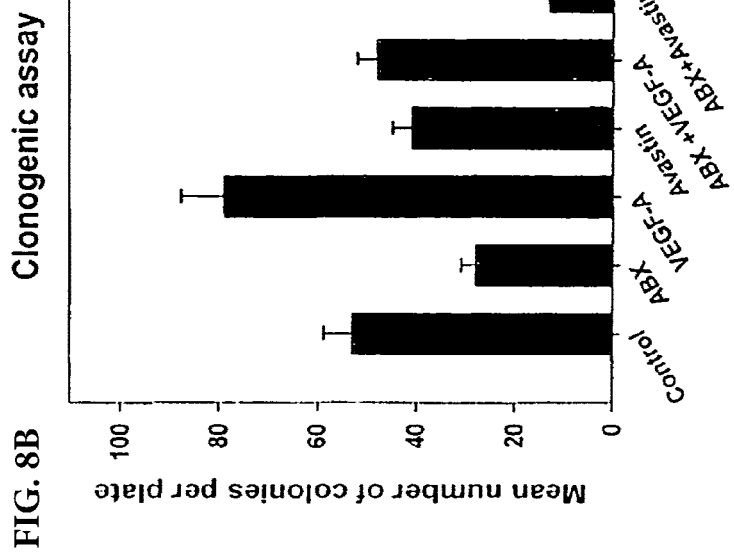
Figure 8A:
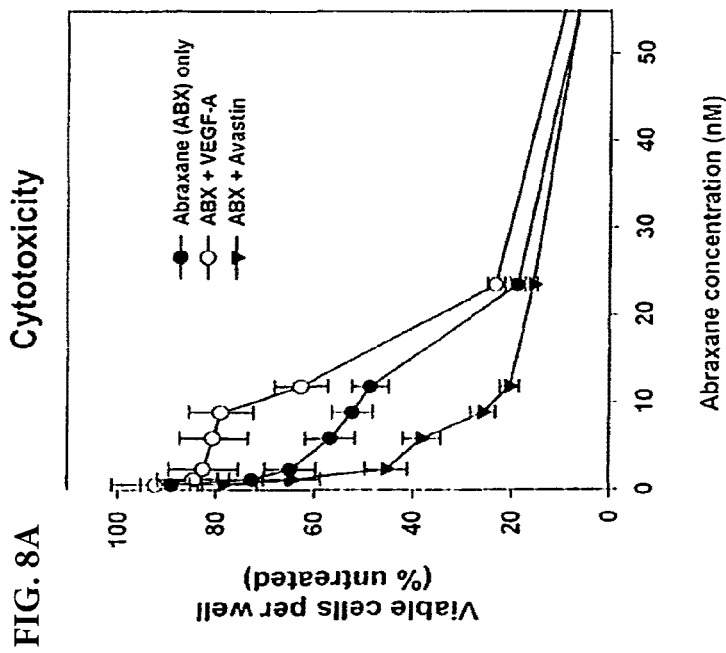

FIGS. 8A and 8B show the effect of VEGF-A and Avastin® on Abraxane®-treated cells in cytotoxicity and clonogenic assays. In FIG. 8A, results are shown as viable cells as a percentage of untreated cells. Dark circles indicate cells treated with Abraxane® alone; open circles indicate cells treated with Abraxane® and VEGF-A; dark triangles indicate cells treated with Abraxane® and Avastin®. In FIG. 8B, results are shown as the mean number of cell colonies per plate.

Figure 9:
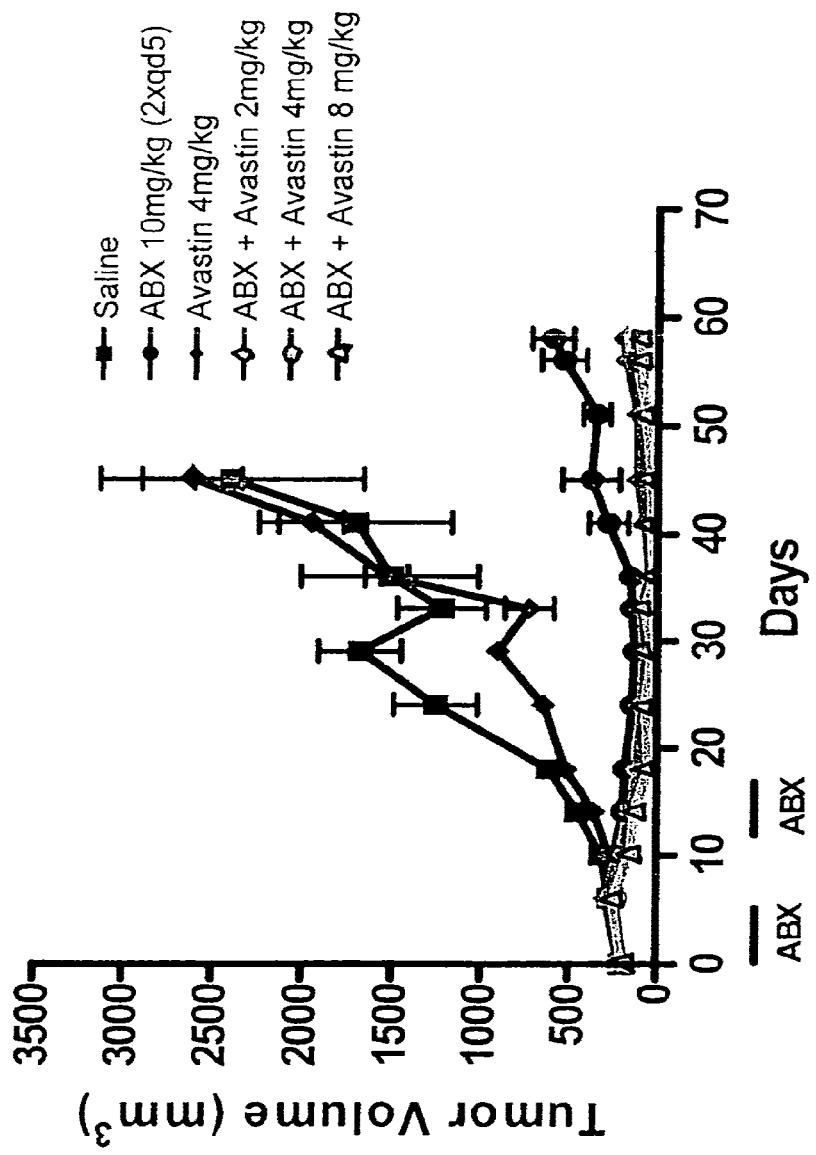

FIG. 9 shows the effect of Abraxane® and Avastin® treatment on the growth of MDA-MB-231 breast tumor xenografts. Dark squares indicate mean tumor volume in saline-treated mice; dark circles indicate mean tumor volume in Abraxane®-treated mice; dark diamonds indicate mean tumor volume in Avastin®-treated mice; open diamonds indicate mean tumor volume in Abraxane®+Avastin® (2 mg/kg)-treated mice; open circles indicate mean tumor volume in Abraxane®+Avastin® (4 mg/kg)-treated mice; triangles indicate mean tumor volume in Abraxane®+Avastin® (8 mg/kg)-treated mice. Two bars labeled ABX indicate the two Abraxane® treatment cycles.

Figure 10B:
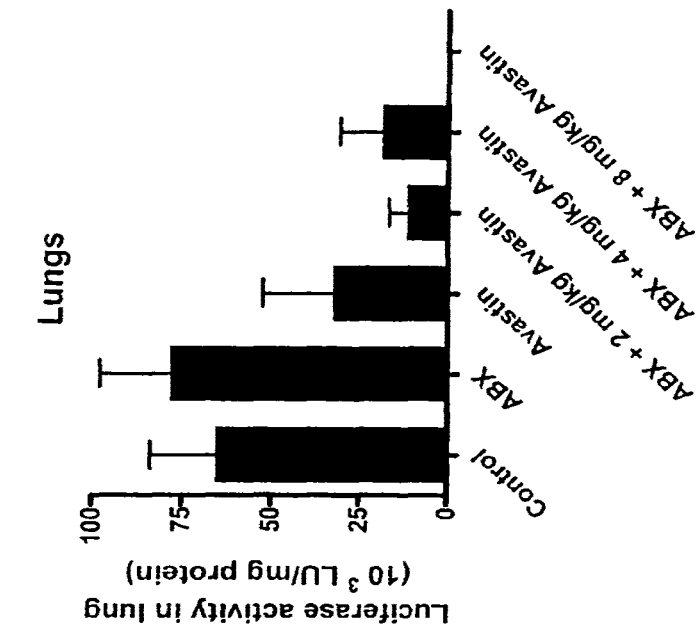
Figure 10A:
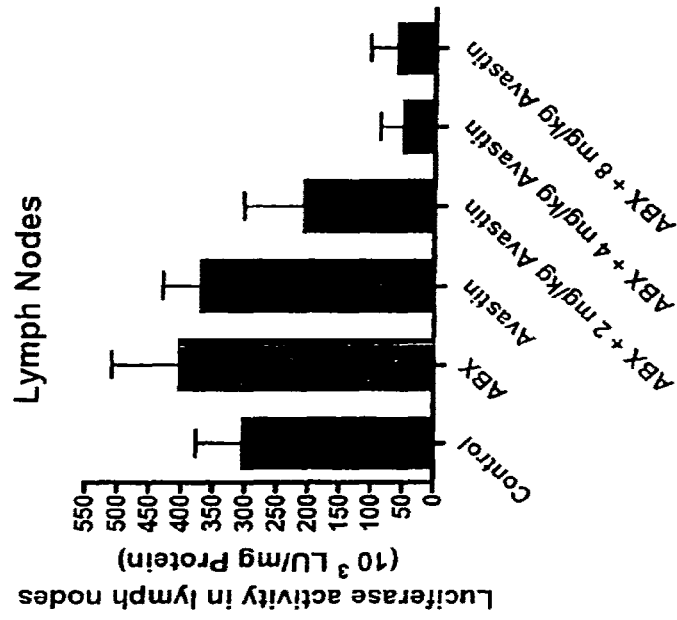

FIGS. 10A and 10B show the effect of Abraxane® and Avastin® treatment on metastasis of luciferase-expressing MDA-MB-231 tumor cells to the lymph nodes and lungs in tumor-bearing mice. Results are shown as levels of luciferase activity in lymph node or lung cellular extracts.

DETAILED DESCRIPTION OF THE INVENTION

The present invention provides methods of treating breast cancer based on hormone receptor status (e.g., whether an individual's cell (e.g, breast cancer cells) express or do not express the estrogen receptor and/or progesterone receptor) with nanoparticles comprising a taxane and a carrier protein (such as albumin). The treatments can further involve combination therapy comprising a first therapy comprising administration of nanoparticles comprising a taxane and a carrier protein (such as albumin) in conjunction with a second therapy such as radiation, surgery, administration of at least one other chemotherapeutic agent, or combinations thereof for the treatment of breast cancer based on hormone status. The treatments can further involve metronomic therapy for the treatment of breast cancer based on hormone receptor status.

The present invention involves the discovery that Abraxane®, due to its superior anti-tumor activity and reduced toxicity and side effects, can be administered alone, in combination with other therapeutic drugs and/or treatment modalities and can also be used in metronomic chemotherapy to treat breast cancer based on hormone receptor status. Due to significantly improved safety profiles with compositions comprising drug/carrier protein nanoparticles (such as Abraxane®), we believe that monotherapy and combination chemotherapy with such nanoparticle compositions (such as Abraxane®) is more effective than monotherapy with non-nanoparticle formulations or combination chemotherapy with other drugs in treating breast cancer based on hormone receptor status (e.g., not expressing the estrogen receptor and/or progesterone receptor). In addition the use of nanoparticle composition (such as Abraxane®) in combination with radiation is also believed to be more effective than combination of other agents with radiation in the treatment of breast cancer based on hormone receptor status. Thus, the nanoparticle compositions (especially a paclitaxel/albumin nanoparticle composition, such as Abraxane®), when used alone, in combination with other chemotherapeutic agents, or when combined with other treatment modalities, should be very effective and overcome the deficiencies of surgery, radiation treatment, and chemotherapy in the treatment of breast cancer based on hormone receptor status (e.g., not expressing the estrogen receptor and/or progesterone receptor).

The present invention in one its embodiments is the use of a composition comprising a taxane, such as Abraxane® for the treatment of breast cancer based on hormone receptor status (e.g., not expressing the estrogen receptor and/or progesterone receptor). In some embodiments, the present invention is the use of a first therapy comprising a taxane, such as Abraxane®, in combination with a second therapy such as another chemotherapeutic agent or agents, radiation, or the like for treating breast cancer based on hormone receptor status. The first therapy comprising a taxane and second therapy can be administered to a mammal having the proliferative sequentially, or they can be co-administered, and even administered simultaneously in the same pharmaceutical composition.

Further, a metronomic dosing regime using Abraxane® has been found to be more effective than the traditional MTD dosing schedule of the same drug composition. Such metronomic dosing regime of Abraxane® has also been found to be more effective than metronomic dosing of Taxol®.

The methods described herein are generally useful for treatment of diseases, particularly proliferative diseases. As used herein, "treatment" is an approach for obtaining beneficial or desired clinical results. For purposes of this invention, beneficial or desired clinical results include, but are not limited to, any one or more of: alleviation of one or more symptoms, diminishment of extent of disease, stabilized (i.e., not worsening) state of disease, preventing or delaying spread (e.g., metastasis) of disease, preventing or delaying occurrence or recurrence of disease, delay or slowing of disease progression, amelioration of the disease state, and remission (whether partial or total). Also encompassed by "treatment" is a reduction of pathological consequence of a proliferative disease. The methods of the invention contemplate any one or more of these aspects of treatment.

As used herein, a "proliferative disease" is defined as a tumor disease (including benign or cancerous) and/or any metastases, wherever the tumor or the metastasis are located, more especially a breast cancer tumor. In some embodiments, the proliferative disease is cancer. In some embodiments, the proliferative disease is a benign or malignant tumor. Where hereinbefore and subsequently a tumor, a tumor disease, a carcinoma or a cancer are mentioned, also metastasis in the original organ or tissue and/or in any other location are implied alternatively or in addition, whatever the location of the tumor and/or metastasis is.

The term "effective amount" used herein refers to an amount of a compound or composition sufficient to treat a specified disorder, condition or disease such as ameliorate, palliate, lessen, and/or delay one or more of its symptoms. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay occurrence and/or recurrence. An effective amount can be administered in one or more administrations. In the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

In some embodiments, there is provided a method of treating a primary tumor. In some embodiments, there is provided a method of treating metastatic cancer (that is, cancer that has metastasized from the primary tumor). In some embodiments, there is provided a method of treating cancer at advanced stage(s). In some embodiments, there is provided a method of treating breast cancer (which may be HER2 positive or HER2 negative), including, for example, advanced breast cancer, stage IV breast cancer, locally advanced breast cancer, and metastatic breast cancer. In some embodiments, there is provided a method of treating solid tumors (such as advanced solid tumors). In some embodiments, there is provided a method of reducing cell proliferation and/or cell migration. The present invention also provides methods of delaying development of any of the proliferative diseases described herein.

The term "individual" is a mammal, including humans. An individual includes, but is not limited to, human, bovine, horse, feline, canine, rodent, or primate. In some embodiments, the individual is human. The individual (such as human) may have advanced disease or lesser extent of disease, such as low tumor burden. In some embodiments, the individual is at an early stage of a proliferative disease (such as cancer). In some embodiments, the individual is at an advanced stage of a proliferative disease (such as an advanced cancer). In some embodiments, the individual is HER2 positive. In some embodiments, the individual is HER2 negative.

The methods may be practiced in an adjuvant setting. "Adjuvant setting" refers to a clinical setting in which an individual has had a history of a proliferative disease, particularly cancer, and generally (but not necessarily) been responsive to therapy, which includes, but is not limited to, surgery (such as surgical resection), radiotherapy, and chemotherapy. However, because of their history of the proliferative disease (such as cancer), these individuals are considered at risk of development of the disease. Treatment or administration in the "adjuvant setting" refers to a subsequent mode of treatment. The degree of risk (i.e., when an individual in the adjuvant setting is considered as "high risk" or "low risk") depends upon several factors, most usually the extent of disease when first treated. The methods provided, herein may also be practiced in a neoadjuvant setting, i.e., the method may be carried out before the primary/definitive therapy. In some embodiments, the individual has previously been treated. In some embodiments, the individual has not previously been treated. In some embodiments, the treatment is a first line therapy.

It is understood that aspect and embodiments of the invention described herein include "consisting" and/or "consisting essentially of" aspects and embodiments.

As is understood by one skilled in the art, reference to "about" a value or parameter herein includes (and describes) embodiments that are directed to that value or parameter per se. For example, description referring to "about X" includes description of "X".

When hormone receptor status "is used as a basis" for administration of the treatment methods described herein, or selection for the treatment methods described herein, hormone receptor status is measured before and/or during treatment, and the values obtained are used by a clinician in assessing any of the following: (a) probable or likely suitability of an individual to initially receive treatment(s); (b) probable or likely unsuitability of an individual to initially receive treatment(s); (c) responsiveness to treatment; (d) probable or likely suitability of an individual to continue to receive treatment(s); (e) probable or likely unsuitability of an individual to continue to receive treatment(s); (f) adjusting dosage; or (g) predicting likelihood of clinical benefits.

Method of Treatment

The present invention provides methods of treating breast cancer based on hormone receptor status of the breast cancer tissue with a composition comprising nanoparticles comprising a taxane and a carrier protein. In some embodiments, the hormone receptor status is determined based on the expression of a hormone receptor such as the estrogen receptor (ER) or the progesterone receptor (PgR). In some embodiments, the hormone receptor status is determined based on the expression of a hormone receptor such as the estrogen receptor and the progesterone receptor of the breast cancer tissue and/or cells.

In some embodiments, the hormone receptor status is low for one or more hormone receptors such as the estrogen receptor and/or the progesterone receptor. In some embodiments, the individual is likely more responsive to the therapy if hormone receptor status is low for both estrogen receptor and progesterone receptor. In some embodiments, the hormone receptor status does not express (i.e., is negative for) one or more hormone receptors such as the estrogen receptor (ER) or the progesterone receptor (PgR). In some embodiments, the hormone receptor status of the breast cancer tissue does not express is negative for) both the estrogen receptor (ER) and the progesterone receptor (PgR). In some embodiments, the individual is likely more responsive to the therapy if hormone receptor status is negative for both estrogen receptor and progesterone receptor. In some embodiments, the individual expresses (i.e., is positive for) either the estrogen receptor or the progesterone receptor. In some embodiments, the individual expresses (i.e., is positive for) both the estrogen receptor and the progesterone receptor. In some embodiments, the individual is likely less responsive to therapy if the hormone receptor status is positive for the estrogen receptor and/or the progesterone receptor.

In some embodiments, the breast cancer further expresses HER2 (HER2+). In some embodiments, the breast cancer further does not express HER2 (HER2−).

In some embodiments, the nanoparticles have an average diameter of no greater than about 200 nm. In some embodiments, the nanoparticle composition is substantially free (such as free) of surfactant (such as Cremophor). In some embodiments, the taxane is paclitaxel. In some embodiments, the carrier protein is albumin. In some embodiments, the albumin is human serum albumin. In some embodiments, the weight ratio of the albumin to paclitaxel in the composition is about 18:1 or less, such as about 9:1 or less. In some embodiments, the paclitaxel is coated with albumin. In some embodiments, the paclitaxel/albumin nanoparticles have an average diameter of no greater than about 200 nm and the paclitaxel/albumin composition is substantially free (such as free) of surfactant (such as Cremophor). In some embodiments, the paclitaxel/albumin nanoparticles have an average diameter of no greater than about 200 nm and the paclitaxel is coated with albumin. In some embodiments, the nanoparticle composition is Abraxane®.

Estrogen, mediated through the estrogen receptor (ER), plays a major role in regulating the growth and differentiation of normal breast epithelium (Pike M C et al. *Epidemiologic Reviews* (1993) 15(1): 17-35; Henderson B E et al. *Cancer Res*. (1988) 48: 246-253). It stimulates cell proliferation and regulates the expression of other genes, including the progesterone receptor (PgR). PgR then mediates the mitogenic effect of progesterone, further stimulating proliferation (Pike et al., 1993; Henderson et al., 1988). The molecular differences between estrogen receptor ("ER") negative and ER positive tumors are significant in light of clinical observations which indicate that the nature and biological behavior of ER positive and ER negative tumors are distinct even in the absence of hormonal therapy. For example, ER negative cancers tend to recur sooner and show a different rate of recurrence in distant organ sites compared to ER positive tumors. Clinical observations and molecular profiling data suggest that tumors not expressing both ER and PgR represent a different clinical entity in terms of chemotherapy responsiveness. (Colleoni et al., *Annals of Oncology* 11(8): 1057 (2000)). Thus, ER negative and ER positive breast cancers are two distinct disease entities rather than phenotypic variations of the same disease.

In some embodiments, the method comprises identifying a breast cancer patient based on a hormone receptor status of patients having tumor tissue not expressing both ER and PgR. Suitable patients are administered an effective amount of a composition comprising nanoparticles comprising a taxane (such as paclitaxel, docetaxel, or ortataxel) and a carrier protein (such as albumin). In some embodiments, the method further comprises administering to the patient an effective amount of at least one other chemotherapeutic agent. The at least one other chemotherapeutic agent may be administered concurrently or sequentially with the taxane nanoparticles. In some embodiments the at least one other chemotherapeutic agent comprises 5-Fluoruracil, Epirubicin and Cyclophosphamide (FEC) administered concurrently or sequentially. These methods have higher efficacy in ER(−)/PgR(−) populations in all patient populations, both HER-2 positive and HER-2 negative.

Various methods can be used to determine hormone receptor status and measure hormone receptor levels (e.g., estrogen receptor levels and/or progesterone receptor levels) in a sample (e.g., breast cancer tissue). Methods for measuring RNA levels include, without limitation, hybridization (e.g., Northern blotting of separated RNAs, microarray, and dot or slot blotting or total RNA) and PCR-based methods (e.g., RT-PCR and quantitative real-time PCR). For example, hybridization can be done by Northern analysis to identify an RNA sequence that hybridizes to a probe. The probe can be labeled with a radioisotope such as $^{32}$P, an enzyme, digoxygenin, or by biotinylation. The RNA to be analyzed can be electrophoretically separated on an agarose or polyacrylamide gel, transferred to nitrocellulose, nylon, or other suitable membrane, and hybridized with the probe using standard techniques well known in the art such as those described in sections 7.39-7.52 of Sambrook et al., (1989) Molecular Cloning, second edition, Cold Spring Harbor Laboratory, Plainview, N.Y.

As standard Northern blot assays can be used to ascertain the level of a particular RNA in a sample from a mammal, so can PCR-based methods such as quantitative real-time PCR. In one embodiment, reverse transcription using random hexamer oligonucleotide primers can be performed on total mRNA isolated from a cancer sample. The resulting cDNA then can be used as template in quantitative real-time PCR experiments using forward and reverse oligonucleotide primers in the presence of a specific probe (e.g., a probe having a 5' fluorescent reporter dye at one end and a 3' quencher dye at the other end). Reactions can be monitored using the point during cycling when amplification of a PCR product is first detected, rather than the amount of PCR product accumulated after a fixed number of cycles. The resulting quantitated PCR product levels can be correlated to the mRNA levels in the original cancer sample, and the mRNA levels can in turn be correlated with the aggressiveness of that cancer.

Methods for measuring polypeptide hormone receptor levels (e.g., estrogen receptor protein levels and/or progesterone receptor protein levels) include, without limitation, ELISA-, immunohistochemistry-, and immunofluorescence-based techniques. Such methods typically employ antibodies having specific binding affinity for a particular polypeptide. "Specific binding affinity" refers to an antibody's ability to interact specifically with a particular polypeptide without significantly cross-reacting with other different polypeptides in the same environment. An antibody having specific binding affinity for estrogen receptor or progesterone receptor can interact with estrogen receptor or progesterone receptor polypeptides.

Estrogen receptor or progesterone receptor polypeptide levels in a breast cancer sample can, for example, be measured using a quantitative sandwich ELISA technique. Breast cancer tissue samples can be homogenized and extracted, and aliquots of the extracts added to separate wells of a microtiter plate pre-coated with antibodies specific for estrogen receptor or progesterone receptor. After protein binding and subsequent washing, enzyme-linked antibodies specific for estrogen receptor or progesterone receptor can be added to the wells. After antibody binding and subsequent washing, a substrate solution containing a label-conjugated IgG can be added to the wells (e.g., horseradish peroxidase (HRP)-conjugated IgG). The label then can be quantitated by spectrophotometry and the quantitated levels compared to a control level or baseline. The resulting quantitated polypeptide levels can be correlated with the aggressiveness of that cancer.

Polypeptide levels also can be measured by immunohistochemistry. For example, a section of a breast cancer tissue sample can be treated with anti-estrogen receptor or anti-progesterone receptor antibodies. Negative control sections can be incubated with pre-immune rabbit or mouse serum in lieu of primary antibodies. After antibody binding and subsequent washing, the primary antibodies can be detected with appropriate label-conjugated secondary antibodies (e.g, gold-conjugated or enzyme-conjugated antibodies). The label is then developed and quantitated using an image analysis system. The resulting quantitated polypeptide levels can be correlated with the aggressiveness of that cancer. Although samples can be processed individually, samples from different tissues or from a population of different patients can be processed simultaneously. Such processing methods include, without limitation, tissue microarrays, as described by Kononen et al., (1998) *Nature Med.* 4: 844-847.

Suitable antibodies for ELISA-, immunohistochemistry- and immunofluorescence-based methods can be obtained using standard techniques. In addition, commercially available antibodies to polypeptides associated with cancer aggressiveness can be used.

Based upon the various methods of measuring described above and known in the art, the hormone receptor status such as progesterone receptor and estrogen receptor may be determined. For example, using immunohistochemistry and measuring nuclear reactivity of estrogen receptor and/or the progesterone receptor, the percentage of immunoreactive cells expressing estrogen receptor and/or the progesterone receptor recorded as the percentage of immunoreactive cells over at least 2,000 neoplastic cells may be determined. Breast cancer tissue is characterized as having a low hormone receptor status if greater than or equal to about 1% to about 10% of the cells of the breast cancer tissue express the estrogen receptor and/or the progesterone receptor. Breast cancer tissues is characterized as not expressing or negative for a hormone receptor such as estrogen receptor and/or the progesterone receptor if less than about 1% of the cells of the breast cancer tissue express the hormone receptor. In some embodiments, less than about any of 0.1%, 0.2%, 0.3%, 0.4%, 0.5%, 0.6%, 0.7%, 0.8%, or 0.9% of the cells of the breast cancer tissue express a hormone receptor such as estrogen receptor or the progesterone receptor. In some embodiments, less than about any of 0.1%, 0.2%, 0.3%, 0.4%, 0.5%, 0.6%, 0.7%, 0.8%, or 0.9% of the cells of the breast cancer tissue express the estrogen receptor and the progesterone receptor. In some embodiments, 0% of the cells of the breast cancer tissue express a hormone receptor such as estrogen receptor or the progesterone receptor. In some embodiments, 0% of the cells of the breast cancer tissue express the estrogen receptor and the progesterone receptor.

Combination Therapy with Chemotherapeutic Agent

The present invention provides methods of treating breast cancer based on hormone receptor status (e.g., not expressing the estrogen receptor and/or progesterone receptor) in an individual, comprising administering to the individual: a) an effective amount of a composition comprising nanoparticles comprising a taxane and a carrier protein (such as albumin); and b) an effective amount of at least one other chemotherapeutic agent. In some embodiments, the taxane is any of (and in come embodiments consisting essentially of) paclitaxel, docetaxel, and ortataxel. In some embodiments, the nanoparticle composition comprises Abraxane®. In some embodiments, the chemotherapeutic agent is any of (and in some embodiments selected from the group consisting of) antimetabolite agents (including nucleoside analogs), platinum-based agents, alkylating agents, tyrosine kinase inhibitors, anthracycline antibiotics, vinca alkloids, proteasonle inhibitors, macrolides, and topoisomerase inhibitors.

In some embodiments, the hormone receptor status is low for one or more hormone receptors such as the estrogen receptor or the progesterone receptor. In some embodiments, the individual is likely more responsive to the therapy if hormone receptor status is low for both estrogen receptor and progesterone receptor. In some embodiments, the hormone receptor status does not express (i.e., is negative for) one or more hormone receptors such as the estrogen receptor (ER) or the progesterone receptor (PgR). In some embodiments, the hormone receptor status of the breast cancer tissue does not express (i.e., is negative for) both the estrogen receptor (ER) and the progesterone receptor (PgR). In some embodiments, the individual is likely more responsive to the therapy if hormone receptor status is negative for both estrogen receptor and progesterone receptor. In some embodiments, the individual expresses (i.e., is positive for) either the estrogen receptor or the progesterone receptor. In some embodiments, the individual expresses (i.e., is positive for) both the estrogen receptor and the progesterone receptor. In some embodiments, the individual is likely less responsive to therapy if the hormone receptor status is positive for the estrogen receptor and/or the progesterone receptor.

In some embodiments, the breast cancer tissue further expresses HER2 (HER2+). In some embodiments, the breast cancer tissue further does not express HER2 (HER2−).

In some embodiments, the method comprises administering to the individual: a) an effective amount of a composition comprising nanoparticles comprising paclitaxel and an albumin; and b) an effective amount of at least one other chemotherapeutic agent. In some embodiments, the paclitaxel/albumin nanoparticles have an average diameter of no greater than about 200 nm. In some embodiments, the paclitaxel; albumin nanoparticle composition is substantially free (such as free) of surfactant (such as Cremophor). In some embodiments, the weight ratio of the albumin to paclitaxel in the composition is about 18:1 or less, such as about 9:1 or less. In some embodiments, the paclitaxel is coated with albumin. In some embodiments, the paclitaxel; albumin. nanoparticles have an average diameter of no greater than about 200 nm and the paclitaxel/albumin composition is substantially free (such as free) of surfactant (such as Cremophor). In some embodiments, the paclitaxel/albumin nanoparticles have an average diameter of no greater than about 200 nm and the paclitaxel is coated with albumin. In some embodiments, the nanoparticle composition is Abraxane®.

In some embodiments, the invention provides a method of treating breast cancer based on hormone receptor status (e.g., not expressing the estrogen receptor and/or progesterone receptor) in an individual comprising administering to the individual a) an effective amount of Abraxane®, and b) an effective amount of at least one other chemotherapeutic agent. Preferred drug combinations for sequential or co-administration or simultaneous administration with Abraxane® are those which show enhanced antiproliferative activity when compared with the single components alone, especially combinations that that lead to regression of proliferative tissues and/or cure from proliferative diseases.

The chemotherapeutic agents described herein can be the agents themselves, pharmaceutically acceptable salts thereof, and pharmaceutically acceptable esters thereof, as well as stereoisomers, enantiomers, racemic mixtures, and the like. The chemotherapeutic agent or agents as described can be administered as well as a pharmaceutical composition containing the agent(s), wherein the pharmaceutical composition comprises a pharmaceutically acceptable carrier vehicle, or the like.

The chemotherapeutic agent may be present in a nanoparticle composition. For example, in some embodiments, there is provided a method of treating breast cancer based on hormone receptor status (e.g., not expressing the estrogen receptor and/or progesterone receptor) in an individual, comprising administering to the individual: a) an effective amount of a composition comprising nanoparticles comprising a taxane and a carrier protein (such as albumin); and b) an effective amount of a composition comprising nanoparticles comprising at least one other chemotherapeutic agent and a carrier protein (such as albumin). In some embodiments, the method comprises administering to the individual: a) an effective amount of a composition comprising nanoparticles comprising paclitaxel and an albumin (such as Abraxane®); and b) an effective amount of a composition comprising nanoparticles comprising at least one other chemotherapeutic agent and a carrier protein (such as albumin). In some embodiments, the chemotherapeutic agent is any of (and in some embodiments selected from the group consisting of) thiocoichicine or its derivatives (such as dimeric thiocolehicine, including for example nab-5404, nab-5800, and nab-5801), rapamycin or its derivatives, and geldanamycin or its derivatives (such as 17-allyl amino geldanamycin (17-AAG)). In some embodiments, the chemotherapeutic agent is rapamycin. In some embodiments, the chemotherapeutic agent is 17-AAG.

An exemplary and non-limiting list of chemotherapeutic agents contemplated is provided herein. Suitable chemotherapeutic agents include, for example, vinca alkaloids, agents that disrupt microtubule formation (such as colchicines and its derivatives), anti-angiogenic agents, therapeutic antibodies, EGFR targeting agents, tyrosine kinase targeting agent (such as tyrosine kinase inhibitors), transitional metal complexes, proteasome inhibitors, antimetabolites (such as nucleoside analogs), alkylating agents, platinum-based agents, anthracycline antibiotics, topoisomerase inhibitors, macrolides, therapeutic antibodies, retinoids (such as all-trans retinoic acids or a derivatives thereof); geldanamycin or a derivative thereof (such as 17-AAG), and other standard chemotherapeutic agents well recognized in the art.

In some embodiments, the chemotherapeutic agent is any of (and in some embodiments selected from the group consisting of) adriamycin, colchicine, cyclophosphamide, actinomycin, bleomycin, duanorubicin, doxorubicin, epirubicin, mitomycin, methotrexate, mitoxantrone, fluorouracil, carboplatin, carmustine (BCNU), methyl-CCNU, cisplatin, etoposide, interferons, carnptothecin and derivatives thereof, phenesterine, taxanes and derivatives thereof (e.g., paclitaxel and derivatives thereof, taxotere and derivatives thereof, and the like), topetecan, vinblastine, vincristine, tamoxifen, piposulfan, nab-5404, nab-5800, nab-5801, Irinotecan, HKP, Ortataxel, gemcitabine, Herceptin®, vinorelbine, Doxil®, capecitabine, Alimta®, Avastin®, Velcade®, Tarceva®, Neulasta®, Lapatinib, Sorafenib, derivatives thereof, chemotherapeutic agents known in the art, and the like. In some embodiments, the chemotherapeutic agent is a composition comprising nanoparticles comprising a thio-colchicine derivative and a carrier protein (such as albumin).

In some embodiments, the chemotherapeutic agent is a antineoplastic agent including, but is not limited to, carboplatin, Navelbine® (vinorelbine), anthracycline (Doxil®), lapatinib (GW57016), Herceptin®, gemcitabine (Gemzar®), capecitabine (Xeloda®), Alimta®, cisplatin, 5-fluorouracil, epirubicin, cyclophosphamide, Avastin®, Velcade®, etc.

In some embodiments, the chemotherapeutic agent is an antagonist of other factors that are involved in tumor growth, such as EGFR, ErbB2 (also known as Herb), ErbB3, ErbB4, or TNF. Sometimes, it may be beneficial to also administer one or more cytokines to the individual. In some embodiments, the therapeutic agent is a growth inhibitory agent. Suitable dosages for the growth inhibitory agent are those presently used and may be lowered due to the combined action (synergy) of the growth inhibitory agent and the taxane.

In some embodiments, the chemotherapeutic agent is a chemotherapeutic agent other than an anti-VEGF antibody, a HER2 antibody, interferon, and an HGFβ antagonist.

Reference to a chemotherapeutic agent herein applies to the chemotherapeutic agent or its derivatives and accordingly the invention contemplates and includes either of these embodiments (agent; agent or derivative(s)). "Derivatives" or "analogs" of a chemotherapeutic agent or other chemical moiety include, but are not limited to, compounds that are structurally similar to the chemotherapeutic agent or moiety or are in the same general chemical class as the chemotherapeutic agent or moiety. In some embodiments, the derivative or analog of the chemotherapeutic agent or moiety retains similar chemical and/or physical property (including, for example, functionality) of the chemotherapeutic agent or moiety.

In some embodiments, the invention provides a method of treating breast cancer based on hormone receptor status (e.g., not expressing the estrogen receptor and/or progesterone receptor) in an individual, comprising administering to the individual a) an effective amount of a composition comprising nanoparticles comprising a taxane and a carrier protein (such as albumin), and b) an effective amount of a tyrosine kinase inhibitor. In some embodiments, the invention provides a method of treating breast cancer based on hormone receptor status (e.g., not expressing the estrogen receptor and/or progesterone receptor) in an individual, comprising administering to the individual a) an effective amount of a composition comprising nanoparticles comprising paclitaxel and an albumin (such as Abraxane®), and b) an effective amount of a tyrosine kinase inhibitor. Suitable tyrosine kinase inhibitors include, for example, imatinib (Gleevec®), gefitinib (Iressa®), Tarceva, Sutent® (sunitinib malate), and Lapatinib. In some embodiments, the tyrosine kinase inhibitor is lapatinib. In some embodiments, the tyrosine kinase inhibitor is Tarceva. Tarceva is a small molecule human epidermal growth factor type 1/epidermal growth factor receptor (HER1/EGFR) inhibitor which demonstrated, in a Phase III clinical trial, an increased survival in advanced non-small cell lung cancer (NSCLC) individuals. In some embodiments, the method is for treatment of breast cancer, including treatment of metastatic breast cancer and treatment of breast cancer in a neoadjuvant setting. In some embodiments, the method is for treatment of advanced solid tumor. In some embodiments, there is provided a method to inhibit the proliferation of EGFR expressing tumors in a mammal comprising administering to a mammal infected with such tumors Abraxane® and gefitinib, wherein the gefitinib is administered by pulse-dosing.

In some embodiments, the invention provides a method of treating breast cancer based on honuone receptor status (e.g., not expressing the estrogen receptor and/or progesterone receptor) in an individual, comprising administering to the individual a) an effective amount of a composition comprising nanoparticles comprising a taxane and a carrier protein (such as albumin), and b) an effective amount of an antimetabolite agent (such as a nucleoside analog, including for example purine analogs and pyrimidine analogs). In some embodiments, the invention provides a method of treating breast cancer based on hormone receptor status (e.g., not expressing the estrogen receptor and/or progesterone receptor) in an individual, comprising administering to the individual a) an effective amount of a composition comprising nanoparticles comprising paclitaxel and an albumin (such as Abraxane®), and b) an effective amount of an antimetabolite agent. An "antimetabolic agent" is an agent which is structurally similar to a metabolite, but cannot be used by the body in a productive manner, Many antimetabolite agents interfere with production of nucleic acids, RNA and DNA. For example, the antimetabolite can be a nucleoside analog, which includes, but is not limited to, azacitidine, azathioprine, capecitabine (Xeloda®), cytarabine, cladribine, cytosine arabinoside (ara-C, cytosar), doxifluridine, fluorouracil (such as 5-fluorouracil), UFT, hydoxyurea, gemcitabine, mercaptopurine, methotrexate, thioguanine (such as 6-thioguanine). Other anti-metabolites include, for example, L-asparaginase (ELspa), decarbazine (DTIC), 2-deoxy-D-glucose, and procarbazine (matulane). In some embodiments, the nucleoside analog is any of (and in some embodiments selected from the group consisting of) gemcitabine, fluorouracil, and capecitabine. In some embodiments, the method is for treatment of metastatic breast cancer or locally advanced breast cancer. In some embodiments, the method is for first line treatment of metastatic breast cancer. In some embodiments, the method is for treatment of breast cancer in a neoadjuvant setting.

In some embodiments, the invention provides a method of treating breast cancer based on hormone receptor status (e.g., not expressing the estrogen receptor and/or progesterone receptor) in an individual, comprising administering to the individual a) an effective amount of a composition comprising nanoparticles comprising a taxane and a carrier protein (such as albumin), and b) an effective amount of an alkylating agent. In some embodiments, the invention provides a method of treating breast cancer based on hormone receptor status (e.g., not expressing the estrogen receptor and/or progesterone receptor) in an individual, comprising administering to the individual a) an effective amount of a composition comprising nanoparticles comprising paclitaxel and an albumin (such as Abraxane®), and b) an effective amount of an alkylating agent. Suitable alkylating agents include, but are not limited to, cyclophosphamide (Cytoxan), mechlorethamine, chlorambucil, melphalan, carmustine (BCNU), thiotepa, busulfan, alkyl sulphonates, ethylene imines, nitrogen mustard analogs, estramustine sodium phosphate, ifosfamide, nitrosoureas, lomustine, and streptozocin. In some embodiments, the alkylating agent is cyclophosphamide. In some embodiments, the cyclophosphamide is administered prior to the administration of the nanoparticle composition. In some embodiments, the method is for treatment of an early stage breast cancer. In some embodiments, the method is for treatment of a breast cancer in an adjuvant or a neoadjuvant setting.

In some embodiments, the invention provides a method of treating breast cancer based on hormone receptor status (e.g., not expressing the estrogen receptor and/or progesterone receptor) in an individual, comprising administering to the individual a) an effective amount of a composition comprising nanoparticles comprising a taxane and a carrier protein (such as albumin), and b) an effective amount of a platinum-based agent. In some embodiments, the invention provides a method of treating breast cancer based on hormone receptor status (e.g., not expressing the estrogen receptor and/or progesterone receptor) in an individual, comprising administering to the individual a) an effective amount of a composition comprising nanoparticles comprising paclitaxel and an albumin (such as Abraxane®), and b) an effective amount of a platinum-based agent. Suitable platinum-based agents include, but are not limited to, carboplatin, cisplatin, and oxaliplatin. In some embodiments, the platinum-based agent is carboplatin. In some embodiments, the method is for treatment of breast cancer (HER2 positive or HER2 negative, including metastatic breast cancer and advanced breast cancer).

In some embodiments, the invention provides a method of treating breast cancer based on hormone receptor status (e.g., not expressing the estrogen receptor and/or progesterone receptor) in an individual, comprising administering to the individual a) an effective amount of a composition comprising nanoparticles comprising a taxane and a carrier protein (such as albumin), and b) an effective amount of an anthracycline antibiotic. In some embodiments, the invention provides a method of treating a proliferative disease (such as cancer) in an individual, comprising administering to the individual a) an effective amount of a composition comprising nanoparticles comprising paclitaxel and an albumin (such as Abraxane®) and a carrier protein (such as albumin), and b) an effective amount of an anthracycline antibiotic. Suitable anthracycline antibiotic include, but are not limited to, Doxil®, actinomycin, dactinomycin, daunorubicin (daunomycin), doxorubicin (adriamycin), epirubicin, idarubicin, mitoxantrone, valrubicin. In some embodiments, the anthracycline is any of (and in some embodiments selected from the group consisting of) Doxil®, epirubicin, and doxorubicin. In some embodiments, the method is for treatment of an early stage breast cancer. In some embodiments, the method is for treatment of a breast cancer in an adjuvant or a neoadjuvant setting.

In some embodiments, the invention provides a method of treating breast cancer based on hormone receptor status (e.g., not expressing the estrogen receptor and/or progesterone receptor) in an individual, comprising administering to the individual a) an effective amount of a composition comprising nanoparticles comprising a taxane and a carrier protein (such as albumin), and b) an effective amount of a vinca alkaloid. In some embodiments, the invention provides a method of treating breast cancer based on hormone receptor status (e.g., not expressing the estrogen receptor and/or progesterone receptor) in an individual, comprising administering to the individual a) an effective amount of a composition comprising nanoparticles comprising paclitaxel and an albumin (such as Abraxane®) and a carrier protein (such as albumin), and b) an effective amount of a vinca alkaloid. Suitable vinca alkaloids include, for example, vinblastine, vincristine, vindesine, vinorelbine (Navelbine®), and VP-16. In some embodiments, the vinca alkaloid is vinorelbine (Navelbine®). In some embodiments, the method is for treatment of stage IV breast cancer.

In some embodiments, the invention provides a method of treating breast cancer based on hormone receptor status (e.g., not expressing the estrogen receptor and/or progesterone receptor) in an individual, comprising administering to the individual a) an effective amount of a composition comprising nanoparticles comprising a taxane and a carrier protein (such as albumin), and b) an effective amount of a macrolide. In some embodiments, the invention provides a method of treating breast cancer based on hormone receptor status (e.g., not expressing the estrogen receptor and/or progesterone receptor) in an individual, comprising administering to the individual a) an effective amount of a composition comprising nanoparticles comprising paclitaxel and an albumin (such as Abraxane®) and a carrier protein (such as albumin), and b) an effective amount of a macrolide. Suitable macrolides include, for example, rapamycin, carbomycin, and erythromycin. In some embodiments, the macrolide is rapamycin or a derivative thereof. In some embodiments, the method is for treatment of a solid tumor.

In some embodiments, the invention provides a method of treating breast cancer based on hormone receptor status (e.g., not expressing the estrogen receptor and/or progesterone receptor) in an individual, comprising administering to the individual a) an effective amount of a composition comprising nanoparticles comprising a taxane and a carrier protein (such as albumin), and b) an effective amount of a topoisomerase inhibitor. In some embodiments, the invention provides a method of treating breast cancer based on hormone receptor status (e.g., not expressing the estrogen receptor and/or progesterone receptor) in an individual, comprising administering to the individual a) an effective amount of a composition comprising nanoparticles comprising paclitaxel and an albumin (such as Abraxane®) and a carrier protein (such as albumin), and b) an effective amount of a topoisomerase inhibitor. In some embodiments, the chemotherapeutic agent is a topoisomerase inhibitor, including, for example, inhibitor of topoisomerase I and topoisomerase II. Exemplary inhibitors of topoisomerase I include, but are not limited to, camptothecin, such as irinotecan and topotecan. Exemplary inhibitors of topoisomerase II include, but are not limited to, amsacrine, etoposide, etoposide phosphate, and teniposide.

In some embodiments, the invention provides a method of treating breast cancer based on hormone receptor status (e.g., not expressing the estrogen receptor and/or progesterone receptor) in an individual, comprising administering to the individual a) an effective amount of a composition comprising nanoparticles comprising a taxane and a carrier protein (such as albumin), and b) an effective amount of an antiangiogenic agent. In some embodiments, the invention provides a method of treating breast cancer based on hormone receptor status (e.g., not expressing the estrogen receptor and/or progesterone receptor) in an individual, comprising administering to the individual a) an effective amount of a composition comprising nanoparticles comprising paclitaxel and an albumin (such as Abraxane®) and a carrier protein (such as albumin), and b) an effective amount of an antiangiogenic agent. In some embodiments, the method is for treatment of metastatic breast cancer and breast cancer in an adjuvant setting or a neoadjuvant setting.

Many anti-angiogenic agents have been identified and are known in the art, including those listed by Carmeliet and Jain (2000). The anti-angiogenic agent can be naturally occurring or non-naturally occurring. In some embodiments, the chemotherapeutic agent is a synthetic antiangiogenic peptide. For example, it has been previously reported that the antiangiogenic activity of small synthetic pro-apoptic peptides comprise two functional domains, one targeting the CD13 receptors (aminopeptidase N) on tumor microvessels and the other disrupting the mitochondrial membrane following internalization. *Nat Med* (1999) 5(9): 1032-8. A second generation dimeric peptide, CNGRC-GG-d(KLAK-LAK)2, named HKP (Hunter Killer Peptide) was found to have improved antitumor activity. Accordingly, in some embodiments, the antiangiogenic peptide is HKP. In some embodiments, the antiangiogenic agent is other than an anti-VEGF antibody (such as Avastin®).

In some embodiments, the invention provides a method of treating breast cancer based on hormone receptor status (e.g., not expressing the estrogen receptor and/or progesterone receptor) in an individual, comprising administering to the individual a) an effective amount of a composition comprising nanoparticles comprising a taxane and a carrier protein (such as albumin), and b) an effective amount of a proteasome inhibitor, such as bortezomib (Velcade). In some embodiments, the invention provides a method of treating breast cancer based on hormone receptor status (e.g., not expressing the estrogen receptor and/or progesterone receptor) in an individual, comprising administering to the individual a) an effective amount of a composition comprising nanoparticles comprising paclitaxel and an albumin (such as Abraxane®) and a carrier protein (such as albumin), and b) an effective amount of a proteasome inhibitor such as bortezomib (Velcade®).

In some embodiments, the invention provides a method of treating breast cancer based on hormone receptor status (e.g., not expressing the estrogen receptor and/or progesterone receptor) in an individual, comprising administering to the individual a) an effective amount of a composition comprising nanoparticles comprising a taxane and a carrier protein (such as albumin), and b) an effective amount of a therapeutic antibody. In some embodiments, the invention provides a method of treating breast cancer based on hormone receptor status (e.g., not expressing the estrogen receptor and/or progesterone receptor) in an individual, comprising administering to the individual a) an effective amount of a composition comprising nanoparticles comprising paclitaxel and an albumin (such as Abraxane®) and a carrier protein (such as albumin), and b) an effective amount of a therapeutic antibody. Suitable therapeutic antibodies include, but are not limited to, anti-VEGF antibody (such as Avastin® (bevacizumab)), anti-HER2 antibody (such as Herceptin® (trastuzumab)), Erbitux® (cetuximab), Campath (alemtuzumab), Myelotarg (gemtuzumab), Zevalin (ibritumomab tiuextan, Rituxan (rituximab), and Bexxar (tositumomab). In some embodiments, the chemotherapeutic agent is Erbitux® (cetuximab). In some embodiments, the chemotherapeutic agent is a therapeutic antibody other than an antibody against VEGF or HER2. In some embodiments, the method is for treatment of HER2 positive breast cancer, including treatment of advanced breast cancer, treatment of metastatic cancer, treatment of breast cancer in an adjuvant setting, and treatment of breast cancer in a neoadjuvant setting. In some embodiments, the method is for treatment of any of metastatic breast cancer and breast cancer in an adjuvant setting or a neoadjuvant setting. For example, in some embodiments, there is provided a method for treatment of HER2 positive metastatic breast cancer in an individual, comprising administering to the individual 125 mg/m$^2$ paclitaxel/albumin nanoparticle composition (such as Abraxane®) weekly for three weeks with the fourth week off, concurrent with the administration of Herceptin®.

In some embodiments, there is provided a method of treating breast cancer based on hormone receptor status (e.g., not expressing the estrogen receptor and/or progesterone receptor) in an individual, comprising administering to the individual: a) an effective amount of a composition comprising nanoparticles comprising taxane and a carrier protein, and b) an effective amount of an anti-VEGF antibody. In some embodiments, the effective amounts of the taxane nanoparticle composition and the anti-VEGF antibody synergistically inhibit cell proliferation (such as tumor cell growth). In some embodiments, at least about 10% (including for example at least about any of 20%, 30%, 40%, 60%, 70%, 80%, 90%, or 100%) cell proliferation is inhibited. In some embodiments, the taxane is paclitaxel. In some embodiments, the anti-VEGF antibody is bevacizumab (such as Avastin®). In some embodiments, the taxane is paclitaxel and the anti-VEGF antibody is bevacizumab (such as Avastin®). In some embodiments, the taxane in the nanoparticle in the composition is administered by intravenous administration. In some embodiments, the anti-VEGF antibody is administered by intravenous administration. In some embodiments, both the taxane in the nanoparticle composition and the anti-VEGF antibody are administered by intravenous administration.

In some embodiments, there is provided a method of inhibiting breast cancer tumor metastasis based on hormone receptor status (e.g., not expressing the estrogen receptor and/or progesterone receptor) in an individual, comprising administering to the individual: a) an effective amount of a composition comprising nanoparticles comprising taxane and a carrier protein, and b) an effective amount of an anti-VEGF antibody. In some embodiments, the effective amounts of the taxane nanoparticle composition and the anti-VEGF antibody synergistically inhibit tumor metastasis. In some embodiments, at least about 10% (including for example at least about any of 20%, 30%, 40%, 60%, 70%, 80%, 90%, or 100%) metastasis is inhibited. In some embodiments, method of inhibiting metastasis to lymph node is provided. In some embodiments, method of inhibiting metastasis to the lung is provided. In some embodiments, the taxane is paclitaxel. In some embodiments, the anti-VEGF antibody is bevacizumab (such as Avastin®). In some embodiments, the taxane is paclitaxel and the anti-VEGF antibody is bevacizumab (such as Avastin®). In some embodiments, the taxane in the nanoparticle in the composition is administered by intravenous administration. In some embodiments, the anti-VEGF antibody is administered by intravenous administration. In some embodiments, both the taxane in the nanoparticle composition and the anti-VEGF antibody are administered by intravenous administration.

Suitable dosages for anti-VEGF antibody include, for example, about 1 mg/kg to about 20 mg/kg, including for example about 1 mg/kg to about 15 mg/kg (such as about any of 2, 4, 6, 8, 10, or 12 mg/kg). In some embodiments, the dosage of the anti-VEGF antibody is about 40 mg/m$^2$ to about 600 mg/m$^2$, including for example about 100 mg/m$^2$ to about 400 mg/m$^2$ (such as about any of 100, 200, or 300 mg/m$^2$). In some embodiments, the anti-V EGF antibody is bevacizumab (such as Avastin®).

Suitable combinations of the amounts of taxane in a nanoparticle composition and the anti-VEGF antibody include, for example, about 1 mg/kg to about 20 mg/kg (such as about any of 2, 5, 10, or 15 mg/kg) taxane in a nanoparticle composition and about 1 mg/kg to about 20 mg/kg (such as about any of 2, 4, 6, 8, 10, 12, 14, 16, or 18 mg/kg) anti-VEGF antibody; about 3 mg/m$^2$ to about 400 mg/m$^2$ (such as about any of 6, 10, 15, 30, 45, 60, 100, 150, 200, or 300 mg/m$^2$) taxane in a nanoparticle composition and 40 mg/m$^2$ to about 600 mg/m$^2$, including for example about 100 mg/m$^2$ to about 400 mg/m$^2$ (such as about any of 100, 200, or 300 mg/m$^2$) anti-VEGF antibody; about 3 mg/m$^2$ to about 300 mg/m$^2$ (such as about any of 6, 10, 15, 30, 45, 60, 100, 150, 200, or 300 mg/m$^2$) taxane in a nanoparticle composition and about 1 mg/kg to about 20 mg/kg (such as about any of 2, 4, 6, 8, 10, 12, 14, 16, or 18 mg/kg) anti-VEGF antibody. In some embodiments, the method comprises administering to an individual at least about 200 mg/m$^2$ taxane in a nanoparticle composition and at least about any of 2, 4, 8, or 10 mg/kg anti-VEGF antibody.

In some embodiments of the method, the taxane nanoparticle composition and the anti-VEGF antibody are administered simultaneously to the individual. In some embodiments of the method, the administration of the nanoparticle composition and the chemotherapeutic agent are concurrent. One exemplary dosing regime for the combination therapy of taxane nanoparticle composition includes administration of 100 mg/m2-300 mg/m$^2$ (such as 200 mg/m$^2$) taxane in nanoparticle composition at least weekly (including for example every 1, 2, 3, 4, 5, or 6 days) concurrent with administration of 2 mg/kg-15 mg/kg (such as any of 4, 6, 8, 10 mg/kg or 15 mg/kg) anti-VEGF antibody every two weeks or more frequently (for example every week, twice every week, or three times a week).

In some embodiments, the taxane nanoparticle composition and the anti-VEGF antibody are administered sequentially to the individual. For example, in some embodiments, the taxane nanoparticle composition is administered for at least one (such as at least any of two, three, four, five, or six) cycles prior to the administration of the anti-VEGF antibody. This is then followed by the administration of an anti-VEGF antibody for at least once (such as twice) a week for at least about 3 (such as 4, 5, or 6) weeks. One exemplary dosing regime for the combination therapy of taxane nanoparticle composition (such as paclitaxel/albumin nanoparticle composition, for example Abraxane®) and anti-VEGF antibody (such as bevacizumab, for example Avastin®) includes administration of 10 mg/kg taxane in a nanoparticle composition daily for 5 days in two cycles separated by one week followed by administration of an anti-VEGF antibody at dosages of 2 mg/kg, 4 mg/kg, or 8 mg/kg twice a week for 6 weeks.

In some embodiments, two or more chemotherapeutic agents are administered in addition to the taxane in the nanoparticle composition. These two or more chemotherapeutic agents may (but not necessarily) belong to different classes of chemotherapeutic agents. Examples of these combinations are provided herein. Other combinations are also contemplated.

In some embodiments, there is provided a method of treating breast cancer based on hormone receptor status (e.g., not expressing the estrogen receptor and/or progesterone receptor) in an individual, comprising administering to the individual a) an effective amount of a composition comprising nanoparticles comprising a taxane and a carrier protein (such as albumin), b) an effective amount of an antimetabolite (such as a nucleoside analog, for example, gemcitabine), and c) an anthracycline antibiotic (such as epirubicin). In some embodiments, there is provided a method of treating breast cancer based on hormone receptor status (e.g., not expressing the estrogen receptor and/or progesterone receptor) in an individual, comprising administering to the individual a) an effective amount of a composition comprising nanoparticles comprising paclitaxel and an albumin (such as Abraxane®), b) an effective amount of an antimetabolite (such as a nucleoside analog, for example, gemcitabine), and c) an effective amount of an anthracycline antibiotic (such as epirubicin). In some embodiments, the method is for treatment of breast cancer in a neoadjuvant setting. For example, in some embodiments, there is provided a method of treating locally advanced/inflammatory cancer in an individual comprising administering to the individual 220 mg/m$^2$ paclitaxel/albumin nanoparticle composition (such as Abraxane®) every two weeks; 2000 mg/m$^2$ gemcitabine, every two weeks; and 50 mg/m² epirubicin, every two weeks. In some embodiments, there is provided a method of treating breast cancer in an individual in an adjuvant setting, comprising administering to the individual 175 mg/paclitaxel/albumin paclitaxel/albumin nanoparticle composition (such as Abraxane®) every two weeks, 2000 mg/m² gemcitabine, every two weeks, and 50 mg/m² epirubicin, every two weeks.

In some embodiments, there is provided a method of treating breast cancer based on hormone receptor status (e.g., not expressing the estrogen receptor and/or progesterone receptor) in an individual, comprising administering to the individual a) an effective amount of a composition comprising nanoparticles comprising a taxane and a carrier protein (such as albumin), b) an effective amount of a platinum-based agent (such as carboplatin), and c) a therapeutic antibody (such as ant-HER2 antibody (such as Herceptin®) and anti-VEGF antibody (such as Avastin®)). In some embodiments, there is provided a method of treating breast cancer based on hormone receptor status (e.g., not expressing the estrogen receptor and/or progesterone receptor) in an individual, comprising administering to the individual a) an effective amount of a composition comprising nanoparticles comprising paclitaxel and an albumin (such as Abraxane®), b) an effective amount of a platinum-based agent (such as carboplatin), and c) a therapeutic antibody (such as ant-HER2 antibody (such as Herceptin®) and anti-VEGF antibody (such as Avastin®)). In some embodiments, the method is for treatment of any of advanced breast cancer, metastatic breast cancer, and breast cancer in an adjuvant setting. In some embodiments, there is provided a method of treating metastatic cancer in an individual, comprising administering to the individual 75 mg/m² paclitaxel/albumin nanoparticle composition (such as Abraxane®) and carboplatin, AUC=2, wherein the administration is carried out weekly for three weeks with the fourth week off. In some embodiments, the method further comprises weekly administering about 2-4 mg/kg of Herceptin®.

In some embodiments, there is provided a method of treating breast cancer based on hormone receptor status (e.g., not expressing the estrogen receptor and/or progesterone receptor) in an individual, comprising administering to the individual a) an effective amount of a composition comprising nanoparticles comprising a taxane and a carrier protein (such as albumin), b) an effective amount of a platinum-based agent (such as carboplatin), and c) vinca alkaloid (such as Navelbine®). In some embodiments, there is provided a method of treating breast cancer based on hormone receptor status (e.g., not expressing the estrogen receptor and/or progesterone receptor) in an individual, comprising administering to the individual a) an effective amount of a composition comprising nanoparticles comprising paclitaxel and an albumin (such as Abraxane®), b) an effective amount of a platinum-based agent (such as carboplatin), and c) a vinca alkaloid (such as Navelbine®).

In some embodiments, the invention provides a method of treating breast cancer based on hormone receptor status (e.g., not expressing the estrogen receptor and/or progesterone receptor) in an individual, comprising administering to the individual a) an effective amount of a composition comprising nanoparticles comprising a taxane and a carrier protein (such as albumin), b) an effective amount of an alkylating agent (such as cyclophosphamide) and c) an anthracycline antibiotic (such as adriamycin). In some embodiments, the invention provides a method of treating a proliferative disease (such as cancer) in an individual, comprising administering to the individual a) an effective amount of a composition comprising nanoparticles comprising paclitaxel and an albumin, b) an effective amount of an alkylating agent (such as cyclophosphamide) and c) an anthracycline antibiotic (such as adriamycin). In some embodiments, the method is for treatment of an early stage breast cancer. In some embodiments, the method is for treatment of a breast cancer in an adjuvant or a neoadjuvant setting. For example, in some embodiments, there is provided a method of treating an early stage breast cancer in an individual, comprising administering 260 mg/m² paclitaxel/albumin nanoparticle composition (such as Abraxane®), 60 mg/m² adriamycin, and 600 mg/m² cyclophosphamide, wherein the administration is carried out once every two weeks.

Other embodiments are provided in Table 1. For example, in some embodiments, there is provided a method of treating advanced breast cancer in an individual, comprising administering to the individual a) an effective amount of a composition comprising nanoparticles comprising a paclitaxel and an albumin (such as Abraxane®), b) an effective amount of carboplatin. In some embodiments, the method further comprises administering an effective amount of Herceptin® to the individual. In some embodiments, there is provided a method of treating metastatic breast cancer in an individual, comprising administering to the individual a) an effective amount of a composition comprising nanoparticles comprising paclitaxel and an albumin (such as Abraxane®), b) an effective amount of gemcitabine. In some embodiments, there is provided a method of treating advanced non-small cell lung cancer in an individual, comprising administering to the individual a) an effective amount of a composition comprising nanoparticles comprising paclitaxel and an albumin (such as Abraxane®), b) an effective amount of carboplatin.

In some embodiments, there is provided a composition comprising nanoparticles comprising a taxane (such as paclitaxel, docetaxel, or ortataxel) and a carrier protein (such as albumin) and at least one other chemotherapeutic agent. The compositions described herein may comprise effective amounts of the taxane and the chemotherapeutic agent for the treatment of breast cancer based on hormone receptor status (e.g., not expressing the estrogen receptor and/or progesterone receptor). In some embodiments, the chemotherapeutic agent and the taxane are present in the composition at a predetermined ratio, such as the weight ratios described herein. In some embodiments, the invention provides a synergistic composition of an effective amount of a composition comprising nanoparticles comprising a taxane (such as paclitaxel, docetaxel, or ortataxel) and an effective amount of at least one other chemotherapeutic agent. In some embodiments, the other chemotherapeutic agent is an anti-VEGF antibody (such as bevacizumab, for example, Avastin®).

In some embodiments, the invention provides pharmaceutical compositions comprising nanoparticles comprising a taxane and a carrier protein (such as albumin) for use in the treatment of breast cancer based on hormone receptor status (e.g., not expressing the estrogen receptor and/or progesterone receptor), wherein said use comprises simultaneous and/or sequential administration of at least one other chemotherapeutic agent. In some embodiments, the invention provides a pharmaceutical composition comprising a chemotherapeutic agent for use in the treatment of breast cancer based on hormone receptor status (e.g., not expressing the estrogen receptor and/or progesterone receptor), wherein said use comprises simultaneous and/or sequential administration of a composition comprising nanoparticles comprising a taxane and a carrier protein (such as albumin). In some embodiments, the invention provides taxane-containing nanoparticle compositions and compositions comprising one other chemotherapeutic agent for simultaneous, and/or sequential use for treatment of breast cancer based on hormone receptor status (e.g., not expressing the estrogen receptor and/or progesterone receptor).

Modes of Administration

The composition comprising nanoparticles comprising taxane (also referred to as "nanoparticle composition") and the chemotherapeutic agent can be administered simultaneously (i.e., simultaneous administration) and/or sequentially (i.e., sequential administration) in the methods described above for treating breast cancer based on hormone receptor status (e.g., not expressing the estrogen receptor and/or progesterone receptor).

In some embodiments, the nanoparticle composition and the chemotherapeutic agent (including the specific chemotherapeutic agents described herein) are administered simultaneously. The term "simultaneous administration," as used herein, means that the nanoparticle composition and the chemotherapeutic agent are administered with a time separation of no more than about 15 minute(s), such as no more than about any of 10, 5, or 1 minutes. When the drugs are administered simultaneously, the drug in the nanoparticles and the chemotherapeutic agent may be contained in the same composition (e.g., a composition comprising both the nanoparticles and the chemotherapeutic agent) or in separate compositions (e.g., the nanoparticles are contained in one composition and the chemotherapeutic agent is contained in another composition). For example, the taxane and the chemotherapeutic agent may be present in a single composition containing at least two different nanoparticles, wherein some of the nanoparticles in the composition comprise the taxane and a carrier protein, and some of the other nanoparticles in the composition comprise the chemotherapeutic agent and a carrier protein. The invention contemplates and encompasses such compositions. In some embodiments, only the taxane is contained in nanoparticles. In some embodiments, simultaneous administration of the drug in the nanoparticle composition and the chemotherapeutic agent can be combined with supplemental doses of the taxane and/or the chemotherapeutic agent.

In some embodiments, the nanoparticle composition and the chemotherapeutic agent are administered sequentially. The term "sequential administration" as used herein means that the drug in the nanoparticle composition and the chemotherapeutic agent are administered with a time separation of more than about 15 minutes, such as more than about any of 20, 30, 40, 50, 60 or more minutes. Either the nanoparticle composition or the chemotherapeutic agent may be administered first. The nanoparticle composition and the chemotherapeutic agent are contained in separate compositions, which may be contained in the same or different packages.

In some embodiments, the administration of the nanoparticle composition and the chemotherapeutic agent are concurrent, i.e., the administration period of the nanoparticle composition and that of the chemotherapeutic agent overlap with each other. In some embodiments, the administration of the nanoparticle composition and the chemotherapeutic agent are non-concurrent. For example, in some embodiments, the administration of the nanoparticle composition is terminated before the chemotherapeutic agent is administered. In some embodiments, the administration of the chemotherapeutic agent is terminated before the nanoparticle composition is administered. The time period between these two non-concurrent administrations can range from about two to eight weeks, such as about four weeks.

The dosing frequency of the drug-containing nanoparticle composition and the chemotherapeutic agent may be adjusted over the course of the treatment, based on the judgment of the administering physician. When administered separately, the drug-containing nanoparticle composition and the chemotherapeutic agent can be administered at different dosing frequency or intervals. For example, the drug-containing nanoparticle composition can be administered weekly, while a chemotherapeutic agent can be administered more or less frequently. In some embodiments, sustained continuous release formulation of the drug-containing nanoparticle and/or chemotherapeutic agent may be used. Various formulations and devices for achieving sustained release are known in the art.

The nanoparticle composition and the chemotherapeutic agent can be administered using the same route of administration or different routes of administration. In some embodiments (for both simultaneous and sequential administrations), the taxane in the nanoparticle composition and the chemotherapeutic agent are administered at a predetermined ratio. For example, in some embodiments, the ratio by weight of the taxane in the nanoparticle composition and the chemotherapeutic agent is about 1 to 1. In some embodiments, the weight ratio may be between about 0.001 to about 1 and about 1000 to about 1, or between about 0.01 to about 1 and 100 to about 1. In some embodiments, the ratio by weight of the taxane in the nanoparticle composition and the chemotherapeutic agent is less than about any of 100:1, 50:1, 30:1, 10:1, 9:1, 8:1, 7:1, 6:1, 5:1, 4:1, 3:1, 2:1, and 1:1 In some embodiments, the ratio by weight of the taxane in the nanoparticle composition and the chemotherapeutic agent is more than about any of 1:1, 2:1, 3:1, 4:1, 5:1, 6:1, 7:1, 8:1, 9:1, 30:1, 50:1, 100:1. Other ratios are contemplated.

The doses required for the taxane and/or the chemotherapeutic agent may (but not necessarily) be lower than what is normally required when each agent is administered alone. Thus, in some embodiments, a subtherapeutic amount of the drug in the nanoparticle composition and/or the chemotherapeutic agent are administered. "Subtherapeutic amount" or "subtherapeutic level" refer to an amount that is less than the therapeutic amount, that is, less than the amount normally used when the drug in the nanoparticle composition and/or the chemotherapeutic agent are administered alone. The reduction may be reflected in terms of the amount administered at a given administration and/or the amount administered over a given period of time (reduced frequency).

In some embodiments, enough chemotherapeutic agent is administered so as to allow reduction of the normal dose of the drug in the nanoparticle composition required to effect the same degree of treatment by at least about any of 5%, 10%, 20%, 30%, 50%, 60%, 70%, 80%, 90%, or more. In some embodiments, enough drug in the nanoparticle composition is administered so as to allow reduction of the normal dose of the chemotherapeutic agent required to affect the same degree of treatment by at least about any of 5%, 10%, 20%, 30%, 50%, 60%, 70%, 80%, 90%, or more.

In some embodiments, the dose of both the taxane in the nanoparticle composition and the chemotherapeutic agent are reduced as compared to the corresponding normal dose of each when administered alone. In some embodiments, both the taxane in the nanoparticle composition and the chemotherapeutic agent are administered at a subtherapeutic, i.e., reduced, level. In some embodiments, the dose of the nanoparticle composition and/or the chemotherapeutic agent is substantially less than the established maximum toxic dose (MTD). For example, the dose of the nanoparticle composition and/or the chemotherapeutic agent is less than about 50%, 40%, 30%, 20%, or 10% of the MTD.

A combination of the administration configurations described herein can be used. The combination therapy methods described herein may be performed alone or in conjunction with another therapy, such as surgery, radiation, chemotherapy, immunotherapy, gene therapy, and the like. Additionally, a person having a greater risk of developing the proliferative disease may receive treatments to inhibit or and/or delay the development of the disease.

As will be understood by those of ordinary skill in the art, the appropriate doses of chemotherapeutic agents will be approximately those already employed in clinical therapies wherein the chemotherapeutic agent are administered alone or in combination with other chemotherapeutic agents. Variation in dosage will likely occur depending on the condition being treated. As described above, in some embodiments, the chemotherapeutic agents may be administered at a reduced level.

The nanoparticle compositions described herein can be administered to an individual (such as human) via various routes, such as parenterally, including intravenous, intra-arterial, intraperitoneal, intrapulmonary, oral, inhalation, intravesicular, intramuscular, intra-tracheal, subcutaneous, intraocular, intrathecal, or transdermal. For example, the nanoparticle composition can be administered by inhalation to treat conditions of the respiratory tract. The composition can be used to treat respiratory conditions such as pulmonary fibrosis, broncheolitis obliterans, lung cancer, bronchoalveolar carcinoma, and the like. In some embodiments, the nanoparticle composition is administrated intravenously. In some embodiments, the nanoparticle composition is administered orally.

The dosing frequency of the administration of the nanoparticle composition depends on the nature of the combination therapy and the particular disease being treated. An exemplary dosing frequency include, but is not limited to, weekly without break; weekly, three out of four weeks; once every three weeks; once every two weeks; weekly, two out of three weeks. See also Table 1.

The dose of the taxane in the nanoparticle composition will vary with the nature of the combination therapy and the particular disease being treated. The dose should be sufficient to effect a desirable response, such as a therapeutic or prophylactic response against a particular disease. An exemplary dose of the taxane (in some embodiments paclitaxel) in the nanoparticle composition include, but is not limited to, about any of 50 mg/m$^2$, 60 mg/m$^2$. 75 mg/m$^2$, 80 mg/m$^2$, 90 mg/m$^2$, 100 mg/m$^2$; 120 mg/m$^2$; 160 mg/m$^2$, 175 mg/m$^2$, 200 mg/m$^2$, 210 mg/m$^2$, 220 mg/m$^2$, 260 mg/m$^2$, and 300 mg/m$^2$. For example, the dosage of paclitaxel in a nanoparticle composition can be in the range of 100-400 mg/m$^2$ when given on a 3 week schedule, or 50-250 mg/m$^2$ when given on a weekly schedule. See also Table 1.

Other exemplary dosing schedules for the administration of the nanoparticle composition (such as paclitaxel/albumin nanoparticle composition, for example Abraxane®) include, but are not limited to, 100 mg/m$^2$, weekly, without break; 75 mg/m$^2$ weekly, 3 out of four weeks; 100 mg/m$^2$, weekly, 3 out of 4 weeks; 125 mg/m$^2$, weekly, 3 out of 4 weeks; 125 mg/m$^2$, weekly, 2 out of 3 weeks; 130 mg/m$^2$, weekly, without break; 175 mg/m$^2$, once every 2 weeks; 260 mg/m$^2$, once every 2 weeks; 260 mg/m$^2$, once every 3 weeks; 180-300 mg/m$^2$, every three weeks; 60-175 mg/m$^2$, weekly, without break. In addition, the taxarie (alone or in combination therapy) can be administered by following a metronomic dosing regime described herein.

Exemplary dosing regimes for the combination therapy of nanoparticle composition (such as paclitaxel/albumin nanoparticle composition, for example Abraxane®) and other agents include, but are not limited to, 125 mg/m$^2$ weekly, two out of three weeks, plus 825 mg/m$^2$ Xeloda®, daily. The dose of the nanoparticle composition (such as paclitaxel/albumin nanoparticle composition, for example Abraxane®) and Xeloda® may vary depending on the particular disease or the patient being treated. The dose should be sufficient to effect a desirable response, such as a therapeutic or prophylactic response against a particular disease. An exemplary dose of the nanoparticle composition (in some embodiments paclitaxel/albumin nanoparticle composition, for example Abraxane®) in the combination therapy includes, but is not limited to, about any of 100 mg/m$^2$, 125 mg/m$^2$, 200 mg/m$^2$, and 260 mg/m$^2$. For example, the dosage of paclitaxel in a nanoparticle composition can be in the range of 50-300 mg/m$^2$ when given on a weekly schedule, with or without breaks. An exemplary dose of Xeloda® in the combination therapy includes, but is not limited to, about any of 550 mg/m$^2$, 650 mg/m$^2$, 825 mg/m$^2$, 850 mg/m$^2$, 1000 mg/m$^2$ and 1250 mg/m$^2$. For example, the dosage of Xeloda® can be in the range of 500-2500 mg/m$^2$ when given on a daily schedule, with or without breaks.

Exemplary dosing regimes for the combination therapy of nanoparticle composition (such as paclitaxel/albumin nanoparticle composition, for example Abraxane®) and other agents include, but are not limited to, 260 mg/m$^2$ once every two weeks plus 60 mg/m$^2$ adriamycin and 600 mg/m$^2$ cyclophosphamide, once every two weeks; 220-340 mg/m$^2$ once every three weeks, plus carboplatin, AUC=6, once every three weeks; 100-150 mg/m$^2$ weekly, plus carboplatin, AUC=6, once every three weeks; 175 mg/m2 once every two weeks, plus 2000 mg/m$^2$ gemcitabine and 50 mg/m$^2$ epirubicin, once every two weeks; and 75 mg/m$^2$ weekly, three out of four weeks, plus carboplatin, AUC=2, weekly, three out of four weeks.

In some embodiments, the nanoparticle composition of the taxane and the chemotherapeutic agent is administered according to any of the dosing regimes described in Table 1.

In some embodiments, there is provided a method of treating breast cancer in an individual comprising administering to the individual: a) an effective amount of a composition comprising nanoparticles comprising a taxane (such as paclitaxel) and an albumin, and b) an effective amount of at least one other chemotherapeutic agent as provided in Rows 1 to 35 in Table 1. In some embodiments, the administration of the nanoparticle composition and the chemotherapeutic agent may be any of the dosing regimes as indicated in Rows 1 to 35 in Table 1. In some embodiments, there is provided a method of treating metastatic breast cancer in an individual comprising administering to the individual: a) an effective amount of a composition comprising nanoparticles comprising a taxane (such as paclitaxel) and an albumin, and b) an effective amount of at least one other chemotherapeutic agent as provided in Rows 2, 4-8, and 10-15 in Table 1. In some embodiments, the administration of the nanoparticle composition and the chemotherapeutic agent may be any of the dosing regimes as indicated in Rows 2, 4-8, and 10-15 in Table 1.

In some embodiments, there is provided a method of treating advanced breast cancer in an individual comprising administering to the individual: a) an effective amount of a composition comprising nanoparticles comprising a taxane (such as paclitaxel) and an albumin, and b) an effective amount of at least one other chemotherapeutic agent as provided in Rows 1 and 16 in Table 1. In some embodiments, the administration of the nanoparticle composition and the chemotherapeutic agent may be any of the dosing regimes as indicated in Rows 1 and 16 in Table 1. In some embodiments, there is provided a method of treating stage IV breast cancer in an individual comprising administering to the individual: a) an effective amount of a composition comprising nanoparticles comprising a taxane (such as paclitaxel) and an albumin, and b) an effective amount of at least one other chemotherapeutic agent as provided in Row 3 in Table 1. In some embodiments, the administration of the nanoparticle composition and the chemotherapeutic agent may be the dosing regime as indicated in Row 3 in Table 1.

In some embodiments, there is provided a method of treating breast cancer in an individual in an adjuvant setting comprising administering to the individual: a) an effective amount of a composition comprising nanoparticles comprising a taxane (such as paclitaxel) and an albumin, and b) an effective amount of at least one other chemotherapeutic agent as provided in Rows 18 to 24 in Table 1. In some embodiments, the administration of the nanoparticle composition and the chemotherapeutic agent may be any of the dosing regimes as indicated in Rows 18 to 24 in Table 1.

In some embodiments, there is provided a method of treating breast cancer in an individual in a neoadjuvant setting comprising administering to the individual: a) an effective amount of a composition comprising nanoparticles comprising a taxane (such as paclitaxel) and an albumin, and b) an effective amount of at least one other chemotherapeutic agent as provided in Rows 25 to 35 in Table 1. In some embodiments, the administration of the nanoparticle composition and the chemotherapeutic agent may be any of the dosing regimes as indicated in Rows 25 to 35 in Table 1.

In some embodiments, there is provided a method of treating solid tumor (including advanced solid tumor) in an individual comprising administering to the individual: a) an effective amount of a composition comprising nanoparticles comprising a taxane (such as paclitaxel) and an albumin, and b) an effective amount of at least one other chemotherapeutic agent as provided in Rows 36 to 39 in Table 1. In some embodiments, the administration of the nanoparticle composition and the chemotherapeutic agent may be any of the dosing regimes as indicated in Rows 36 to 39 in Table 1.

TABLE 1

| Row No. | Combination | Regime/Dosage | Study therapy type | Protocol title |
|---|---|---|---|---|
| 1. | ABX + Carboplatin + Herceptin ® | ABX: 100 mg/m$^2$ D1, 8, 15 q4wk × 6<br>Carbo: AUC = 2 D1, 8, 15 q4wk × 6<br>Herceptin ®: 4 mg/kg on wk 1, 2 mg/kg all subsequent weeks | Advanced HER2+ Breast Cancer | A phase II study of weekly dose-dense nanoparticle paclitaxel (ABI-007) carboplatin ™, with Herceptin ® as first or second-line therapy of advanced HER2+ breast cancer |
| 2. | ABX alone (+Herceptin ®) | ABX: 125 mg/m$^2$ qwk × 3/4 | Metastatic Breast Cancer | Phase II trial of weekly Abraxane ® monotherapy for 1st-line MBC (plus Herceptin ® in HER2+ pts) |
| 3. | ABX + Navelbine ® (±G-CSF) | L1: ABX: 80 mg/m<br>Nav: 15 mg/m$^2$<br>L2: ABX: 90 mg/m$^2$<br>Nav: 20 mg/m$^2$<br>L3: ABX: 100 mg/m$^2$<br>Nav: 22.5 mg/m$^2$<br>L4: ABX: 110 mg/m$^2$<br>Nav: 25 mg/m2<br>L5: ABX: 125 mg/m$^2$<br>Nav: 25 mg/m$^2$<br>qwk all levels | Stage IV Breast Cancer | Phase I-II study weekly ABX + Navelbine ®, with or without G-CSF, in stage IV breast cancer |
| 4. | ABX + Xeloda ® | ABX: 125 mg/m$^2$ qwk × 2/3<br>Xeloda ®: 825 mg/m$^2$ D1-14 q3wk | Metastatic Breast Cancer | Phase II 1st-line ABX + Xeloda ® MBC trial |
| 5. | ABX + Anthracycline | | Metastatic Breast Cancer | Phase I/II trial ABX plus Doxil ® for MBC plus limited PK |
| 6. | ABX + Gemcitabine | ABX: 125 mg/m$^2$<br>Gem: 1000 mg/m$^2$<br>qwk × 2/3 | Metastatic Breast Cancer | Randomized Phase II Trial of Weekly nab (nanoparticle albumin bound)-Paclitaxel (nab-paclitaxel) in Combination with Gemcitabine in Patients with HER2 Negative Metastatic Breast Cancer |
| 7. | ABX + Lapatinib | | Metastatic Breast Cancer | Phase I/II Abraxane ® + GW572016 |
| 8. | ABX + Lapatinib | ABX: 100 mg/m$^2$ qwk × 3/4<br>Lapatinib: starting at 1000 mg/d × 2 days | Metastatic Breast Cancer | Phase I dose escalation study of a 2 day oral lapatinib chemosensitization pulse given prior to |

TABLE 1-continued

| Row No. | Combination | Regime/Dosage | Study therapy type | Protocol title |
|---|---|---|---|---|
| | | | | weekly intravenous Abraxane ® in patients with advanced solid tumors |
| 9. | ABX + FEC (+Herceptin ®) | ABX: 220 mg/m2 q2wk × 6 followed by FEC: 4 cycles (+Herceptin ® for HER2+ pts) | Breast Cancer | Phase II preoperative trial of Abraxane ® followed by FEC (+Herceptin ® as appropriate) in breast cancer |
| 10. | ABX + Carboplatin + Avastin ® | ABX: 100 mg/m² qwk D1, 8, 15 Carbo: AUC = 2 qwk D1, 8, 15 Avastin ®: 10 mg/m² q2wk | Metastatic Breast Cancer (HER2−, ER−, PR−) | Phase II safety and tolerability study of Abraxane ®, Avastin ® and carboplatin in triple, negative metastatic breast cancer patients |
| 11. | ABX + Avastin ® | ABX: 130 mg/m² qwk + Avastin ® vs ABX: 260 mg/m² q2wk + Avastin ® vs ABX: 260 mg/m² q3wk + Avastin ® | Metastatic Breast Cancer | Three arm phase II trial in 1$^{st}$ line HER2− negative MBC patients |
| 12. | ABX + Avastin ® | ABX: 125 mg/m² qwk × 3/4 + Avastin ® | Metastatic Breast Cancer | Single arm study of Abraxane ® and Avastin ® in 1$^{st}$ line MBS |
| 13. | ABX + Avastin ® | ABX + Avastin ® qwk vs Taxol ® + Avastin ® qwk | Metastatic Breast Cancer | Randomized Phase III trial in 1$^{st}$ line and 2$^{nd}$ line MBC with biological correlates analysis |
| 14. | ABX + Xeloda ® + Lapatinib | | Metastatic Breast Cancer | Phase II Abraxane ® in combination with Xeloda ® and Lapatinib for metastatic breast cancer |
| 15. | ABX + Gemcitabine | ABX: 3000 mg/m² D1 q3wk Gem: 12.50 mg/m² D1, 8 q3wk | Metastatic Breast Cancer | Single arm Phase II study of Abraxane ® and gemcitabine for 1$^{st}$ line MBC |
| 16. | ABX + RAD001 | | Advanced Breast Cancer | Phase I/II study of Abraxane ® in combination with RAD001 in patients with advanced breast cancer |
| 17. | ABX + Sutent ® | | Breast Cancer | Phase I study of Abraxane ® in combination with Sutent ® |
| 18. | ABX + AC + G-CSF (+Herceptin ®) | AC + G-CSF q2wk × 4 followed by ABX: 260 mg/m² q2wk × 4 (+Herceptin ® for HER2+ pts) | Breast Cancer- Adjuvant | Abraxane ® in dose- dense adjuvant chemotherapy for early stage breast cancer |
| 19. | ABX + AC + G-CSF (+Herceptin ®) | Dose dense AC + G-CSF followed by ABX (+Herceptin ® for HER2+ pts) qwk | Breast Cancer- Adjuvant | Phase II pilot adjuvant trial of Abraxane ® in breast cancer |
| 20. | ABX + AC | AC followed by ABX: 260 mg/m² vs AC followed by Taxol ® Rx length 16 wks | Breast Cancer- Adjuvant | Adjuvant Dose dense Registrational Trial |
| 21. | ABX + AC (+G-CSF) | AC q2wk followed by ABX: 260 mg/m² + G-CSF q2wk Rx length 16 wks | Breast Cancer- Adjuvant | Phase II dose dense pilot adjuvant study of Abraxane ® in breast cancer |
| 22. | ABX + AC (+Avastin ®) | Dose dense AC followed by ABX (+Avastin ® in HER2+ pts) | Breast Cancer- Adjuvant | Pilot adjuvant breast cancer study |
| 23. | ABX + AC | AC followed by ABX q2wk or q3wk | Breast Cancer- Adjuvant | BIG study: Dose dense vs standard adjuvant chemotherapy |
| 24. | ABX (ABI-007) + AC + Neulasta ® | AC followed by ABX q2wk × 4 | Breast Cancer- Adjuvant | Phase II—Pilot Study Evaluating the Safety of a Dose-Dense Regime— |

TABLE 1-continued

| Row No. | Combination | Regime/Dosage | Study therapy type | Protocol title |
|---|---|---|---|---|
| | | | | AC × 4 => ABI-007 × 4 Q 2 WEEKS + Neulasta ®—Given as Adjuvant Chemotherapy of High-Risk Women with Early Breast Cancer |
| 25. | ABX + FEC (+Herceptin ®) | ABX: 100 mg/m² qwk × 12 followed by 5-FU: 500 mg/m² q3wk Epirubicin: 100 mg/m² (without Herceptin ®) or Epirubicin: 75 mg/m² (with Herceptin ® for HER2+ pts) Cyclophosphamide: 500 mg/m² q3wk | Locally Advanced Breast Cancer- Neoadjuvant | A Phase II Study of Neoadjuvant Chemotherapy with Sequential Weekly Nanoparticle Albumin Bound Paclitaxel (Abraxane ®) Followed by 5-Fluorouracil, Epirubicin, Cyclophosphamide (FEC) in Locally Advanced Breast Cancer |
| 26. | ABX + Gemcitabine + Epirubicin | Arm 1: Neoadjuvant: Gem: 2000 mg/m², ABX: 175 mg/m², Epi 50 mg/m² q2wk × 6 Arm 2: Adjuvant: Gem: 2000 mg/m², ABX: 220 mg/m² q2wk × 4 | Breast Cancer- Neoadjuvant | Phase II Trial of Dose Dense Neoadjuvant Gemcitabine, Epirubicin, ABI-007 (GEA) in Locally Advanced or Inflammatory Breast Cance |
| 27. | ABX + Herceptin ® | ABX: 260 mg/m² q2wk + Herceptin ® followed by Navelbine ® + Herceptin ® | Breast Cancer- Neoadjuvant | Phase II Multi-center study neoadjuvant. |
| 28. | ABX + Carboplatin (+Herceptin ®) + AC | TAC vs AC followed by ABX + carbo vs AC followed by ABX + carbo + Herceptin ® | Breast Cancer- Neoadjuvant | 3 arms Randomized dose dense phase II trial of neoadjuvant chemotherapy in patients with breast cancer |
| 29. | ABX + Capecitabine | ABX: 260 mg/m² q3wk × 4 Xeloda ® 850 mg/m² D1-14 q3wk × 4 | Breast Cancer- Neoadjuvant | Phase II neoadjuvant trial of Abraxane ® and capecitabine in locally advanced breast cancer |
| 30. | ABX + Carboplatin (+Avastin ®) | ABX qwk carbo qwk + Avastin ® in HER2+ pts | Breast Cancer- Neoadjuvant | Phase I/II trial of neoadjuvant chemotherapy (NCT) with weekly nanoparticle paclitaxel (ABI-007, Abraxane ®) in combination with carboplatin and Avastin ® in clinical stage I-III. |
| 31. | ABX + Carboplatin + Herceptin ® + Avastin ® | ABX: 100 mg/m² qwk × 3/4 Carbo: AUC = 5 + Herceptin ® + Avastin ® 4 week cycle × 6 | Breast Cancer- Neoadjuvant | Phase II study of weekly bevacizumab administered with weekly trastuzumab, ABI-007, and carboplatin as preoperative therapy in HER2-neu gene amplified breast cancer tumors |
| 32. | ABX + Lapatinib | ABX: 260 mg/m² q3wk Lapatinib: 1000 mg/day | Breast Cancer Neoadjuvant | Pilot neoadjuvant trial with combination of ABI-007 (Abraxane ®) and GW572016 (Lapatinib) |
| 33. | ABX + Capecitabine | ABX: 200 mg/m² q3wk × 4 Xeloda ®: 1000 mg/m² D1-14 q3wk × 4 | Breast Cancer- Neoadjuvant | Phase II neoadjuvant trial of Abraxane ® and capecitabine in locally advanced breast cancer |
| 34. | ABX ± Avastin ® + AC (+G-CSF) | ABX qwk ± Avastin ® followed by A qwk + C daily vs Taxol ® qwk ± Avastin ® followed by A qwk + C daily | Breast Cancer- Neoadjuvant | Phase III trial of paclitaxel vs Abraxane ® with or without Avastin ® in combination with doxorubicin and |

TABLE 1-continued

| Row No. | Combination | Regime/Dosage | Study therapy type | Protocol title |
|---|---|---|---|---|
| | | | | cyclophosphamide plus G-CSF |
| 35. | ABX + AC | ABX followed by AC | Breast Cancer-Neoadjuvant | Phase II neoadjuvant trial with gene expression analyses |
| 36. | ABX + Rapamycin | ABX: 100 mg/m² qwk Rapamycin: 5-40 mg dose escalation | Solid Tumors | Phase I Study of Rapamycin in Combination with Abraxatin ® in Advanced Solid Tumors |
| 37. | ABX + Satraplatin | | Solid Tumors | Phase I trial of Abraxane ® and Satraplatin |
| 38. | ABX + Gemcitabine | ABX: 180, 220, 260, 300, 340 mg/m² q3wk Gemcitabine: 1000 mg/m² D1 and D8 | Advanced Solid Tumors | Phase I Trial of Abraxane ® in combination with Gemcitabine |
| 39. | ABX + Gefitinib | ABX: 100 mg/m² qwk × 3/4 Gefitinib starting at 1000 mg/d × 2 | Advanced Solid Tumors | Phase I dose escalation study of gefitinib chemosensitization pulse given prior to weekly Abraxane ® |

As used in herein (for example in Table 1), ABX refers to Abraxane®; GW572016 refers to lapatinib; Xel refers to capecitabine or Xeloda®; bevacizumab is also known as Avastin®; trastuzurnab is also known as Herceptin®; pemtrexed is also known as Alimta®; cetuximab is also known as Erbitux®, gefitinib is also known as Iressa®; FEC refers to a combination of 5-fluorouracil, Epirubicin and Cyclophosphamide; AC refers to a combination of Adriamycin plus Cyclophosphamide; TAC refers to a FDA approved adjuvant breast cancer regime; RAD001 refers to a derivative of rapamycin.

As used herein (for example in Table 1), AUC refers to area under curve; q4wk refers to a dose every 4 weeks; q3wk refers to a dose every 3 weeks; q2wk refers to a dose every 2 weeks; qwk refers to a weekly dose; qwk×3/4 refers to a weekly dose for 3 weeks with the 4$^{th}$ week off; qwk×2/3 refers to a weekly dose for 2 weeks with the 3$^{rd}$ week off Combination Therapy with Radiation Therapy and Surgery In another aspect, the present invention provides a method of treating breast cancer based on hormone receptor status (e.g., not expressing the estrogen receptor and/or progesterone receptor) comprising a first therapy comprising administering a taxane (particularly nanoparticles comprising a taxane) and a carrier protein and a second therapy comprising radiation and/or surgery.

In some embodiments, the hormone receptor status is low for one or more hormone receptors such as the estrogen receptor or the progesterone receptor. In some embodiments, the individual is likely more responsive to the therapy if hormone receptor status is low for both estrogen receptor and progesterone receptor. In some embodiments, the hormone receptor status does not express (i.e., is negative for) one or more hormone receptors such as the estrogen receptor (ER) or the progesterone receptor (PgR). In some embodiments, the hormone receptor status of the breast cancer tissue does not express (i.e., is negative for) both the estrogen receptor (ER) and the progesterone receptor (PgR). In some embodiments, the individual is likely more responsive to the therapy if hormone receptor status is negative for both estrogen receptor and progesterone receptor. In some embodiments, the individual expresses (i.e., is positive for) either the estrogen receptor or the progesterone receptor. In some embodiments, the individual expresses (i.e., is positive for) both the estrogen receptor and the progesterone receptor. In some embodiments, the individual is likely less responsive to therapy if the hormone receptor status is positive for the estrogen receptor and/or the progesterone receptor.

In some embodiments, the breast cancer tissue further expresses HER2 (HER2+) some embodiments, the breast cancer tissue further does not express HER2 (HER2−).

In some embodiments, the method comprises: a) a first therapy comprising administering to the individual a composition comprising nanoparticles comprising an effective amount of a taxane and a carrier protein (such as albumin) and b) a second therapy comprising radiation therapy, surgery, or combinations thereof. In some embodiments, the taxane is coated with the carrier protein (such as albumin). In some embodiments, the second therapy is radiation therapy. In some embodiments, the second therapy is surgery.

In some embodiments, the method comprises a) a first therapy comprising administering to the individual a composition comprising nanoparticles comprising paclitaxel and an albumin; and b) a second therapy comprising radiation therapy, surgery, or combinations thereof. In some embodiments, the second therapy is radiation therapy. In some embodiments, the second therapy is surgery. In some embodiments, the paclitaxel/albumin nanoparticles have an average diameter of no greater than about 200 nm. In some embodiments, the paclitaxel/albumin nanoparticle composition is substantially free (such as free) of surfactant (such as Cremophor). In some embodiments, the weight ratio of the albumin to paclitaxel in the composition is about 18:1 or less, such as about 9:1 or less. In some embodiments, the paclitaxel is coated with albumin. In some embodiments, the paclitaxel/albumin nanoparticles have an average diameter of no greater than about 200 nm and the paclitaxel/albumin composition is substantially free (such as free) of surfactant (such as Cremophor). In some embodiments, the paclitaxel/albumin nanoparticles have an average diameter of no greater than about 200 nm and the paclitaxel is coated with albumin. In some embodiments, the nanoparticle composition is Abraxane®.

The administration of the nanoparticle composition may be prior to the radiation and/or surgery, after the radiation and/or surgery, or concurrent with the radiation and/or surgery. For example, the administration of the nanoparticle composition may precede or follow the radiation and/or surgery therapy by intervals ranging from minutes to weeks. In some embodiments, the time period between the first and the second therapy is such that the taxane and the radiation/surgery would still be able to exert an advantageously combined effect on the cell. For example, the taxane (such as paclitaxel) in the nanoparticle composition may be administered less than about any of 1, 3, 6, 9, 12, 18, 24, 48, 60, 72, 84, 96, 108, 120 hours prior to the radiation and/or surgery. In some embodiments, the nanoparticle composition is administered less than about 9 hours prior to the radiation and/surgery. In some embodiments, the nanoparticle composition is administered less than about any of 1, 2, 3, 4, 5, 6, 7, 8, 9, or 10 days prior to the radiation/surgery. In some embodiments, the taxane (such as paclitaxel) in the nanoparticle composition is administered less than about any of 1, 3, 6, 9, 12, 18, 24, 48, 60, 72, 84, 96, 108, or 120 hours after the radiation and/or surgery. In some embodiments, it may be desirable to extend the time period for treatment significantly, where several days to several weeks lapse between the two therapies.

Radiation contemplated herein includes, for example, γ-rays, X-rays (external beam), and the directed delivery of radioisotopes to tumor cells. Other forms of DNA damaging factors are also contemplated such as microwaves and UV irradiation are also contemplated. Radiation may be given in a single dose or in a series of small doses in a dose-fractionated schedule. The amount of radiation contemplated herein ranges from about 1 to about 100 Gy, including, for example, about 5 to about 80, about 10 to about 50 Gy, or about 10 Gy. The total dose may be applied in a fractioned regime. For example, the regime may comprise fractionated individual doses of 2 Gy. Dosage ranges for radioisotopes vary widely, and depends on the half-life of the isotope and the strength and type of radiation emitted.

When the radiation comprises use of radioactive isotopes, the isotope may be conjugated to a targeting agent, such as a therapeutic antibody, which carries the radionucleotide to the target tissue. Suitable radioactive isotopes include, but are not limited to, astatine$^{211}$, carbon$^{14}$, chromium$^{51}$, chlorine$^{36}$, iron$^{57}$, cobalt$^{58}$, copper$^{67}$, Eu$^{152}$, gallium$^{67}$, hydrogen$^{3}$, iodine$^{123}$, iodine$^{131}$, indium$^{111}$, iron$^{59}$, phosphorus$^{32}$, rhenium$^{186}$, selenium$^{75}$, sulphur$^{35}$, technicium$^{99m}$, and/or yttrium$^{90}$.

In some embodiments, enough radiation is applied to the individual so as to allow reduction of the normal dose of the taxane (such as paclitaxel) in the nanoparticle composition required to effect the same degree of treatment by at least about any of 5%, 10%, 20%, 30%, 50%, 60%, 70%, 80%, 90%, or more. In some embodiments, enough taxane in the nanoparticle composition is administered so as to allow reduction of the normal dose of the radiation required to effect the same degree of treatment by at least about any of 5%, 10%, 20%, 30%, 50%, 60%, 70%, 80%, 90%, or more. In some embodiments, the dose of both the taxane (such as paclitaxel) in the nanoparticle composition and the radiation are reduced as compared to the corresponding normal dose of each when used alone.

In some embodiments, the combination of administration of the nanoparticle composition and the radiation therapy produce supra-additive effect. In some embodiments, the taxane (such as paclitaxel) in the nanoparticle composition is administered once at the dose of 90 mg/kg, and the radiation is applied five times at 80 Gy daily.

Surgery described herein includes resection in which all or part of cancerous tissue is physically removed, exercised, and/or destroyed. Tumor resection refers to physical removal of at least part of a tumor. In addition to tumor resection, treatment by surgery includes laser surgery, cryosurgery, electrosurgery, and micropically controlled surgery (Mohs surgery). Removal of superficial surgery, precancers, or normal tissues are also contemplated.

The radiation therapy and/or surgery may be carried out in addition to the administration of chemotherapeutic agents. For example, the individual may first be administered with a taxane-containing nanoparticle composition and at least one other chemotherapeutic agent, and subsequently be subject to radiation therapy and/or surgery. Alternatively, the individual may first be treated with radiation therapy and/or surgery, which is then followed by the administration of a nanoparticle composition and at least one other chemotherapeutic agent. Other combinations are also contemplated.

Administration of nanoparticle compositions disclosed above in conjunction with administration of chemotherapeutic agent is equally applicable to those in conjunction with radiation therapy and/or surgery.

In some embodiments, the invention provides pharmaceutical compositions comprising nanoparticles comprising a taxane (such as paclitaxel) and a carrier protein (such as albumin) for use in the treatment of breast cancer based on hormone receptor status (e.g., not expressing the estrogen receptor and/or progesterone receptor), wherein said use comprises a second therapy comprising radiation therapy, surgery, or combinations thereof.

Metronomic Therapy

The invention also provides metronomic therapy regime for treatment of breast cancer based on hormone receptor status (e.g., not expressing the estrogen receptor and/or progesterone receptor). There is provided a method of administering to an individual a composition comprising nanoparticles comprising a taxane (such as paclitaxel, docetaxel, or ortataxel) and a carrier protein (such as albumin) based on a metronomic dosing regime. The methods are applicable to methods of treatment, delaying development, and other clinical settings and configurations described herein.

In some embodiments, the hormone receptor status is low for one or more hormone receptors such as the estrogen receptor or the progesterone receptor. In some embodiments, the individual is likely more responsive to the therapy if hormone receptor status is low for both estrogen receptor and progesterone receptor. In some embodiments, the hormone receptor status does not express (i.e., is negative for) one or more hormone receptors such as the estrogen receptor (ER) or the progesterone receptor (PgR). In some embodiments, the hormone receptor status of the breast cancer tissue does not express (i.e., is negative for) both the estrogen receptor (ER) and the progesterone receptor (PgR). In some embodiments, the individual is likely more responsive to the therapy if hormone receptor status is negative for both estrogen receptor and progesterone receptor. In some embodiments, the individual expresses (i.e., is positive for) either the estrogen receptor or the progesterone receptor. In some embodiments, the individual expresses (i.e., is positive for) both the estrogen receptor and the progesterone receptor. In some embodiments, the individual is likely less responsive to therapy if the hormone receptor status is positive for the estrogen receptor and/or the progesterone receptor.

In some embodiments, the breast cancer tissue further expresses HER2 (HER2+). In some embodiments, the breast cancer tissue further does not express HER2 (HER2−).

Metronomic dosing regime" used herein refers to frequent administration of a taxane at without prolonged breaks at a dose below the established maximum tolerated dose via a traditional schedule with breaks (hereinafter also referred to as a "standard MTD schedule" or a "standard MTD regime"). In metronomic dosing, the same, lower, or higher cumulative dose over a certain time period as would be administered via a standard MTD schedule may ultimately be administered. In some cases, this is achieved by extending the time frame and/or frequency during which the dosing regime is conducted while decreasing the amount administered at each dose. Generally, the taxane administered via the metronomic dosing regime of the present invention is better tolerated by the individual. Metronomic dosing can also be referred to as maintenance dosing or chronic dosing.

In some embodiments, there is provided a method of administering a composition comprising nanoparticles comprising a taxane and a carrier protein (such as albumin), wherein the nanoparticle composition is administered over a period of at least one month, wherein the interval between each administration is no more than about a week, and wherein the dose of the taxane at each administration is about 0.25% to about 25% of its maximum tolerated dose following a traditional dosing regime. In some embodiments, there is provided a method of administering a composition comprising nanoparticles comprising paclitaxel and an albumin, wherein the nanoparticle composition is administered over a period of at least one month, wherein the interval between each administration is no more than about a week, and wherein the dose of the taxane at each administration is about 0.25% to about 25% of its maximum tolerated dose following a traditional dosing regime.

In some embodiments, the dosing of the taxane (such as paclitaxel) in the nanoparticle composition per administration is less than about any of 1%, 2%, 3&, 4%, 5%, 6%, 7%, 8%, 9%, 10%, 11%, 12%, 13%, 14%, 15%, 18%, 20%, 22%, 24%, or 25% of the MTD for the same taxane (such as paclitaxel) in the same formulation following a given traditional dosing schedule. Traditional dosing schedule refers to the dosing schedule that is generally established in a clinical setting. For example, the tradition dosing schedule for Abraxane® is a three-weekly schedule, i.e., administering the composition every three weeks.

In some embodiments, the dosing of the taxane (such as paclitaxel) per administration is between about 0.25% to about 25% of the corresponding MTD value, including for example any of about 0.25% to about 20%, about 0.25% to about 15%, about 0.25% to about 10%, about 0.25% to about 20%, and about 0.25% to about 25%, of the corresponding MTD value. The MTD value for a taxane following a traditional dosing schedule is known or can be easily determined by a person skilled in the art. For example, the MTD value when Abraxane® is administered following a traditional three-week dosing schedule is about 300 mg/m².

In some embodiments, there is provided a method of administering a composition comprising nanoparticles comprising a taxane and a carrier protein (such as albumin), wherein the nanoparticle composition is administered over a period of at least one month, wherein the interval between each administration is no more than about a week, and wherein the dose of the taxane at each administration is about 0.25 mg/m² to about 25 mg/m². In some embodiments, there is provided a method of administering a composition comprising nanoparticles comprising paclitaxel and an albumin, wherein the nanoparticle composition is administered over a period of at least one month, wherein the interval between each administration is no more than about a week, and wherein the dose of the taxane at each administration is about 0.25 mg/m² to about 25 mg/m².

In some embodiments, the dose of the taxane (such as paclitaxel) at each administration is less than about any of 2, 3, 4, 5, 6, 7, 8, 9, 10, 11, 12, 13, 14, 15, 18, 20, 22, 25, and 30 mg/m². For example, the dose of the taxane (such as paclitaxel) can range from about 0.25 mg/m² to about 30 mg/m², about 0.25 mg/m² to about 25 mg/m², about 0.25 mg/m² to about 15 mg/m², about 0.25 mg/m² to about 10 mg/m², and about 0.25 mg/m² to about 5 mg/m².

Dosing frequency for the taxane (such as paclitaxel) in the nanoparticle composition includes, but is not limited to, at least about any of once a week, twice a week, three times a week, four times a week, five times a week, six times a week, or daily. Typically, the interval between each administration is less than about a week, such as less than about any of 6, 5, 4, 3, 2, or 1 day. In some embodiments, the interval between each administration is constant. For example, the administration can be carried out daily, every two days, every three days, every four days, every five days, or weekly. In some embodiments, the administration can be carried out twice daily, three times daily, or more frequent.

The metronomic dosing regimes described herein can be extended over an extended period of time, such as from about a month up to about three years. For example, the dosing regime can be extended over a period of any of about 2, 3, 4, 5, 6, 7, 8, 9, 10, 11, 12, 18, 24, 30, and 36 months. Generally, there are no breaks in the dosing schedule.

The cumulative dose of the taxane (such as paclitaxel) administered by the metronomic regime may be higher than that of the taxane administered according to a standard MTD dosing schedule over the same time period. In some embodiments, the cumulative dose of the taxane administered by the metronomic regime equals to or is lower than that of the taxane administered according to a standard MTD dosing schedule over the same time period.

It is understood that the teaching provided herein is for examples only, and that metronomic dosing regime can be routinely designed in accordance with the teachings provided herein and based upon the individual standard MTD schedule, and that the metronomic dosing regime used in these experiments merely serves as one example of possible changes in dosing interval and duration which are made to a standard MTD schedule to arrive at an optimal metronomic dosing regime.

The metronomic dosing regime described herein may be used alone as a treatment of a proliferative disease, or carried out in a combination therapy context, such as the combination therapies described herein. In some embodiments, the metronomic therapy dosing regime may be used in combination or conjunction with other established therapies administered via standard MTD regimes. By "combination or in conjunction with" it is meant that the metronomic dosing regime of the present invention is conducted either at the same time as the standard MTD regime of established therapies, or between courses of induction therapy to sustain the benefit accrued to the individual by the induction therapy, the intent is to continue to inhibit tumor growth while not unduly compromising the individual's health or the individual's ability to withstand the next course of induction therapy. For example, a metronomic dosing regime may be adopted after an initial short course of MTD chemotherapy.

The nanoparticle compositions administered based on the metronomic dosing regime described herein can be administered to an individual (such as human) via various routes, such as parenterally, including intravenous, intra-arterial, intrapulmonary, oral, inhalation, intravesicular, intramuscular, intra-tracheal, subcutaneous, intraocular, intrathecal, or transdermal. For example, the nanoparticle composition can be administered by inhalation to treat conditions of the respiratory tract. The composition can be used to treat respiratory conditions such as pulmonary fibrosis, broncheolitis obliterans, lung cancer, bronchoalveolar carcinoma, and the like. In some embodiments, the nanoparticle composition is administered orally.

Some exemplary embodiments are provided below.

In some embodiments, there is provided a method of administering a composition comprising nanoparticles comprising a taxane and a carrier protein (such as albumin), wherein the nanoparticle composition is administered over a period of at least one month, wherein the interval between each administration is no more than about a week, and wherein the dose of the taxane at each administration is about 0.25% to about 25% of its maximum tolerated dose following a traditional dosing regime. In some embodiments, the taxane is coated with the carrier protein (such as albumin). In some embodiments, the dose of the taxane per administration is less than about any of 1%, 2%, 3%, 4%, 5%, 6%, 7%, 8%, 9%, 10%, 11%, 12%, 13%, 14%, 15%, 18%, 20%, 22%, 24%, or 25% of the maximum tolerated dose. In some embodiments, the taxane is administered at least about any of 1×, 2×, 3×, 4×, 5×, 6×, 7× (i.e., daily) a week. In some embodiments, the intervals between each administration are less than about any of 7 days, 6 days, 5 days, 4 days, 3 days, 2 days, and 1 day. In some embodiments, the taxane is administered over a period of at least about any of 2, 3, 4, 5, 6, 7, 8, 9, 10, 11, 12, 18, 24, 30 and 36 months.

In some embodiments, there is provided a method of administering a composition comprising nanoparticles comprising paclitaxel and an albumin, wherein the nanoparticle composition is administered over a period of at least one month, wherein the interval between each administration is no more than about a week, and wherein the dose of the taxane at each administration is about 0.25% to about 25% of its maximum tolerated dose following a traditional dosing regime. In some embodiments, the paclitaxel/albumin nanoparticles have an average diameter of no greater than about 200 nm. In some embodiments, the paclitaxel/albumin nanoparticle composition is substantially free (such as free) of surfactant (such as Cremophor), In some embodiments, the weight ratio of the albumin to paclitaxel in the composition is about 18:1 or less, such as about 9:1 or less. In some embodiments, the paclitaxel is coated with albumin. In some embodiments, the paclitaxel/albumin nanoparticles have an average diameter of no greater than about 200 nm and the paclitaxel/albumin composition is substantially free (such as free) of surfactant (such as Cremophor). In some embodiments, the paclitaxel/albumin nanoparticles have an average diameter of no greater than about 200 nm and the paclitaxel is coated with albumin. In some embodiments, the nanoparticle composition is Abraxane®.

In some embodiments, there is provided a method of administering a composition comprising nanoparticles comprising a taxane and a carrier protein (such as albumin), wherein the nanoparticle composition is administered over a period of at least one month, wherein the interval between each administration is no more than about a week, and wherein the dose of the taxane at each administration is about 0.25 mg/m² to about 25 mg/m². In some embodiments, the taxane is coated with the carrier protein (such as albumin). In some embodiments, the dose of the taxane per administration is less than about any of 2, 3, 4, 5, 6, 7, 8, 9, 10, 11, 12, 13, 14, 15, 18, 20, 22, and 25 mg/m². In some embodiments, the taxane is administered at least about any of 1×, 2×, 3×, 4×, 5×, 6×, 7× (i.e., daily) a week. In some embodiments, the intervals between each administration are less than about any of 7 days, 6 days, 5 days, 4 days, 3 days, 2 days, and 1 day. In some embodiments, the taxane is administered over a period of at least about any of 2, 3, 4, 5, 6, 7, 8, 9, 10, 11, 12, 18, 24, 30 and 36 months.

In some embodiments, there is provided a method of administering a composition comprising nanoparticles comprising paclitaxel and an albumin, wherein the nanoparticle composition is administered over a period of at least one month, wherein the interval between each administration is no more than about a week, and wherein the dose of the taxane at each administration is about 0.25 mg/m² to about 25 mg/m². In some embodiments, the paclitaxel/albumin nanoparticles have an average diameter of no greater than about 200 nm. In some embodiments, the paclitaxel/albumin nanoparticle composition is substantially free (such as free) of surfactant (such as Cremophor). In some embodiments, the weight ratio of the albumin to paclitaxel in the composition is about 18:1 or less, such as about 9:1 or less. In some embodiments, the paclitaxel is coated with albumin. In some embodiments, the paclitaxel/albumin nanoparticles have an average diameter of no greater than about 200 nm and the paclitaxel/albumin composition is substantially free (such as free) of surfactant (such as Cremophor). In some embodiments, the paclitaxel/albumin nanoparticles have an average diameter of no greater than about 200 nm and the paclitaxel is coated with albumin. In some embodiments, the nanoparticle composition is Abraxane®.

In some embodiments, the Abraxane® (or other paclitaxel/albumin nanoparticle compositions) is administered at the dose of about 3 mg/kg to about 10 mg/kg daily. In some embodiments, the Abraxane® is administered at the dose of about 6 mg/kg to about 10 mg/kg daily. In some embodiments, the Abraxane® is administered at the dose of about 6 mg/kg daily. In some embodiments, Abraxane® is administered at the dose of about 3 mg/kg daily.

The invention also provides compositions for use in the metronomic regime(s) described herein. In some embodiments, there is provided a composition comprising nanoparticles comprising a taxane and a carrier protein (such as albumin), wherein said composition is administered to an individual via a metronomic dosing regime, such as the dosing regime described herein.

Other Aspects of the Invention

In another aspects, there are provided methods of treating breast cancer based on hormone receptor status (e.g., not expressing the estrogen receptor and/or progesterone receptor) comprising administering a composition comprising nanoparticles comprising a taxane (including pachiaxel, docetaxel, or ortataxel) and a carrier protein (such as albumin). In some embodiments, there is provided a method of treating breast cancer based on hormone receptor status (e.g., not expressing the estrogen receptor and/or progesterone receptor) comprising administering a composition comprising nanoparticles comprising ortataxel and a carrier protein (such as albumin).

In some embodiments, there is provided a method of treating cancer comprising administering a composition comprising nanoparticles comprising paclitaxel, wherein the nanoparticle composition is administered according to any of the dosing regimes described in Table 2. In some embodiments, the cancer is a Taxane refractory metastatic breast cancer.

TABLE 2

| Row No. | Combination | Regimen/Dosage | Study therapy type | Protocol title |
|---|---|---|---|---|
| 1. | ABX alone | ABX: 125 mg/m$^2$ qwk × 3/4 | Metastatic Breast Cancer | Phase II study with weekly Abraxane ® treatment in taxane-refractory MBC patients |
| 2. | ABX alone | Arm 1: ABX 130 mg/m$^2$ qwk<br>Arm 2: ABX 260 mg/m$^2$ q2wk<br>Arm 3: ABX 260 mg/m$^2$ q3wk | Metastatic Breast Cancer | 3-arm phase II trial in 1st-line Her-2– MBC patients. |
| 3. | ABX alone (Capxol) | ABX: 260 mg/m$^2$ q3wk<br>vs<br>Taxol: 175 mg/m$^2$ q3wk | Metastatic Breast Cancer | Phase II Controlled, Randomized, Open Label Study to Evaluate the Efficacy and Safety of Capxol (a Cremophor-Free Nanoparticle Paclitaxel) and cremophor-formulated paclitaxel injection in Patient with Metastatic Breast Cancer |
| 4. | ABX alone | Arm 1: ABX weekly<br>Arm 2: ABX q3wk<br>Arm 3: Taxol weekly | Metastatic Breast Cancer | 3-arm phase II trial in 1st-line and 2nd-line MBC, with biological correlates analysis |
| 5. | ABX alone | ABX: 300 mg/m$^2$ q3wk | Stage IIA, IIB, IIIA, IIIB and IV breast cancer | Phase II trial of neoadjuvant chemotherapy (NCT) with nanoparticle paclitaxel (ABI-007, Abraxane ®) in women with clinical stage IIA, IIB, IIIA, IIIB and IV (with intact primary) breast cancers |

Nanoparticle Compositions

The nanoparticle compositions described herein comprise nanoparticles comprising (in various embodiments consisting essentially of) a taxane (such as paclitaxel) and a carrier protein (such as albumin). Nanoparticles of poorly water soluble drugs (such as taxane) have been disclosed in, for example, U.S. Pat. Nos. 5,916,596; 6,506,405; and 6,537,579 and also in U.S. Pat. Pub. No. 2005/0004002A1. Although the description provided below is specific to taxane, it is understood that the same applies to other drugs, such as rapamycin, 17-AAG, and dimeric thiocolchicine.

In some embodiments, the composition comprises nanoparticles with an average or mean diameter of no greater than about 1000 nanometers (nm), such as no greater than about any of 900, 800, 700, 600, 500, 400, 300, 200, and 100 nm. In some embodiments, the average or mean diameters of the nanoparticles is no greater than about 200 nm. In some embodiments, the average or mean diameters of the nanoparticles is no greater than about 150 nm. In some embodiments, the average or mean diameters of the nanoparticles is no greater than about 100 nm. In some embodiments, the average or mean diameter of the nanoparticles is about 20 to about 400 nm. In some embodiments, the average or mean diameter of the nanoparticles is about 40 to about 200 nm. In some embodiments, the nanoparticles are sterile-filterable.

The nanoparticles described herein may be present in a dry formulation (such as lyophilized composition) or suspended in a biocompatible medium. Suitable biocompatible media include, but are not limited to, water, buffered aqueous media, saline, buffered saline, optionally buffered solutions of amino acids, optionally buffered solutions of proteins, optionally buffered solutions of sugars, optionally buffered solutions of vitamins, optionally buffered solutions of synthetic polymers, lipid-containing emulsions, and the like.

The term "proteins" refers to polypeptides or polymers of amino acids of any length (including full length or fragments), which may be linear or branched, comprise modified amino acids, and/or be interrupted by non-amino acids. The term also encompasses an amino acid polymer that has been modified naturally or by intervention; for example, disulfide bond formation, glycosylation, lipidation, acetylation, phosphorylation, or any other manipulation or modification. Also included within this term are, for example, polypeptides containing one or more analogs of an amino acid (including, for example, unnatural amino acids, etc.), as well as other modifications known in the art. The proteins described herein may be naturally occurring, i.e., obtained or derived from a natural source (such as blood), or synthesized (such as chemically synthesized or by synthesized by recombinant DNA techniques).

Examples of suitable carrier proteins include proteins normally found in blood or plasma, which include, but are not limited to, albumin, immunoglobulin including IgA, lipoproteins, apolipoprotein B, alpha-acid glycoprotein, beta-2-macroglobulin, thyroglobulin, transferin, fibronectin, factor VII, factor VIII, factor IX, factor X, and the like. In some embodiments, the carrier protein is non-blood protein, such as casein, α-lactalbumin, and β-lactoglobulin. The carrier proteins may either be natural in origin or synthetically prepared. In some embodiments, the pharmaceutically acceptable carrier comprises albumin, such as human serum albumin. Human serum albumin (HSA) is a highly soluble globular protein of M, 65K and consists of 585 amino acids. HSA is the most abundant protein in the plasma and accounts for 70-80% of the colloid osmotic pressure of human plasma. The amino acid sequence of HSA contains a total of 17 disulphide bridges, one free thiol (Cys 34), and a single tryptophan (Trp 214). Intravenous use of HSA solution has been indicated for the prevention and treatment of hypovolumic shock (see, e.g., Tullis, *JAMA* 237: 355-360, 460-463 (1977)) and Houser et al., *Surgery, Gynecology and Obstetrics,* 150: 811-816 (1980)) and in conjunction with exchange transfusion in the treatment of neonatal hyperbilirubinemia (see, e.g., Finlayson, *Seminars in Thrombosis and Hemostasis,* 6: 85-120 (1980)). Other albumins are contemplated, such as bovine serum albumin. Use of such non-human albumins could be appropriate, for example, in the context of use of these compositions in non-human mammals, such as the veterinary (including domestic pets and agricultural context).

Human serum albumin (HSA) has multiple hydrophobic binding sites (a total of eight for fatty acids, an endogenous ligand of HSA) and binds a diverse set of taxanes, especially neutral and negatively charged hydrophobic compounds (Goodman et al., *The Pharmacological Basis of Therapeutics,* 9$^{th}$ ed, McGraw-Hill New York (1996)). Two high affinity binding sites have been proposed in subdomains IIA and IIIA of HSA, which are highly elongated hydrophobic pockets with charged lysine and arginine residues near the surface which function as attachment points for polar ligand features (see, e.g., Fehske et al., *Biochem. Pharmcol.* 30: 687-92 (198a), Vorum, *Dan. Med. Bull.* 46: 379-99 (1999), Kragh-Hansen, Dan, *Med Bull.* 1441: 131-40 (1990), Curry et al., *Nat. Struct. Biol.* 5: 827-35 (1998), Sugio et al., *Protein. Eng.* 12: 439-46 (1999), He et al., *Nature* 358: 209-15 (199b), and Carter et al., *Adv. Protein. Chem.* 45: 153-203 (1994)). Paclitaxel and propofol have been shown to bind HSA (see, e.g., Paal et al., *Eur. Biochem.* 268(7): 2187-91 (200a), Purcell et at, *Biochim. Biophys. Act*α1478 (a): 61-8 (2000), Altmayer et al., *Arzneimittelforschung* 45: 1053-6 (1995), and Garrido et al., *Rev. Esp. Anestestiol. Reanim.* 41: 308-12 (1994)). In addition, docetaxel has been shown to bind to human plasma proteins (see, e.g., Urien et al., *Invest. New Drugs* 14(b): 147-51 (1996)).

The carrier protein (such as albumin) in the composition generally serves as a carrier for the taxane, i.e., the carrier protein in the composition makes the taxane more readily suspendable in an aqueous medium or helps maintain the suspension as compared to compositions not comprising a carrier protein. This can avoid the use of toxic solvents (or surfactants) for solubilizing the taxane, and thereby can reduce one or more side effects of administration of the taxane into an individual (such as a human). Thus, in some embodiments, the composition described herein is substantially free (such as free) of surfactants, such as Cremophor (including Cremophor EL® (BASF)). In some embodiments, the nanoparticle composition is substantially free (such as free) of surfactants. A composition is "substantially free of Cremophor" or "substantially free of surfactant" if the amount of Cremophor or surfactant in the composition is not sufficient to cause one or more side effect(s) in an individual when the nanoparticle composition is administered to the individual.

The amount of carrier protein in the composition described herein will vary depending on other components in the composition. In some embodiments, the composition comprises a carrier protein in an amount that is sufficient to stabilize the taxane in an aqueous suspension, for example, in the form of a stable colloidal suspension (such as a stable suspension of nanoparticles). In some embodiments, the carrier protein is in an amount that reduces the sedimentation rate of the taxane in an aqueous medium. For particle-containing compositions, the amount of the carrier protein also depends on the size and density of nanoparticles of the taxane.

A taxane is "stabilized" in an aqueous suspension if it remains suspended in an aqueous medium (such as without visible precipitation or sedimentation) for an extended period of time, such as for at least about any of 0.1, 0.2, 0.25, 0.5, 1, 2, 3, 4, 5, 6, 7, 8, 9, 10, 11, 12, 24, 36, 48, 60, or 72 hours. The suspension is generally, but not necessarily, suitable for administration to an individual (such as human). Stability of the suspension is generally (but not necessarily) evaluated at a storage temperature (such as room temperature (such as 20-25° C.) or refrigerated conditions (such as 4° C.)). For example, a suspension is stable at a storage temperature if it exhibits no flocculation or particle agglomeration visible to the naked eye or when viewed under the optical microscope at 1000 times, at about fifteen minutes after preparation of the suspension. Stability can also be evaluated under accelerated testing conditions, such as at a temperature that is higher than about 40° C.

In some embodiments, the carrier protein is present in an amount that is sufficient to stabilize the taxane in an aqueous suspension at a certain concentration. For example, the concentration of the taxane in the composition is about 0.1 to about 100 mg/ml, including for example any of about 0.1 to about 50 mg/ml, about 0.1 to about 20 mg/ml, about 1 to about 10 mg/ml, about 2 mg/ml to about 8 mg/ml, about 4 to about 6 mg/ml, about 5 mg/ml. In some embodiments, the concentration of the taxane is at least about any of 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, and 50 mg/ml. In some embodiments, the carrier protein is present in an amount that avoids use of surfactants (such as Cremophor), so that the composition is free or substantially free of surfactant (such as Cremophor).

In some embodiments, the composition, in liquid form, comprises from about 0.1% to about 50% (w/v) (e.g. about 0.5% (w/v), about 5% (w/v), about 10% (w/v), about 15% (w/v), about 20% (w/v), about 30% (w/v), about 40% (w/v), or about 50% (w/v)) of carrier protein. In some embodiments, the composition, in liquid form, comprises about 0.5% to about 5% (w/v) of carrier protein.

In some embodiments, the weight ratio of carrier protein, e.g., albumin, to the taxane in the nanoparticle composition is such that a sufficient amount of taxane binds to, or is transported by, the cell. While the weight ratio of carrier protein to taxane will have to be optimized for different carrier protein and taxane combinations, generally the weight ratio of carrier protein, e.g., albumin, to taxane (w/w) is about 0.01:1 to about 100:1, about 0.02:1 to about 50:1, about 0.05:1 to about 20:1, about 0.1:1 to about 20:1, about 1:1 to about 18:1, about 2:1 to about 15:1, about 3:1 to about 12:1, about 4:1 to about 10:1, about 5:1 to about 9:1, or about 9:1. In some embodiments, the carrier protein to taxane weight ratio is about any of 18:1 or less, 15:1 or less, 14:1 or less, 13:1 or less, 12:1 or less, 11:1 or less, 10:1 or less, 9:1 or less, 8:1 or less, 7:1 or less, 6:1 or less, 5:1 or less, 4:1 or less, and 3:1 or less.

In some embodiments, the carrier protein allows the composition to be administered to an individual (such as human) without significant side effects. In some embodiments, the carrier protein (such as albumin) is in an amount that is effective to reduce one or more side effects of administration of the taxane to a human. The term "reducing one or more side effects of administration of the taxane" refers to reduction, alleviation, elimination, or avoidance of one or more undesirable effects caused by the taxane, as well as side effects caused by delivery vehicles (such as solvents that render the taxanes suitable for injection) used to deliver the taxane. Such side effects include, for example, myelosuppression, neurotoxicity, hypersensitivity, inflammation, venous irritation, phlebitis, pain, skin irritation, peripheral neuropathy, neutropenic fever, anaphylactic reaction, venous thrombosis, extravasation, and combinations thereof. These side effects, however, are merely exemplary and other side effects, or combination of side effects, associated with taxanes can be reduced.

In some embodiments, the composition comprises Abraxane®. Abraxane® is a formulation of paclitaxel stabilized by human albumin USP, which can be dispersed in directly injectable physiological solution. When dispersed in a suitable aqueous medium such as 0.9% sodium chloride injection or 5% dextrose injection, Abraxane® forms a stable colloidal suspension of paclitaxel. The mean particle size of the nanoparticles in the colloidal suspension is about 130 nanometers. Since HSA is freely soluble in water, Abraxane® can be reconstituted in a wide range of concentrations ranging from dilute (0.1 mg/ml paclitaxel) to concentrated (20 mg/ml paclitaxel), including for example about 2 mg/ml to about 8 mg/ml, about 5 mg/ml.

Methods of making nanoparticle compositions are known in the art. For example, nanoparticles containing taxanes (such as paclitaxel) and carrier protein (such as albumin) can be prepared under conditions of high shear forces (e.g., sonication, high pressure homogenization, or the like). These methods are disclosed in, for example, U.S. Pat. Nos. 5,916,596; 6,506,405; and 6,537,579 and also in U.S. Pat. Pub. No. 2005/0004002A1.

Briefly, the taxane (such as docetaxel) is dissolved in an organic solvent, and the solution can be added to a human serum albumin solution. The mixture is subjected to high pressure homogenization. The organic solvent can then be removed by evaporation. The dispersion obtained can be further lyophilized. Suitable organic solvent include, for example, ketones, esters, ethers, chlorinated solvents, and other solvents known in the art. For example, the organic solvent can be methylene chloride and chloroform/ethanol (for example with a ratio of 1:9, 1:8, 1:7, 1:6, 1:5, 1:4, 1:3, 1:2, 1:1, 2:1, 3:1, 4:1, 5:1, 6:1, 7:1, 8:1, or 9:a).

Other Components in the Nanoparticle Compositions

The nanoparticles described herein can be present in a composition that include other agents, excipients, or stabilizers. For example, to increase stability by increasing the negative zeta potential of nanoparticles, certain negatively charged components may be added. Such negatively charged components include, but are not limited to bile salts of bile acids consisting of glycocholic acid, cholic acid, chenodeoxycholic acid, taurocholic acid, glycochenodeoxycholic acid, taurochenodeoxycholic acid, litocholic acid, ursodeoxycholic acid, dehydrocholic acid and others; phospholipids including lecithin (egg yolk) based phospholipids which include the following phosphatidylcholines: palmitoyloleoylphosphatidylcholine, palmitoyllinoleoylphosphatidylcholine, stearoyllinoleoylphosphatidylcholine stearoyloleoylphosphatidylcholine, stearoylarachidoylphosphatidylcholine, and dipalmitoylphosphatidylcholine. Other phospholipids including L-α-dimyristoylphosphatidylcholine (DMPC), dioleoylphosphatidylcholine (DOPC), distearyolphosphatidylcholine (DSPC), hydrogenated soy phosphatidylcholine (HSPC), and other related compounds. Negatively charged surfactants or emulsifiers are also suitable as additives, e.g., sodium cholesteryl sulfate and the like.

In some embodiments, the composition is suitable for administration to a human. In some embodiments, the composition is suitable for administration to a mammal such as, in the veterinary context, domestic pets and agricultural animals. There are a wide variety of suitable formulations of the nanoparticle composition (see, e.g., U.S. Pat. Nos. 5,916,596 and 6,096,331). The following formulations and methods are merely exemplary and are in no way limiting. Formulations suitable for oral administration can consist of (a) liquid solutions, such as an effective amount of the compound dissolved in diluents, such as water, saline, or orange juice, (b) capsules, sachets or tablets, each containing a predetermined amount of the active ingredient, as solids or granules, (c) suspensions in an appropriate liquid, and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

Examples of suitable carriers, excipients, and diluents include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline solution, syrup, methylcellulose, methyl- and propylhydroxybenzoates, talc, magnesium stearate, and mineral oil. The formulations can additionally include lubricating agents, wetting agents, emulsifying and suspending agents, preserving agents, sweetening agents or flavoring agents.

Formulations suitable for parenteral administration include aqueous and non-aqueous, isotonic sterile injection solutions, which can contain anti-oxidants, buffers, bacteriostats, and solutes that render the formulation compatible with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described. Injectable formulations are preferred.

In some embodiments, the composition is formulated to have a pH range of about 4.5 to about 9.0, including for example pH ranges of any of about 5.0 to about 8.0, about 6.5 to about 7.5, and about 6.5 to about 7.0. In some embodiments, the pH of the composition is formulated to no less than about 6, including for example no less than about any of 6.5, 7, or 8 (such as about 8). The composition can also be made to be isotonic with blood by the addition of a suitable tonicity modifier, such as glycerol.

Kits

The invention also provides kits for use in the instant methods. Kits of the invention include a detection means for identifying the hormone receptor status of a breast cancer patient (e.g., having tumor tissue not expressing both estrogen receptor (ER) and progesterone receptor (PgR)). In some embodiments, the kit comprising: (a) an agent for detecting hormone receptor status of estrogen receptor and/ or progesterone receptor of a breast cancer patient; and (b) a composition comprising nanoparticles comprising a taxane and a carrier protein. In some embodiments, the kit comprising: (a) an agent for detecting hormone receptor status of estrogen receptor and/or progesterone receptor of a breast cancer patient; and (b) instructions for assessing likely responsiveness to therapy for treating breast cancer based on hormone receptor status of estrogen receptor and/or progesterone receptor, wherein the therapy comprises administering a composition comprising nanoparticles comprising a taxane and a carrier protein. In some embodiments, the instructions further provide instructions for administering to the patient an effective amount of the composition.

In some embodiments, the kits of the invention further include one or more containers comprising taxane-containing nanoparticle compositions (or unit dosage forms and/or articles of manufacture). In some embodiments, the kits of the invention include one or more containers comprising taxane-containing nanoparticle compositions (or unit dosage forms and/or articles of manufacture) and/or a chemotherapeutic agent, and in some embodiments, further comprise instructions for use in accordance with any of the methods described herein. The kit may further comprise a description of selection an individual suitable or treatment. Instructions supplied in the kits of the invention are typically written instructions on a label or package insert (e.g., a paper sheet included in the kit), but machine-readable instructions (e.g., instructions carried on a magnetic or optical storage disk) are also acceptable. In some embodiments, the instructions include instructions for treating breast cancer based on hormone receptor status (e.g., not expressing both estrogen receptor (ER) and progesterone receptor (PgR)) comprising administering to an individual an effective amount of a composition comprising nanoparticles comprising a taxane and a carrier protein.

In some embodiments, the hormone receptor status is low for one or more hormone receptors such as the estrogen receptor or the progesterone receptor. In some embodiments, the individual is likely more responsive to the therapy if hormone receptor status is low for both estrogen receptor and progesterone receptor. In some embodiments, the hormone receptor status does not express (i.e., is negative for) one or more hormone receptors such as the estrogen receptor (ER) or the progesterone receptor (PgR). In some embodiments, the hormone receptor status of the breast cancer tissue does not express (i.e., is negative for) both the estrogen receptor (ER) and the progesterone receptor (PgR). In some embodiments, the individual is likely more responsive to the therapy if hormone receptor status is negative for both estrogen receptor and progesterone receptor. In some embodiments, the individual expresses (i.e., is positive for) either the estrogen receptor or the progesterone receptor. In some embodiments, the individual expresses (i.e., is positive for) both the estrogen receptor and the progesterone receptor. In some embodiments, the individual is likely less responsive to therapy if the hormone receptor status is positive for the estrogen receptor and/or the progesterone receptor.

In some embodiments, the breast cancer tissue further expresses HER2 (HER2+). In some embodiments, the breast cancer tissue further does not express HER2 (HER2−).

In some embodiments, the kit comprises a) a composition comprising nanoparticles comprising a taxane and a carrier protein (such as albumin), b) an effective amount of at least one other chemotherapeutic agent, and c) instructions for administering the nanoparticles and the chemotherapeutic agents simultaneously and/or sequentially, for treatment of breast cancer based on hormone receptor status (e.g., not expressing the estrogen receptor and/or progesterone receptor). In some embodiments, the taxane is any of paclitaxel, docetaxel, and ortataxel. In some embodiments, the kit comprises nanoparticles comprising a) a composition comprising nanoparticles comprising paclitaxel and an albumin (such as Abraxane®), b) an effective amount of at least one other chemotherapeutic agent, and c) instructions for administering the nanoparticles and the chemotherapeutic agents simultaneously and/or sequentially, for the effective treatment of breast cancer based on hormone receptor status (e.g., not expressing the estrogen receptor and/or progesterone receptor).

In some embodiments, the kit comprises a) a composition comprising nanoparticles comprising a taxane and a carrier protein (such as albumin), b) a composition comprising nanoparticles comprising at least one other chemotherapeutic agent and a carrier protein (such as albumin), and c) instructions for administering the nanoparticle compositions simultaneously and/or sequentially, for treatment of breast cancer based on hormone receptor status (e.g., not expressing the estrogen receptor and/or progesterone receptor). In some embodiments, the kit comprises nanoparticles comprising a) a composition comprising nanoparticles comprising paclitaxel and an albumin (such as Abraxane®), b) a composition comprising nanoparticles comprising at least one other chemotherapeutic agent and a carrier protein (such as albumin), and c) instructions for administering the nanoparticle compositions simultaneously and/or sequentially, for the effective treatment of breast cancer based on hormone receptor status (e.g., not expressing the estrogen receptor and/or progesterone receptor).

The nanoparticles and the chemotherapeutic agents can be present in separate containers or in a single container. It is understood that the kit may comprise one distinct composition or two or more compositions wherein one composition comprises nanoparticles and one composition comprises a chemotherapeutic agent.

The kits of the invention are in suitable packaging. Suitable packaging include, but is not limited to, vials, bottles, jars, flexible packaging (e.g., sealed Mylar or plastic bags), and the like. Kits may optionally provide additional components such as buffers and interpretative information.

The instructions relating to the use of the nanoparticle compositions generally include information as to dosage, dosing schedule, and route of administration for the intended treatment. The containers may be unit doses, bulk packages (e.g., multi-dose packages) or sub-unit doses. For example, kits may be provided that contain sufficient dosages of the taxane (such as taxane) as disclosed herein to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the taxane and pharmaceutical compositions and instructions for use and packaged in quantities sufficient for storage and use in pharmacies, for example, hospital pharmacies and compounding pharmacies.

Those skilled in the art will recognize that several variations are possible within the scope and spirit of this invention. The invention will now be described in greater detail by reference to the following non-limiting examples. The following examples further illustrate the invention but, of course, should not be construed as in any way limiting its scope.

EXAMPLES

Example 1

Phase II Trial of Neoadjuvant Chemotherapy with Abraxane® Followed by 5-Fluorouracil, Epirubicin, and Cyclophosphamide (FEC) in Locally Advanced Breast Cancer Abraxane® has greater efficacy and favorable toxicity compared with Cremophor-based paclitaxel on a every 3 weeks schedule (Gradishar W J, et al. (2005) *J Clin Oncol* 23: 7794-7803). Weekly administration of Abraxane® has shown less toxicity than the every 3 weeks schedule and activity in taxane-refractory metastatic breast cancer (Blum J L, et al. (2004) *J Clin Oncol* 22: 14S, abstract 543). This trial was set up to determine the activity and safety profile of Abraxane® followed by 5-fluorouracil, Epirubicin, and cyclophosphamide (FEC) in women with locally advanced breast cancer (LABC).

66 women with LABC were administered preoperative Abraxane® at 100 mg/m$^2$ weekly for 12 consecutive weeks, followed by FEC every 3 weeks for 4 cycles. If their breast cancer was HER2 negative (HER2−) the FEC was administered at a dosage of 5-fluorouracil: 500 mg/m$^2$, Epirubicin: 100 mg/m$^2$, Cyclophosphamide: 500 mg/m$^2$) and referred to as FEC-100. If their cancer was HER2 positive (HER2+) the FEC was administered at a dosage of 5-fluorouracil: 500 mg/m$^2$, Epirubicin: 75 mg/m$^2$, Cyclophosphamide: 500 mg/m$^2$ (referred to as FEC-75) and they received trastuzumab (Herceptin®). Trastuzumab was co-administered with Abraxane® and FEC-75 on a standard weekly schedule at the discretion of the investigator in patients with HER2+ disease.

The primary endpoint of the trial was pathologic complete response rate following completion of the FEC treatment. The secondary endpoints included complete clinical response rates assessed at the completion of Abraxane®, toxicity/safety, progression-free survival, and overall survival.

The median age of the patients was 47 years (range of 28-70). Stage HB disease was present in 33% of the patients, stage IIIA in 42%, and stage IIIB in 24%. Tumors were evaluated for hormone receptor status, including estrogen receptor (ER) and progesterone receptor (PgR). 58% of patients were either ER or PgR positive, and 42% were negative for both receptors. HER2 status was evaluated in the patients, 29% were HER2+ fand 71% were HER2 negative. The protocol was completed in 58 (89.2%) of the patients, with therapy not completed for the rest. All 12 doses of Abraxane were administered to 61 of the patients; 48 received the 12 doses in 12 weeks, and 13 received the 12 doses in 13-14 weeks. Toxicity data with Abraxane showed the most frequent toxicities were diarrhea, rash, fatigue, nausea and sensory neuropathy. No Grade 4 or 5 toxicities and only one Grade 3 neutropenia were been reported.

Abraxane at 100 mg/m$^2$ administered weekly for 12 weeks had minimal toxicity and substantial activity, achieving a clinical complete response rate of 32% in patients (21/65) with locally advanced breast cancer (LABC). The sequential regimen of Abraxane followed by FEC was well tolerated, allowing for resection in all patients and breast-conserving surgery in 33%.

As shown in Table 3, the pathologic complete response (pCR) breast rate in HER2 positive LABC was 56% with concurrent treatment with trastuzumab. As shown in Table 4, the pathologic complete response (pCR) breast rate in HER2 negative, hormone receptor negative LABC was 29% (5/17); the pCR breast rate in HER2 negative, HR positive LABC was 10% (3/29).

TABLE 3

| HER2 STATUS<br>N = 64 | pCR<br>N (%) |
|---|---|
| Positive (18) | 10 (56%) |
| Trastuzumab 7 | 10 |
| No trastuzumab (1) | 0 |
| Negative (46) | 8 (17%) |

TABLE 4

| HORMONE RECEPTOR STATUS<br>N = 64 | pCR<br>N (%) |
|---|---|
| ER and/or PgR positive (38) | 7 (18%) |
| HER2 positive (9) | 4 (44%) |
| HER2 negative (29) | 3 (10%) |
| ER and PgR negative (26) | 11 (42%) |
| HER2 positive (9) | 6 (67%) |
| HER2 negative (17) | 5 (29%) |

Treatment with Abraxane followed by FEC demonstrated high efficacy in both HER2-negative patients and HER2-positive patients concurrently treated with trastuzumab. This treatment regimen was significantly more effective in patients that were ER and PgR negative than in patients that were ER and/or PgR positive, in both HER2-negative patients and HER2-positive patient populations.

Example 2

Improved Response and Reduced Toxicities for Abraxane® Compared to Taxol® in a Phase III Study of Abraxane® Given Every Three Weeks Significantly reduced incidence of neutropenia and hypersensitivity, absence of requirement of steroid premedication, shorter duration of neuropathy, shorter infusion time and higher dose.

ABI-007 (Abraxane®), the first biologically interactive albumin-bound paclitaxel in a nanoparticle form, free of any solvent, was compared with Cremophor®-based paclitaxel (Taxol®) in individuals with metastatic breast cancer (MBC). This phase III study was performed to confirm the preclinical studies demonstrating superior efficacy and reduced toxicity of ABI-007 when compared with Taxol®. Individuals were randomly assigned to 3-week cycles of either ABI-007 260 mg/m$^2$ (iv) over 30 minutes without premedication (n=229) or Taxol® 175 mg/m$^2$ IV over 3 hours with premedication (n=225). ABI-007 demonstrated significantly higher response rates compared with Taxol® (33% vs. 19%; p=0.001) and significantly longer time to tumor progression (23.0 vs. 16.9 weeks; HR=0.75; p=0.006). There was a trend for longer overall survival in individuals who received ABI-007 (65.0 vs. 55.7 weeks; p=0.374). In an unplanned analysis, ABI-007 improved survival in individuals receiving treatment as second- or greater-line therapy (56.4 vs. 46.7 weeks; HR=0.73; p=0.024). The incidence of grade 4 neutropenia was significantly lower in the ABI-007 group (9% vs. 22%; p<0.001) despite a 49% higher paclitaxel dose. Grade 3 sensory neuropathy was more common in the ABI-007 group than in the Taxol® group (10% vs. 2%; p<0.001) but was easily managed and improved more rapidly (median, 22 days) than for Taxol® (median 73 days). No severe (grade 3 or 4) treatment-related hypersensitivity reactions occurred in any of the individuals in the ABI-007 group despite the absence of premedication and shorter administration time. In contrast, grade 3 hypersensitivity reactions occurred in the Taxol® group despite standard premedication (chest pain: 2 individuals; allergic reaction: 3 individuals). Per protocol, corticosteroids and antihistamines were not administered routinely to individuals in the ABI-007 group; however, premedication was administered for emesis, myalgia/arthralgia, or anorexia in 18 individuals (8%) in the ABI-007 group in 2% of the treatment cycles, whereas 224 individuals (>99%) in the Taxol® group received premedication at 95% of the cycles. The only clinical chemistry value that was notably different between the 2 treatment arms was higher serum glucose levels in the Taxol®-treated individuals, who also had a higher incidence of hyperglycemia reported as an AE (adverse effects) (15 [7%] vs. 3 [1%]; p=0.003). Overall, ABI-007 demonstrated greater efficacy and a favorable safety profile compared with Taxol® in this individual population. The improved therapeutic index and elimination of the steroid premedication required for solvent-based taxanes make this nanoparticle albumin-bound paclitaxel an important advance in the treatment of MBC.

Example 3

Weekly Abraxane® in Taxane-Refractory Metastatic Breast Cancer Individuals

A recent Phase II clinical study showed that weekly administration of Abraxane® (nanoparticle albumin-bound paclitaxel) at a dose of 125 mg/m$^2$ resulted in long-term disease control in individuals with metastatic breast cancer whose disease had progressed while being treated with Taxol® or Taxotere® (that is, individuals who are taxane-refractory).

Abraxane® is believed to represent the first biologically interactive composition that exploits the receptor-mediated (gp60) pathway found to be integral to achieving high intracellular tumor concentrations of the active ingredient—paclitaxel. The Phase II study included 75 individuals with taxane-refractory metastatic breast cancer. Abraxane® was administered weekly via a 30-minute infusion at 125 mg/m$^2$ without steroid/antihistamine premedication or G-CSF prophylaxis. Individuals received three weekly doses followed by one week of rest, repeated every 28 days. Unlike Taxol® or Taxotere®, which contain detergents that may inhibit tumor uptake, the mechanism of action of the albumin-bound nanoparticle paclitaxel may result in improved outcomes, especially in this difficult-to-treat individual population.

Specifically, the data showed that despite this high weekly dose of 125 mg/m$^2$ in this highly pre-treated and prior taxane-exposed individual population, only 3 of 75 individuals (4%) had to discontinue Abraxane® due to peripheral neuropathy. Furthermore, of those who experienced Grade 3 peripheral neuropathy, 80% were typically able to resume treatment after a delay of only 1 or 2 weeks and continued to receive Abraxane® at a reduced dose for an average of 4 additional months. This rapid improvement was consistent with our observation from the Phase III trial—that the peripheral neuropathy induced by paclitaxel alone (i.e., without Cremophor®) improves rapidly as compared to that induced by Taxol®. These Abraxane® clinical trial experiences provide the first clinical opportunity to evaluate the effects of the chemotherapeutic agent itself, paclitaxel, from the effects from those of solvents. Based upon both the Phase II and III experience, the data now suggest that the peripheral neuropathy from Abraxane® is not comparable to the peripheral neuropathy from Taxol® or Taxotere® with respect to duration and impact on the individual.

With regard to the clinical experience of peripheral neuropathy following Taxol® or Taxotere®, Abraxis Oncology recently completed a survey of 200 oncologists who were asked how long they thought the peripheral neuropathy induced by Taxol® took to improve and/or resolve: 25% reported "7-12 months" and another 23% reported "never resolved"; for Taxotere®, the respective percentages were 29% and 7%. These data are consistent with the statements in the Taxotere® and Taxol® package inserts.

Analysis of the Phase II data demonstrates Abraxane® to be active in this poor-prognosis individual population (87% visceral (lung and liver) disease, 69%>3 metastatic sites, 88% tumor growth while on taxanes), of taxane-refractory individuals with metastatic breast cancer. Observations included a 44% disease control in Taxotere®-refractory individuals and 39% disease control in Taxol'-refractory individuals. Of those individuals whose disease progressed while on Taxotere® alone in the metastatic setting (n=27) a 19% response rate was noted after receiving weekly Abraxane®. Of those individuals whose disease progressed while on Taxol® alone in the metastatic setting (n=23) a 13% response rate was noted after receiving weekly Abraxane®.

Abraxane® was found to be well tolerated when administered weekly over 30 minutes without steroids or G-CSF prophylaxis: Grade 4 neutropenia=3% (without G-CSF); Grade 4 anemia=1%; no severe hypersensitivity reactions (despite absence of premedication). In this heavily pre-treated individual population, 75% of individuals were treated at the full high dose of 125 mg/m$^2$ weekly Abraxane®, with no dose reductions due to toxicities/adverse events. Of the individuals who developed grade 3 sensory neuropathy, 77% were able to restart Abraxane® at a reduced dose (75-100 mg/m$^2$) and received a mean of 12.2 (range, 1-28) additional doses of Abraxane®. It was remarkable to note that of these individuals who resumed Abraxane®, 80% (8 of 10) were able to restart the drug within 14 days after improvement of neuropathy to Grade 1 or 2. These results support the observations in the pivotal Phase III trial of 260 mg/m$^2$ Abraxane® administered every 3 weeks, in which rapid improvement of neuropathy (median of 22 days) was also noted. Taken together these two clinical trials suggest when paclitaxel is given alone, the neuropathy which occurs appears to be short-lived and is easily managed.

Abraxane® utilizes the gp60 receptor based pathway on the microvessel endothelial cells to transport the albumin-paclitaxel complex out of the blood vessel and into the tumor interstitium, and it has been shown that Taxol® was not transported by this mechanism. Furthermore, an albumin-binding protein, SPARC, was over-expressed in breast tumors and may play a role in the increased intra-tumoral accumulation of Abraxane®. The proposed mechanism suggested that once in the tumor interstitium, the albumin-paclitaxel complex would bind to SPARC that was present on the tumor cell surface and be rapidly internalized into the tumor cell by a non-lysosomal mechanism.

In addition, the surfactants/solvents commonly used in current taxane formulations such as Cremophor®, Tween® 80 and TPGS, strongly inhibit the binding of paclitaxel to albumin, thereby limiting transendothelial transport. Additional data presented showed a statistically improved efficacy of Abraxane® over Taxotere® in the MX-1 mammary breast carcinoma xenograft at equal dose.

In conclusion, 75% of individuals were treated at fill high dose with no dose reductions. Data indicate rapid improvement of peripheral neuropathy when nanoparticle albumin-bound paclitaxel is administered alone, without the solvent Cremophor®. Additional data provide increased evidence that mechanism of action may play important role in enhancing individual outcomes.

Example 4

Abraxane® (ABI-007) Acts Synergistically with Targeted Antiangiogenic Pro-Apoptotic Peptides (HKP) in MBA-MB-435 Human Tumor Xenografts The antiangiogenic activity of small synthetic pro-apoptotic peptides composed of two functional domains, one targeting the CD13 receptors (aminopeptidase N) on tumor microvessels and the other disrupting the mitochondrial membrane following internalization have previously been reported. See Nat Med. 1999 September; 5(9): 1032-8. A second generation dimeric peptide, CNGRC-GG-d(KLAK-LAK)$_2$, named HKP (Hunter Killer Peptide) was found to have improved antitumor activity. Since anti-angiogenic agents such as Avastin® exhibit synergism in combination with cytotoxic agents such as 5-fluorouracil, we evaluated the combination of the antiangiogenic HKP with Abraxane® (ABI-007), an albumin nanoparticle paclitaxel that is transported by the gp60 receptor in vascular endothelium (Desai, SABCS 2003), in MDA-MB-435 human breast tumor xenografts.

Methods: MDA-MB-435 human tumor xenografts were established at an average tumor volume of 100 mm$^3$, mice were randomized into groups of 12-13 animals and treated with HKP, Abraxane®, or HKP and Abraxane®. HKP was delivered i.v. (250 ug), once a week, for 16 weeks. Abraxane® was administered i.v., daily for 5 days at 10 mg/kg/day only for the first week of treatment. The Abraxane® dose used was substantially below its MTD (30 mg/kg/day, qd×5) to prevent the tumor from complete regression so effect of HKP could be noted.

Results: At nineteen weeks of treatment, tumor volume was significantly decreased between control group (10,298 mm$^3$±2,570) and HKP (4,372 mm$^3$±2,470; p<0.05 vs control) or ABI-007 (3,909 mm$^3$±506; p<0.01 vs control). The combination of ABI-007 and HKP significantly reduced the tumor volume over either monotherapy (411 mm$^3$±386; p<0.01 vs. Abraxane® monotherapy or HKP monotherapy). The treatments were well tolerated.

Conclusion: The combination of Abraxane® (ABI-007), a nanoparticle albumin-bound paclitaxel, with the vascular targeting anti-angiogenic dimeric peptide HKP (CNGRC-GG-d(KLAKLAK)$_2$) against the MDA-MB-435 xenograft breast tumor showed a significant reduction in tumor volume compared to monotherapy of either agent alone. Our results suggest that the combination of Abraxane® with antiangiogenic agents such as HKPs or perhaps Avastin® may be beneficial.

Example 5

Metronomic ABI-007 Therapy: Antiangiogenic and Antitumor Activity of a Nanoparticle Albumin-Bound Paclitaxel Example 5a Methods: The antiangiogenic activity of ABI-007 was assessed by the rat aortic ring, human umbilical vein endothelial cell (HUVEC) proliferation and tube formation assays. Optimal dose of ABI-007 for metronomic therapy was determined by measuring the levels of circulating endothelial progenitors (CEPs) in peripheral blood of Balb/c non-tumor bearing mice (n=5/group; dosing: 1-30 mg/kg, i.p, qd×7) with flow cytometry (Shaked et al., *Cancer Cell* 7: 101-111 (2005)). Subsequently, the antitumor effects of metronomic (qd; i.p.) and MTD (qd×5, 1 cycle; i.v.) ABI-007 and Taxol® were evaluated and compared in SCID mice bearing human MDA-MD-231 breast and PC3 prostate cancer xenografts.

Results: ABI-007 at 5 nM significantly (p<0.05) inhibited rat aortic microvessel outgrowth, human endothelial cell proliferation and tube formation by 53%, 24%, and 75%, respectively. The optimal dose of ABI-007 for metronomic therapy was observed to be 6-10 mg/kg based on CEP measurements. Metronomic ABI-007 (6 mg/kg) but not Taxol® (1.3 mg/kg) significantly (p<0.05) suppressed tumor growth in both xenograft models. Neither ABI-007 nor Taxol® administered metronomically induced any weight loss. Although MTD ABI-007 (30 mg/kg) inhibited tumor growth more effectively than MTD Taxol® (13 mg/kg), significant weight loss was noted with the former. Interestingly, the antitumor effect of metronomic ABI-007 approximated that of MTD Taxol®.

Conclusion: ABI-007 exhibits potent antiangiogenic and antitumor activity when used in a metronomic regime.

Example 5b

Rat Aortic Ring Assay. Twelve-well tissue culture plates were coated with Matrigel (Collaborative Biomedical Products, Bedford, Mass.) and allowed to gel for 30 min at 37° C. and 5% $CO_2$. Thoracic aortas were excised from 8- to 10-week-old male Sprague-Dawley rats, cut into 1-mm-long cross-sections, placed on Matrigel-coated wells and covered with an additional Matrigel. After the second layer of Matrigel had set, the rings were covered with EGM-II and incubated overnight at 37° C. and 5% $CO_2$. EGM-II consists of endothelial cell basal medium (EBM-II; Cambrex, Walkersville, Md.) plus endothelial cell growth factors provided as the EGM-II Bulletkit (Cambrex). The culture medium was subsequently changed to EBM-II supplemented with 2% FBS, 0.25 µg/ml amphotericin B and 10 µg/ml gentamycin. Aortic rings were treated with EBM-II containing the vehicle (0.9% saline/albumin), carboxyamidatriazole (CAI; 12 µg/ml), or ABI-007 (0.05-10 nM paclitaxel) for 4 days and photographed on the fifth day. CAI, a known antiangiogenic agent, was used at a higher than clinically achievable concentration as a positive control. Experiments were repeated four times using aortas from four different rats. The area of angiogenic sprouting, reported in square pixels, was quantified using Adobe Photoshop 6.0.

Figure 1A:
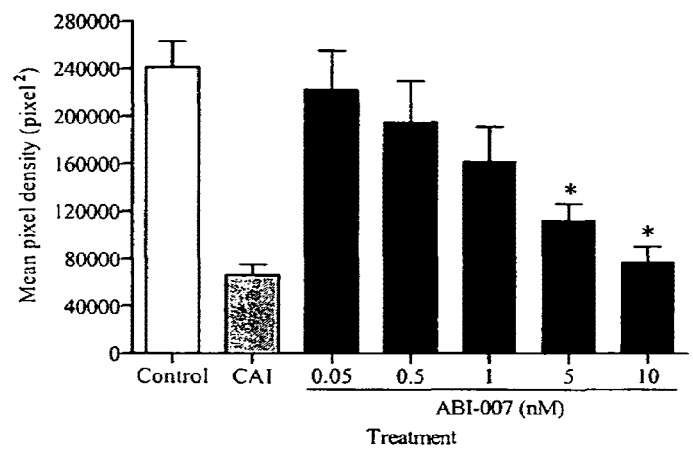
FIG. 1A shows the effect of ABI-007 on rat aortic ring angiogenesis.

As shown in FIG. 1A, ABI-007 significantly inhibited rat aortic microvessel outgrowth in a concentration-dependent manner relative to the vehicle control, reaching statistical significance (p<0.05) at 5 nM (53% inhibition) and 10 nM (68% inhibition). The amount of albumin present at each concentration of ABI-007 alone did not inhibit angiogenesis.

Endothelial Cell Proliferation Assay. Human umbilical vein endothelial cells (HUVEC; Cambrex) were maintained in EGM-II at 37° C. and 5% CO2. HUVECs were seeded onto 12-well plates at a density of 30,000 cells/well and allowed to attach overnight. The culture medium was then aspirated, and fresh culture medium containing either the vehicle (0.9% saline/albumin), or ABI-007 (0.05-10 nM paclitaxel) was added to each well After 48 h, cells were trypsinized and counted with a Coulter Z1 counter (Coulter Corp., Hialeah, Fla.). All experiments were repeated three times.

Figure 1B:
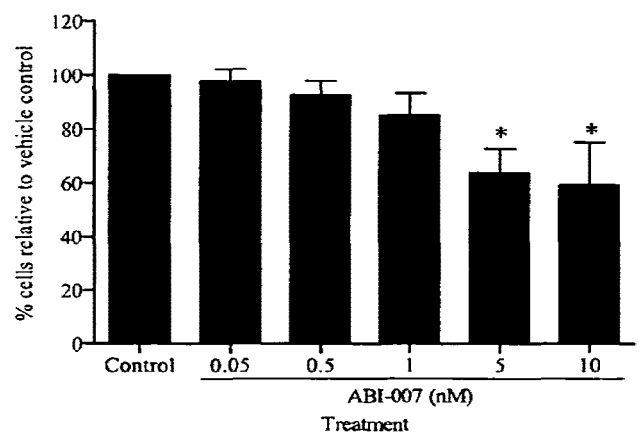
FIG. 1B shows the effect of ABI-007 on human endothelial cell proliferation.

As shown in FIG. 1B, human endothelial cell proliferation was significantly inhibited by ABI-007 at 5 nM and 10 nM by 36% and 41%, respectively.

Endothelial Cell Tube Formation Assay. Eight-well slide chambers were coated with Matrigel and allowed to gel at 37° C. and 5% $CO_2$ for 30 min. HUVECs were then seeded at 30,000 cells/well in EGM-II containing either the vehicle (0.9% saline/albumin) or ABI-007 (0.05-10 nM paclitaxel) and incubated at 37° C. and 5% $CO_2$ for 16 h. After incubation, slides were washed in PBS, fixed in 100% methanol for 10 s, and stained with DiffQuick solution II (Dade Behring Inc., Newark, Del.) for 2 min. To analyze tube formation, each well was digitally photographed using a 2.5× objective. A threshold level was set to mask the stained tubes. The corresponding area was measured as the number of pixels using MetaMorph software (Universal Imaging, Downingtown, Pa.). Experiments were repeated three times.

Figure 1C:
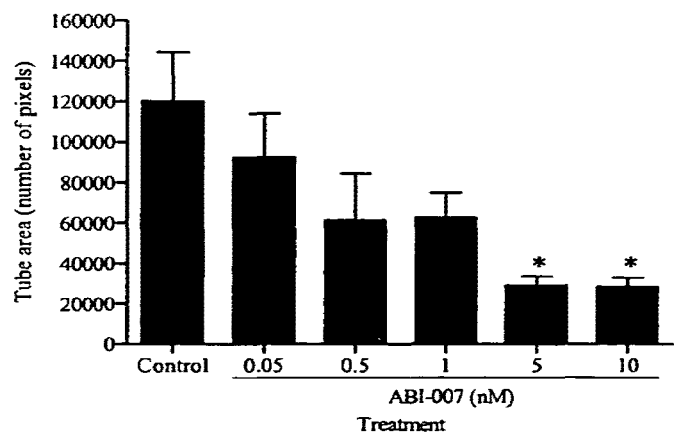
FIG. 1C shows the effect of ABI-007 on endothelial cell tube formation.

As shown in FIG. 1C, ABI-007 blocked tube formation by 75% at both 5 nM and 10 nM.

Determination of the In Vivo Optimal Biologic Dose of ABI-007 by Measuring Circulating Endothelial Cells (CECs) and Circulating Endothelial Progenitors (CEPs). Six- to eight-week-old female Balb/cJ mice were randomized into the following eight groups (n=5 each): untreated, treated with i.p. bolus injections of either the drug vehicle (0.9% saline/albumin), or ABI-007 at 1, 3, 6, 10, 15 or 30 mg/kg paclitaxel daily for 7 days. At the end of the treatment period, blood samples were drawn by cardiac puncture and collected in EDTA-containing vacutainer tubes (Becton Dickinson, Franklin Lakes, N.J.). CECs and CEPs were enumerated using four-color flow cytometry. Monoclonal antibodies specific for CD45 were used to exclude CD45+ hematopoietic cells. CECs and their CEP subset were depicted using the murine endothelial markers fetal liver kinase 1/VEGF receptor 2 (flk-1/VEGFR2), CD13, and CD117 (BD Pharmingen, San Diego, Calif.). Nuclear staining (Procount; BD Biosciences, San Jose, Calif.) was performed to exclude the possibility of platelets or cellular debris interfering with the accuracy of CEC and CEP enumeration. After red cell lysis, cell suspensions were evaluated by a FACSCalibur (BD Biosciences) using analysis gates designed to exclude dead cells, platelets, and debris. At least 100,000 events/sample were obtained in order to analyze the percentage of CECs and CEPs. The absolute number of CECs and CEPs was then calculated as the percentage of the events collected in the CEC and CEP enumeration gates multiplied by the total white cell count. Percentages of stained cells were determined and compared to the appropriate negative controls. Positive staining was defined as being greater than non-specific background staining. 7-aminoactinomycin D (7AAD) was used to enumerate viable versus apoptotic and dead cells.

Figure 2:
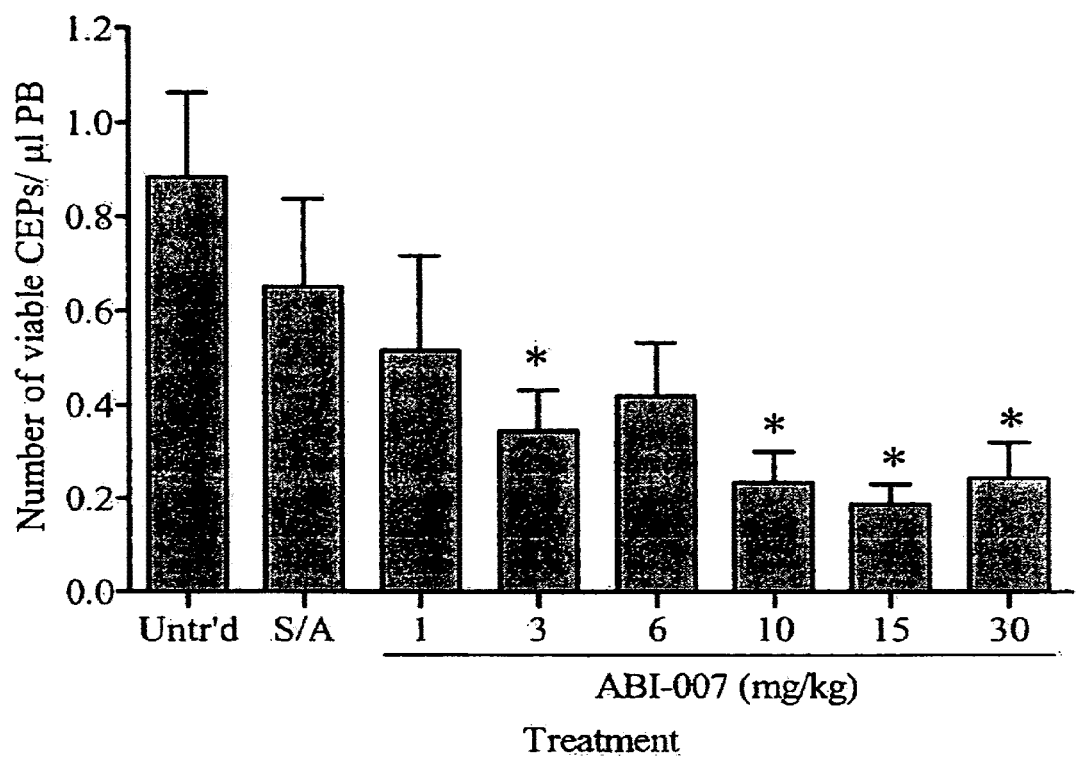
FIG. 2 shows the determination of an optimal biological dose of ABI-007 for metronomic dosing. Shown are the levels of viable circulating endothelial progenitors (CEPs) in peripheral blood of Balb/cJ mice in response to escalating doses of ABI-007. Untr'd, untreated control; S/A, saline/albumin vehicle control. Bars, mean±SE. * Significantly (p<0.05) different from the untreated control.

FIG. 2 shows that ABI-007 administered i.p. daily for 7 days at 3, 10-30 mg/kg significantly decreased CEP levels in non-tumor bearing Balb/cJ mice. However, ABI-007 at 10-30 mg/kg was associated with a significant reduction of white blood cell count indicative of toxicity. Although the reduction of CEP levels by ABI-007 at 6 mg/kg did not reach statistical significance, decrease in white blood cell count was not evident. Therefore it was concluded that the in vivo optimal biologic dose for metronomic ABI-007 was between 3-10 mg/kg. In one study, metronomic Taxol® at 1.3, 3, 6, or 13 mg/kg given i.p. daily for 7 days did not significantly reduce viable CEP levels, whereas metronomic Taxol® at 30 mg/kg or higher resulted in severe toxicity and eventually mortality in mice. It was previously reported that the i.p. administration of Taxol® at doses commonly used in the clinic resulted in entrapment of paclitaxel in Cremophor® EL micelles in the peritoneal cavity and consequently, insignificant plasma paclitaxel concentration (Gelderblom et al., Clin. Cancer Res. 8:1237-41 (2002)). This would explain why doses of metronomic Taxol® (1.3, 3, 6, and 13 mg/kg) that did not cause death failed to change viable CEP levels. In this case, the i.p. administration of metronomic Taxol® at 1.3 mg/kg would not be any different from that at 13 mg/kg. Therefore the lower dose, 1.3 mg/kg, was selected to minimize the amount of Cremophor® EL per paclitaxel administration for subsequent experiments.

Antitumor effects of metronomic and MTD ABI-007 compared with metronomic and MTD Taxol®. Human prostate cancer cell line PC3 and human breast cancer cell line MDA-MD-231 were obtained from the American Type Culture Collection (Manassas, Va.). PC3 cells ($5 \times 10^6$) were injected s.c. into 6- to 8-week-old male SCID mice, whereas MDA-MB-231 cells ($2 \times 10^6$) were implanted orthotopically into the mammary fat pad of female SCID mice. When the primary tumor volume reached approximately 150-200 $mm^3$, animals were randomized into eight groups (n=5-10/group). Each group was treated with either 0.9% saline/albumin vehicle control, Cremophor® EL vehicle control, metronomic Taxol® (1.3 mg/kg, i.p., qd), metronomic ABI-007 (3, 6, or 10 mg/kg paclitaxel, i.p., qd), MTD Taxol® (13 mg/kg, i.p., qd×5, 1 cycle), or MTD ABI-007 (30 mg/kg paclitaxel, i.v., qd×5, 1 cycle). Perpendicular tumor diameters were measured with a caliper once a week and their volumes were calculated. At the end of the treatment period, blood samples were drawn by cardiac puncture from mice in all groups. CECs and CEPs were enumerated as described herein.

Figure 3A:
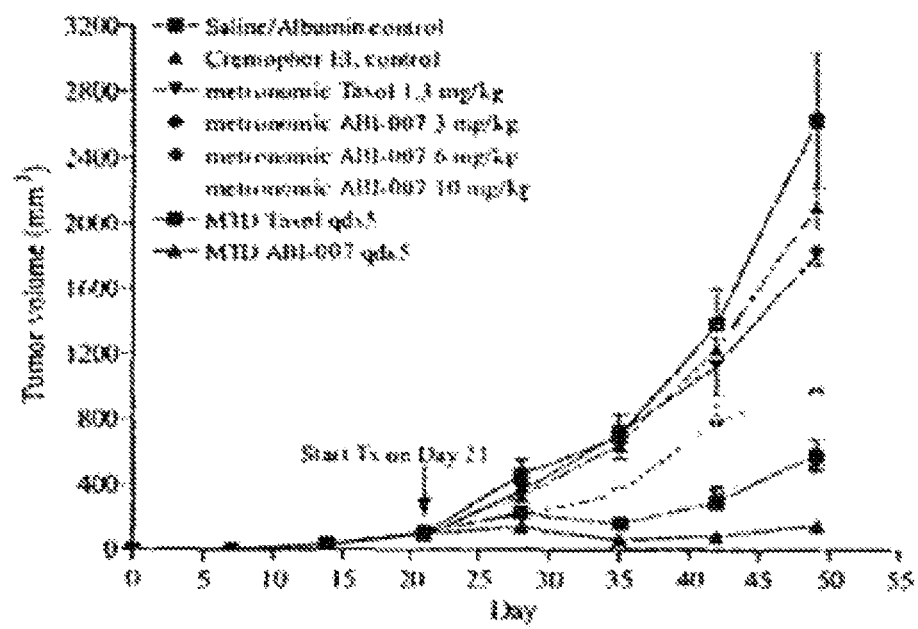
Figure 3C:
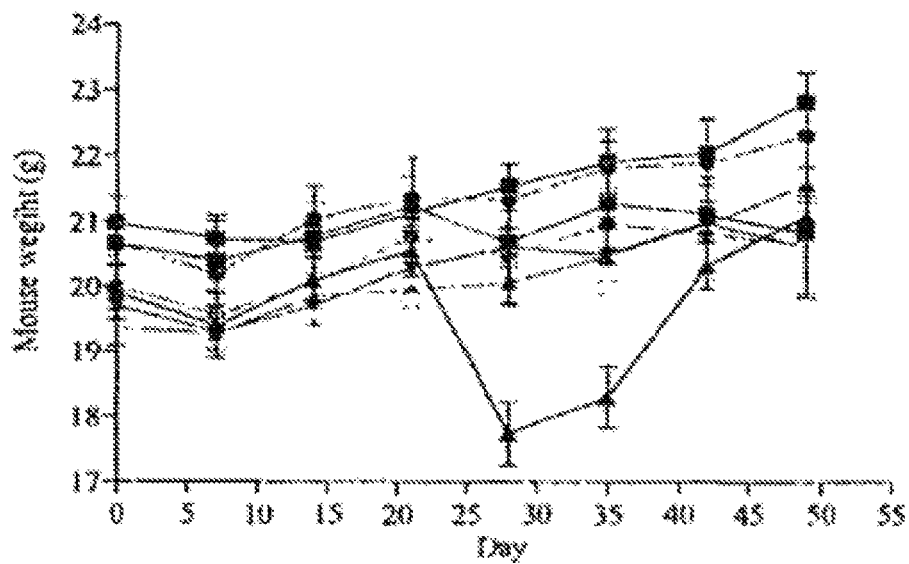

Metronomic ABI-007 (3, 6 and 10 mg/kg) but not Taxol® (1.3 mg/kg) administered i.p. daily for 4 weeks significantly ($p<0.05$) inhibited growth of both MDA-MB-231 and PC3 tumors (FIG. 3A and FIG. 3B). Neither ABI-007 nor Taxol® administered metronomically induced any weight loss (FIG. 3C and FIG. 3D). Although MTD ABI-007 (30 mg/kg) inhibited tumor growth more effectively than MTD Taxol® (13 mg/kg), significant weight loss was noted with the former, indicating toxicity. In addition, two out of five mice treated with MTD ABI-007 displayed signs of paralysis in one limb 6 days after the last dose of drug. The paralysis was transient and resolved within 24-48 hours. Interestingly, the antitumor effect of metronomic ABI-007 at 6 mg/kg approximated that of MTD Taxol® in the MDA-MB-231 xenograft model (FIG. 3A). Increasing the dose of metronomic ABI-007 to 10 mg/kg did not seem to confer more pronounced tumor growth inhibition. In contrast, metronomic ABI-007 elicited greater antitumor response at 10 mg/kg than at 3 and 6 mg/kg in the PC3 xenografts (FIG. 3B).

Figure 4A:
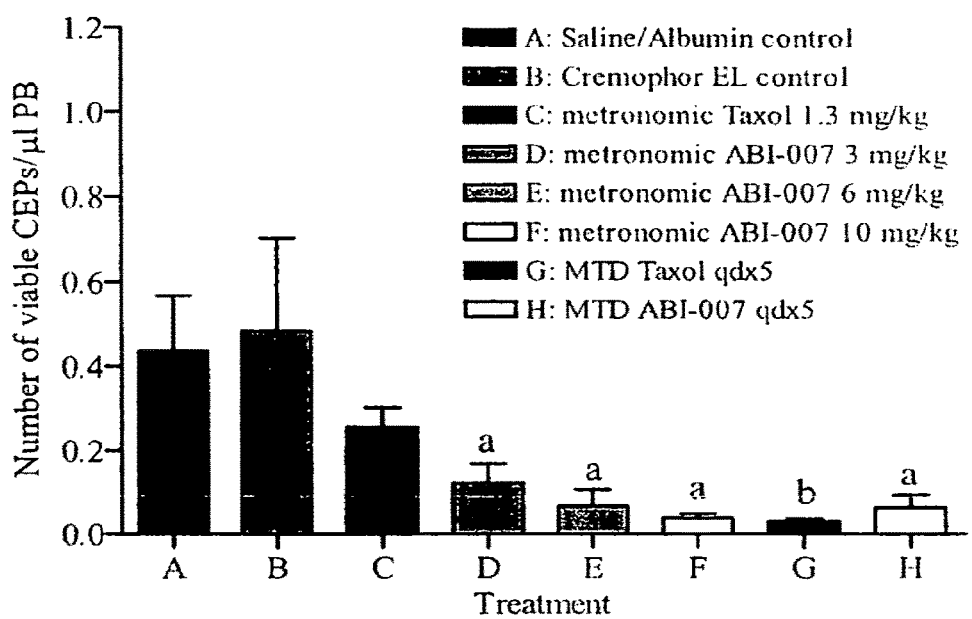
FIGS. 4A and 4B show changes in the levels of viable circulating endothelial progenitors (CEPs) in peripheral blood of MDA-MB-231 (FIG. 4A) and PC3 (FIG. 4B) tumor-bearing SCID mice after treatment with A, saline/albumin; B, Cremophor EL control; C, metronomic Taxol® 1.3 mg/kg; D, E, and F, metronomic ABI-007 3, 6, and 10 mg/kg, respectively; G, MTD Taxol®; H, MTD ABI-007.
Figure 4B:
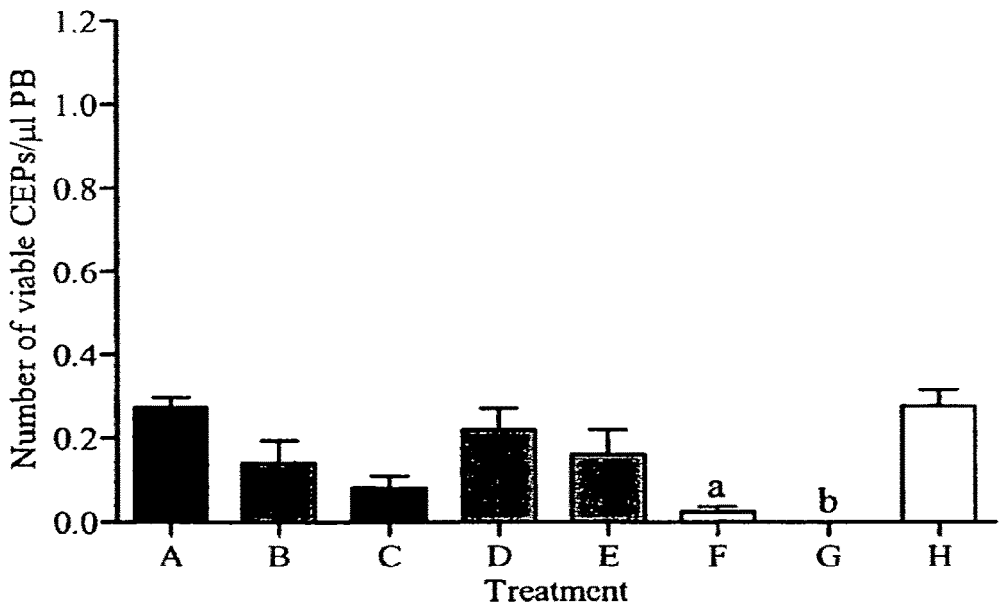

Metronomic ABI-007 significantly decreased the levels of viable CEPs in a dose-dependent manner in MDA-MB-231 tumor-bearing mice (FIG. 4A). Viable CEP levels also exhibited a dose-dependent reduction in response to metronomic ABI-007 in PC3 tumor-bearing mice, but reached statistical significance only at 10 mg/kg (FIG. 4B). The levels of CEPs were not altered by metronomic Taxol® in both xenograft models (FIGS. 4A and 4B).

Effects of metronomic and MTD ABI-007 and metronomic and MTD Taxol® on intratumoral microvessel density were studied. Five-um thick sections obtained from frozen MDA-MB-231 and PC3 tumors were stained with H&E for histological examination by standard methods known to one skilled in the art. For detection of microvessels, sections were stained with a rat anti-mouse CD31/PECAM-1 antibody (1:1000, BD Pharmingen) followed by a Texas Red-conjugated goat anti-rat secondary antibody (1:200, Jackson ImmunoResearch Laboratories, Inc., West Grove, Pa.). A single microvessel was defined as a discrete cluster or single cell stained positive for CD31/PECAM-1d, and the presence of a lumen was not required for scoring as a microvessel. The MVD for each tumor was expressed as the average count of the three most densely stained fields identified with a 20× objective on a Zeiss AxioVision 3.0 fluorescence microscopic imaging system. Four to five different tumors per each vehicle control or treatment group were analyzed.

In MDA-MB-231 tumors, metronomic ABI-007 at 6 and 10 mg/kg as well as MTD ABI-007 seemed to reduce microvessel density (MVD) slightly although statistical significance was not reached (FIG. 5A). In PC3 tumors, metronomic ABI-007 at 3 and 10 mg/kg appeared to decrease MVD but without reaching statistical significance (FIG. 5A). Interestingly, a significant correlation existed between MVD and the level of viable CEPs in the MDA-MB-231 (FIG. 5B; r=0.76, P-0.04) but not in the PC3 (FIG. 5C; r=−0.071, P-0.88) model.

In vivo angiogenesis evaluation were carried out. A Matrigel plug perfusion assay was performed with minor modifications to methods known by one skilled in the art. Briefly, 0.5 ml Matrigel supplemented with 500 ng/ml of basic fibroblast growth factor (bFGF; R&D Systems Inc., Minneapolis, Minn.) was injected s.c. on day 0 into the flanks of 10-week-old female Balb/cJ mice. On day 3, animals were randomly assigned to eight groups (n=5 each). Each group was treated with either 0.9% saline/albumin vehicle control, Cremophor® EL vehicle control, metronomic Taxol® (1.3 mg/kg, i.p., qd), metronomic ABI-007 (3, 6, or 10 mg/kg paclitaxel, i.p., qd), MTD Taxol® (13 mg/kg, i.v., qd×5), or MTD ABT-007 (30 mg/kg paclitaxel, i.v, qd×5). As a negative control, five additional female Balb/cJ mice of similar age were injected with Matrigel alone. On day 10, all animals were injected i.v. with 0.2 ml of 25 mg/ml FITC-dextran (Sigma, St. Louis, Mo.). Plasma samples were subsequently collected. Matrigel plugs were removed, incubated with Dispase (Collaborative Biomedical Products, Bedford, Mass.) overnight at 37° C., and then homogenized. Fluorescence readings were obtained using a FL600 fluorescence plate reader (Biotech Instruments, Winooski, Vt.). Angiogenic response was expressed as the ratio of Matrigel plug fluorescence to plasma fluorescence.

Metronomic ABI-007 at 6 and 10 mg/kg appeared to decrease angiogenesis although the inhibition did not reach statistical significance (FIG. 6). Angiogenesis seemed to be unaltered by metronomic ABI-007 at 3 mg/kg, MTD ABI-007, MTD and metronomic Taxol® relative to the respective vehicle controls (FIG. 6). These observations were similar to the intratumoral MVD results described herein.

Example 6

Abraxane® vs Taxotere®: A Preclinical Comparison of Toxicity and Efficacy

Methods: Toxicity of Abraxane® and Taxotere® was compared in a dose-ranging study in nude mice given the drugs on a q4d×3 schedule. The dose levels were Taxotere® 7, 15, 22, 33, and 50 mg/kg and ABX 15, 30, 60, 120, and 240 mg/kg. Antitumor activity of Abraxane® and Taxotere® was compared in nude mice with human MX-1 mammary xenografts at a dose of 15 mg/kg weekly for 3 weeks.

Results: In the dose-escalation study in mice, the Taxotere® maximum tolerated dose (MTD) was 15 mg/kg and lethal dose ($LD_{100}$) was 50 mg/kg. In contrast, the Abraxane® MTD was between 120 and 240 mg/kg and $LD_{100}$ was 240 mg/kg. In the tumor study Abraxane® was more effective than equal doses of Taxotere® in tumor growth inhibition (79.8% vs 29.1%, p<0.0001, ANOVA).

Conclusion: Nanoparticle abuinin-bound paclitaxel (Abraxane®) was superior to Taxotere® in the MX-1 tumor model when tested at equal doses. Furthermore, the toxicity of Abraxane® was significantly lower than that of Taxotere®, which would allow dosing of Abraxane® at substantially higher levels. These results are similar to the enhanced therapeutic index seen with Abraxane® compared to Taxol® and suggest that the presence of surfactants may impair the transport, antitumor activity and increase the toxicity of taxanes. Studies in additional tumor models comparing Abraxane® and Taxotere® are ongoing.

Example 7

Combination Studies of Abraxane® and Other Agents

Due to the advantageous properties of Abraxane® (ABX, the nanoparticle albumin-bound paclitaxel) noted above, it was used and being used in a number of studies with different modes of administration and schedules and in combination with other oncology drugs as well as radiation treatment. These are listed below:

In metastatic breast cancer, these studies include:

| | | |
|---|---|---|
| Randomized Phase II Trial of Weekly Abraxane ® in Combination with Gemcitabine in Individuals with HER2 Negative Metastatic Breast Cancer | ABX 125, Gem 1000 mg/m$^2$, D1, 8; q 3wk | To evaluate the combination of ABX and Gemcitabine in 1st-line MBC. |
| A phase II study of weekly dose-dense nanoparticle paclitaxel (ABI-007) carboplatin, with Herceptin ® as first or second-line therapy of advanced HER2 positive breast cancer | ABX 100 mg/m$^2$, Carbo AUC 2, both D1, 8, 15; Her 2 mg/kg (4 mg/kg on wk a) q4wk × 6 | Data will be important for using ABX in combination with carbo and/or Herceptin ®. Also helpful for other combinations. |
| Weekly Vinorelbine and Abraxane ®, with or without G-CSF, in stage IV breast cancer: a phase I-II study | L1: ABX 80, Nav 15; L2: ABX 90, Nav 20; L3: ABX 100, Nav 22.5; L4: ABX 110, Nav 25; L5: ABX 125, Nav 25 qwk | Multi-center study of ABX in combination with Navelbine ® in 1st-line MBC. |

-continued

| | | |
|---|---|---|
| Phase II trial of weekly Abraxane ® monotherapy for 1st-line MBC (plus Herceptin ® in Her2+ pts) | ABX 125 mg/m² Q3/4wk | A relatively large phase II of weekly ABX monotherapy at 125 mg/m² in 1st-line MBC. |
| Phase I/II trial Abraxane ® plus Doxil ® for MBC plus limited PK | ABX + Anthracycline | |
| 3-arm phase II trial in 1st-line MBC | ABX weekly (130 mg/m²) vs. q2wk (260 mg/m²) vs. q3wk (260 mg/m²) | To optimize ABX monotherapy regime for MBC |
| 3-arm phase II trial in 1st-line MBC 2nd-line MBC, with biological correlates analyses | ABX weekly vs. ABX q3wk vs. Taxol ® weekly | randomized ABX MBC trial to obtain important data: weekly ABX vs. weekly Taxol ®; weekly ABX vs. 3-weekly ABX; plus biomarker study (caveolin-1 and SPARC), combination of ABX and GW572016 (a dual EGFR inhibitor and one of the most promising new biological agents for BC). |
| Phase I/II Abraxane ® + GW572016 | TBD | |
| A phase I dose escalation study of a 2 day oral gefitinib chemosensitization pulse given prior to weekly Abraxane ® in individuals with advanced solid tumors | Abraxane ® 100 mg/m² weekly, 3 out of 4 weeks; Gefitinib starting at 1000 mg/d × 2 days | This phase I trial is to determine the safety and tolerability of a 2 day gefitinib pulse given prior to Abraxane ® administration. |
| Phase II 1$^{st}$ line MBC trial | weekly ABX (125 mg/m², 2 wk on and 1 wk off) + Xeloda ® 825 mg/m² d 1-14 q3wk | To evaluate the combination of ABX and Xeloda ® in 1st-line MBC, using 2 weekly on and 1 weekly off ABX regime. |
| Phase II pilot adjuvant trial of Abraxane ® in breast cancer | Dose dense AC + G CSF --> weekly ABX --> Avastin ® | A pilot: adjuvant study of a "super dose dense" |
| Abraxane ® in dose-dense adjuvant chemotherapy for early stage breast cancer | AC q2w × 4 + G CSF --> ABX q2wk × 4 | A pilot adjuvant study of dose dense ABX regime—an alternate of a standard adjuvant regime |
| Phase II pilot adjuvant trial of Abraxane ® in breast cancer | AC Q2wk --> ABX q2wk + G-CSF | A pilot adjuvant study in preparation for phase III adjuvant trial |

In Breast cancer neoadjuvant setting studies include:

| | | |
|---|---|---|
| Phase II Trial of Dose Dense Neoadjuvant Gemcitabine, Epirubicin, ABI-007 (GEA) in Locally Advanced or Inflammatory Breast Cancer | Neoadjuvant: Gem 2000, Epi 60, ABX 175 mg/m², Neul 6 mg SC, all D1 q2 wk × 6 Adjuvant: Gem 2000, ABX 220, Neul 6 mg D1 q2wk × 4 | This neoadjuvant study is based on the GET data from Europe which showed high activity. In the current regime, ABX will replace T, or Taxol ®. |
| Phase II preoperative trial of Abraxane ® followed by FEC (+Herceptin ® as appropriate) in breast cancer | ABX 220 mg/m2 q2wk × 6 followed by FEC × 4 (+Herceptin ® for Her2+ pts) | |
| Pre-clinical study of drug-drug interaction | ABX + other agents | |
| Phase II neoadjuvant | (ABX + Herceptin ®) followed by (Navelbine ® + Herceptin ®) | |
| Randomized phase II trial of neoadjuvant chemotherapy in individuals with breast cancer | TAC vs. AC followed ABX + carbo vs. AC followed ABX + carbo + Herceptin ® | To evaluate AC followed by ABX/carbo or ABX/carbo/Herceptin ® combinations vs TAC (a FDA approved adjuvant BC regime) in neoadjuvant setting. |
| Phase II neoadjuvant trial of Abraxane ® and capecitabine in locally advanced breast cancer | ABX: 200mg/m² D1, Xel: 1000 mg/m² D1-14; q3wk × 4 | |
| Phase II trial of neoadjuvant chemotherapy (NCT) with nanoparticle paclitaxel (ABI-007, Abraxane ®) in women with clinical stage IIA, IIB, IIIA, IIIB, and IV (with intact primary) breast cancers | ABX: 300 mg/m² q3wk | |

Studies in Chemoradiation include:

| | |
|---|---|
| Abraxane ® Combined With Radiation | animal model |

Other studies include:

| | |
|---|---|
| Ph II single treatment use of ABI-007 for the treatment of non-hematologic | | malignancies
Abraxane® Combined With
antiangiogenic agents, e.g., Avastin ®.
Abraxane ® Combined With proteasome
inhibitors e.g., Velcade ®.
Abraxane ® Combined With EGFR
inhibitors e.g., Tarceva ®.

Example 8

Combination of Abraxane® with Carboplatin and Herceptin®

The combination of Taxol® and carboplatin has shown significant efficacy against metastatic breast cancer. On a weekly schedule, in this combination, Taxol® can only be dosed at up to 80 mg/m$^2$. Higher doses cannot be tolerated due to toxicity. In addition, HER-2-positive individuals derive greater benefit when Herceptin® is included in their therapeutic regime. This open-label Phase II study was conducted to determine the synergistic therapeutic effect of ABI-007 (Abraxane®) with these agents. The current study was initiated to evaluate the safety and antitumor activity of ABI-007/carboplatin with Herceptin® for individuals with HER-2 positive disease. ABI-007 was given in combination with carboplatin and Herceptin® administered intravenously weekly to individuals with HER-2 positive advanced breast cancer. A cohort of 3 individuals received ABI-007 at a dose of 75 mg/m$^2$ IV followed by carboplatin at target AUC=2 weekly and Herceptin® infusion (4 mg/kg at week 1, and 2 mg/kg on all subsequent weeks) for 1 cycle. These individuals tolerated the drug very well so for all subsequent cycles and individuals the dose of ABI-007 was escalated to 100 mg/m$^2$. Six individuals were treated to date. Of the 4 individuals that were evaluated for response, all 4 (100%) showed a response to the therapy. It should be noted that due to lower toxicity of Abraxane®, a higher total paclitaxel dose could be given compared to Taxol® with resulting benefits to the individuals.

Example 9

Combination of Abraxane® and Tyrosine Kinase Inhibitors

Pulse-dosing of gefitinib in combination with the use of Abraxane® is useful to inhibit the proliferation of EGFR expressing tumors. 120 nude mice are inoculated with BT474 tumor cells to obtain at least 90 mice bearing BT474 xenograft tumors and split into 18 experimental arms (5 mice each). Arm 1 mice receive control i.v. injections. All other mice receive weekly i.v. injections of Abraxane® at 50 mg/kg for 3 weeks. Arm 2 receives Abraxane® alone. Arms 3, 4, 5, 6, 7, 8 receive weekly Abraxane® preceded by 2 days of a gefitinib pulse at increasing doses. Arms 9, 10, 11, 12, 13 receive weekly Abraxane® preceded by one day of a gefitinib pulse at increasing doses. Arms 14, 15, 16, 17, 18 receive weekly Abraxane® along with everyday administration of gefitinib at increasing doses. The maximum tolerated dose of gefitinib that can be given in a 1 or 2 day pulse preceding weekly Abraxane® or in continuous administration with Abraxane® is established. In addition, measurement of anti-tumor responses will determine whether a dose-response relationship exists and whether 2 day pulsing or 1 day pulsing is superior. These data are used to select the optimal dose of pulse gefitinib and that of continuous daily gefitinib given with Abraxane®.

120 nude mice are inoculated with BT474 tumor cells to obtain 90 mice bearing tumors. These mice are split into 6 groups (15 each). Arm 1 receive control i.v. injections. Arm 2 receives Abraxane® 50 mg/kg i.v. weekly for 3 weeks. Arm 3 receive oral gefitinib at 150 mg/kg/day. Arm 4 receive Abraxane® 50 mg/kg along with daily gefitinib at the previously established dose. Arm 5 receive Abraxane® 50 mg/kg preceded by a gefitinib pulse at the previously established dose and duration. Arm 6 receive only a weekly gefitinib pulse at the previously established dose. After three weeks of therapy, mice are followed until controls reach maximum allowed tumor sizes.

Example 10

Phase II Study of Weekly, Dose-dense Nab™-Paclitaxel (Abraxane®), Carboplatin With Trastuzumab® As First-line Therapy Of Advanced HER-2 Positive Breast Cancer This study aimed to evaluate (1) the safety and tolerability and (2) the objective response rate of weekly dose-dense trastuzumab/Abraxane®/carboplatin as first-line cytotoxic therapy for patients with advanced/metastatic (Stage IV adenocarcinoma) HER-2-overexpressing breast cancer. Trastuzumab is a monoclonal antibody, also known as Herceptin®, which binds to the extracellular segment of the erbB2 receptor.

Briefly, patients without recent cytotoxic or radiotherapy were included. Doses of Abraxane® were escalated from 75 mg/m$^2$ as 30-min i.v. infusions on days 1, 8, 15 up to 100 mg/m$^2$ for subsequent cycles according to the standard 3+3 rule. Carboplatin AUC=2 was given as 30-60 min i.v. infusions on days 1, 8, 15 and for an initial 29 day cycle. Trastuzumab was given as i.v. 30-90 min infusion on days 1, 8, 15, 22 at a dose of 4 mg/kg at week 1 and 2 mg/kg on all subsequent weeks.

Of 8 out of 9 patients evaluable for response the response rate (confirmed plus unconfirmed) was 63% with 38% stable disease. The most common toxicities were neutropenia (grade 3: 44%; grade 4: 11%) and leukocytopenia (33%).

These results suggest that trastuzumab plus Abraxane® plus carboplatin demonstrated a high degree of antitumor activity with acceptable tolerability as a first-line therapy for MBC.

Example 11

Phase II Trial of Capecitabine Plus Nab™-Paclitaxel (Abraxane®) in the First Line Treatment of Metastatic Breast Cancer The purpose of this phase II study was to evaluate the safety, efficacy (time to progression and overall survival), and quality of life of patients with MBC who received capecitabine in combination with Abraxane®. Capecitabine is a fluoropyrimidine carbamate also known as Xeloda® which has been shown to have substantial efficacy alone and in combination with taxanes in the treatment of MBC.

In this open-label, single-arm study, Abraxane® 125 mg/m$^2$ was given by i.v. infusion on day 1 and day 8 every 3 weeks plus capecitabine 825 mg/m$^2$ given orally twice daily on days 1 to 14 every 3 weeks. Patients were HER-2/neu negative with a life expectancy of greater than 3 months. Patients had no prior chemotherapy for metastatic disease, no prior capecitabine therapy, and no prior fluoropyrimidine therapy and paclitaxel chemotherapy given in an adjuvant setting. Over the course of the trial, 3 patients required a dose reduction of capecitabine to 650 mg/m$^2$, 2 patients required a dose reduction of capecitabine to 550 mg/m$^2$ and 3 patients required a dose reduction of Abraxane® to 100 mg/m$^2$.

The primary endpoint was objective response rate and safety/toxicity, with evaluation performed after every 2 cycles. A secondary endpoint was time to progression. 12 patients have been enrolled with safety analysis completed on the first 6 patients and the response rate evaluable after 2 cycles in the first 8 patients. There were no unique or unexpected toxicities with no grade 4 toxicities or neuropathy greater than grade 1. Response data were confirmed on only the first 2 cycles of therapy (first evaluation point) in 6 patients. Two patients have completed 6 cycles with 1 partial response and 1 stable disease. Of the first 8 patients after 2 cycles, there were 2 partial responses and 4 with stable disease.

Subsequently, a total of 50 patients were enrolled and 38 were available for analysis. Average age of the patients was 58.3 years (range of 24-84) and 50% of the patients had prior chemotherapy treatment (prior to metastatic disease). 34% of the patients had 1 metastatic site, 37% had 2 sites, 21% had 3 sites and 8% had more than 3 sites. The most common sites for metastases were the liver, bone, pulmonary tissue and other lymph nodes.

These results show that combination of capecitabine and weekly Abraxane® at effective doses is feasible with no novel toxicities to date. Abraxane® related toxicity was mainly neutropenia without clinical consequences, and hand foot syndrome was the major toxicity of capecitabine.

The clinical response was evaluated in 34 patients with 3 (9%) demonstrating complete response, 15 (44%) demonstrating partial response, 11 (32%) demonstrating stable disease and 5 (15%) demonstrating progressive disease. The combination of capecitabine and Abraxane was a very active combination regimen in first line metastatic breast cancer treatment. The results demonstrated a prolonged time to progression with this combination regimen.

Example 12

Pilot Study of Dose-Dense Doxorubicin Plus Cyclophosphamide Followed by Nab-Paclitaxel (Abraxane®) in Patients with Early-Stage Breast Cancer The objective of this study was to evaluate the toxicity of doxorubicin (adriamycin) plus cyclophosphamide followed by Abraxane® in early stage breast cancer.

Patients had operable, histologically confirmed breast adenocarcinoma of an early stage. The patients received doxorubicin (adriamycin) 60 mg/m$^2$ plus cyclophosphamide 600 mg/m$^2$ (AC) every 2 weeks for 4 cycles followed by Abraxane® 260 mg/m$^2$ every two weeks for 4 cycles.

30 patients received 4 cycles of AC, and 27 of 29 patients received 4 cycles of Abraxane®; 33% of patients received pegfilgrastim (Neulasta®) for lack of recovery of ANC (absolute neutrophil count) during Abraxane®. Nine patients (31%) had Abraxane® dose reductions due to non-hematologic toxicity. A total of 9 patients had grade 2 and 4 patients had grade 3 peripheral neuropathy (PN); PN improved by ≥1 grade within a median of 28 days.

These results indicate that dose-dense therapy with doxorubicin (60 mg/m$^2$) plus cyclophosphamide (600 mg/m$^2$) every 2 weeks for 4 cycles followed by dose-dense Abraxane® (260 mg/m$^2$) every 2 weeks for 4 cycles was well tolerated in patients with early-stage breast cancer.

Example 13

Weekly Nab-Paclitaxel (Abraxane®) as First Line Treatment of Metastatic Breast Cancer with Trastuzumab Add on for HER-2/Neu-Positive Patients The purpose of the current study was to move weekly Abraxane® to a front-line setting and add trastuzumab for HER2/neu-positive patients.

This phase II, open-label study included 20 HER2-positive and 50 HER2-negative patients with locally advanced or metastatic breast cancer. Abraxane® was given at 125 mg/m$^2$ by 30 minute i.v. infusion on days 1, 8, and 15 followed by a week of rest. Trastuzumab was given concurrently with study treatment for patients who were HER2-positive. The primary endpoint was response rate and the secondary endpoints were time to progression (TIP), overall survival (OS), and toxicity.

In the safety population, 23 patients received a median of 3 cycles of Abraxane® to date. The most common treatment-related adverse event was grade 3 neutropenia (8.7%) with no grade 4 adverse events. One out of 4 evaluable patients responded to therapy.

Example 14

Phase I Trial of Nab-Paclitaxel (Abraxane®) and Carboplatin

The aim of the current study was to determine the maximum tolerated dose of Abraxane® (both weekly and every 3 weeks) with carboplatin AUC=6 and to compare the effects of sequence of administration on pharmacokinetics (PK).

Patients with histologically or cytologically documented malignancy that progressed after "standard therapy" were included. Arm 1 received Abraxane® every 3 weeks in a dose escalation format based on cycle 1 toxicities (220, 260, 300, 340 mg/m$^2$) every 3 weeks followed by carboplatin AUC=6. Arm 2 received weekly (days 1, 8, 15 followed by 1 week off) Abraxane® (100, 125, 150 mg/m$^2$) followed by carboplatin AUC=6. For the PK portion of the study, Abraxane® was followed by carboplatin in cycle 1 and the order of administration reversed in cycle 2 with PK levels determined at initial 6, 24, 48 and 72 hours.

On the every 3 weeks schedule, neutropenia, thrombocytopenia and neuropathy were the most common grade 3/4 toxicities (3/17 each). On the weekly schedule, neutropenia 5/13 was the most common grade 3/4 toxicity. The best responses to weekly administration at the highest dose of 125 mg/m$^2$ (n=6) were 2 partial responses (pancreatic cancer, melanoma) and 2 stable disease (NSCLC). The best responses to the every three week administration at the highest dose of 340 mg/m$^2$ (n=5) were 1 stable disease (NSCLC) and 2 partial responses (SCLC, esophageal).

These data indicate activity of combination of Abraxane® and carboplatin. The MTD for the weekly administration was 300 mg/m$^2$, and for the once every 3 week administration was 100 mg/m$^2$.

Example 15

Phase II Trial of Dose-Dense Gemcitabine, Epirubicin, and Nab-Paclitaxel (Abraxane®) (GEA) in Locally Advanced/Inflammatory Breast Cancer Gemcitabine, anthracyclines and taxanes are among the most active agents in the treatment of breast cancer with metastatic breast cancer (MBC) trials confirming the high activity of this triplet. As neoadjuvant therapy, pathologic complete response (pCR) rates of 25% are evident with a variety of schedules. Previous neoadjuvant trial of gemcitabine, epirubicin and weekly docetaxel demonstrated a 24% pCR following 12 weeks of therapy although with prohibitive hematologic toxicity. Abraxane® is a novel taxane with superior responses, time to progression (TIP), and less myelosuppression than standard paclitaxel. Unique enhanced intratumoral concentrations for Abraxane® have been attributed to gp60 and SPARC glycoproteins. This trial examined the feasibility, toxicity, and efficacy of dose dense neoadjuvant combination therapy of gemcitabine, epirubicin and Abraxane® (GEA) in locally advanced breast cancer and/or inflammatory breast cancer. Primary objectives were to assess feasibility and toxicity of neoadjuvant GEA and to evaluate the clinical and pathological responses. The secondary objectives were to assess time to progression, overall survival and rate of breast conserving surgery.

In an open-label, phase II study an induction/neoadjuvant therapy regime was instituted prior to local intervention. The therapy regime was genicitabine 2000 mg/m$^2$ i.v. every 2 weeks for 6 cycles, epirubicin 50 mg/m$^2$ every 2 weeks for 6 cycles, Abraxane® 175 mg/m$^2$ every 2 weeks for 6 cycles, with pegfilgrastim 6 mg s.c. on day 2 every 2 weeks. The postoperative/adjuvant therapy regime after local intervention was gemcitabine 2000 mg/m$^2$ every 2 weeks for 4 cycles, Abraxane® 220 mg/m$^2$ every 2 weeks for 4 cycles and pegfilgrastim 6 mg s.c. day every 2 weeks. Patients included females with histologically confirmed locally advanced/inflammatory adenocarcinoma of the breast.

48 patients with a median age of 48 years (range 29-73) were enrolled. Tumor characteristics included 79% with ductal histology, 8% with lobular histology and 13% with inflammatory histology. Hormone receptor status included i) estrogen receptor (ER) negative and progesterone receptor (PgR) negative tumors-54% of patients; ii) ER+PgR+ tumors-33% of patients; iii) ER+PR-tumors-10% of patients; and iv) ER-PR+ tumors-2% of patients. HER2 status was shown to be HER2+ tumors-81% of patients and HER2-tumors-19% of patients. 113 cycles have been administered. 18 patients have completed the post-op therapy. Hemotologic toxicity primarily consisted of G3/4 neutropenia, 4 patients (8%); G3 thrombocytopenia, 3 patients (6%); and G3 anemia, 1 patient (2%). There were no episodes of febrile neutropenia. Non-hematologic toxicity was minimal with only 1 G4 event (fatigue) G3 events primarily consisted of arthralgia/pain, 5 patients (10%); neuropathy and infection each were noted in 2 patients.

35 patients were available to evaluate for pathological findings and combination drug therapy efficacy. Pathologic complete response (pCR; defined as pathologic complete responses in both the primary breast and lymph node tissue) was 20% (7/35); pathologic partial response was 74% (26.35); and stable disease was 6% (2/35).

The results demonstrated that dense combination therapy at neoadjuvant doses with gemcitabine, epirubicin and Abraxane® (GEA) was feasible and well-tolerated. Toxicity with the biweekly schedule was minimal and easily manageable. GEA combination therapy demonstrated high levels of complete or partial response rates.

Example 16

Abraxane® (ABI-007) Reduces Tumor Growth in MDA-MB-231 Human Tumor Xenografts and Induces Necrosis, Hypoxia and VEGF-A Expression MDA-MB-231 human breast cancer xenografts were orthotopically implanted in the mammary fat pads of female nude (nu/nu) mice. When the average tumor volume was 230 mm$^3$, mice were randomized into groups of five animals and treated with saline, Taxol®, Abraxane® or doxorubicin. Taxol® was administered at 10 mg/kg/day, Abraxane® was administered at 15 mg/kg/day, and doxorubicin was administered at 10 mg/kg/day. All drugs and control saline were administered i.v. in a volume of 100 µl daily for 5 days. Mice were sacrificed, tumors were harvested and tumor cellular extracts were prepared. VEGF-A protein levels in tumor extracts were determined by ELISA. In some cases, tumors from mice treated with Abraxane® were analyzed by histology.

TABLE 5

| Treatment | Dose Schedule | Mean Tumor Volume (mm$^3$) | % TGI | VEGF-A (pg/mg protein) |
|---|---|---|---|---|
| Saline control | 100 µl qdx5 | 523 ± 79 | | 337 ± 51 |
| Taxol ® | 10 mg/kg/day qdx5 | 231 ± 32 | 56 | 664 ± 66 |
| Abraxane ® | 15 mg/kg/day qdx5 | 187 ± 29 | 64 | 890 ± 82 |
| Doxorubicin | 10 mg/kg/day qdx5 | 287 ± 56 | 45 | 754 ± 49 |

As shown in Table 5, Taxol®, Abraxane® and doxorubicin all inhibited tumor growth as represented by a reduction in tumor volume when compared to saline-treated control animals. Tumor growth inhibition (TGI) was calculated by comparing mean tumor volume of test groups to that of the control group at the last measurement of the control group. Tumor growth inhibition was greatest in mice treated with Abraxane® (64% inhibition). Taxol® and doxorubicin showed tumor growth inhibition of 56% and 45%, respectively.

Levels of VEGF-A protein in tumor cellular extracts were measured by ELISA and shown to be increased in tumors from mice treated with Taxol®, Abraxane® and doxorubicin. VEGF-A protein levels were highest in tumors from mice treated with Abraxane® (164% increase), followed by doxorubicin (124%) and Taxol® (97%).

Tumors were harvested from saline-treated control mice and Abraxane®-treated mice one week after the last injection of Abraxane®. The tumors were evaluated for sites of necrosis and for the presence of hypoxic cells. Hypoxic cells were identified by immunohistochemical detection of pimonidazole-protein conjugates. As shown in FIG. 7 FIGS. 7A-7D, inhibition of tumor growth in Abraxane®-treated mice was accompanied by necrosis (FIG. 7B) and hypoxia (FIG. 7D) in the tumor tissue. Necrosis and hypoxia was not observed in tumor tissue from saline-treated control mice (FIG. 7A and FIG. 7C).

Example 17

VEGF-A and Avastin® Effects on Abraxane®-Induced in Vitro Cytotoxicity

The effect of VEGF-A or an anti-VEGF antibody (Avastin®) on Abraxane®-induced cytotoxicity was assessed in an in vitro cellular cytotoxicity assay. Cells were treated with Abraxane® in a range of concentrations (1 to 24 nM). Cells were also treated with VEGF-A or Avastin® and cytotoxicity was compared to cells treated with Abraxane® alone. As shown in FIG. 8A, addition of VEGF-A reduced the in vitro cytotoxicity of Abraxane®. In contrast, the addition of Avastin® increased the in vitro cytotoxicity of Abraxane® (FIG. 8A).

Similar results were observed in an in vitro clonogenic assay. Cells were treated with saline control, Abraxane® alone, VEGF-A alone, Avastin® alone, Abraxane®+ VEGF-A or Abraxane®+Avastin®. As shown in FIG. 8B, Abraxane® reduced the mean number of colonies formed as compared to saline control. Treatment with VEGF-2 alone increased the number of colonies formed, while treatment with Avastin® alone resulted in a slight reduction in the number of colonies formed. The addition of VEGF-A to Abraxane®-treated cells reduced the cytotoxic effect which resulted in a higher number of colonies formed as compared to Abraxane® alone. The addition of Avastin® to Abraxane®-treated cells appeared to have a synergistic effect demonstrating an increase in cytotoxicity (as demonstrated by a sharp decrease in number of colonies formed) over the level observed with Abraxane® or Avastin® alone.

Example 18

Abraxane® (ABI-007) in Combination with Avastin® Reduces Tumor Growth in MDA-MB-231 Tumor Xenografts Luciferase-expressing MDA-MB-231 human breast cancer xenografts were orthotopically implanted in the mammary fat pads of female nude (nu/nu) mice. When the average tumor volume reached 230 mm$^3$, mice were randomized into groups of five animals and treated with saline, Abraxane®, Avastin®, or a combination of Abraxane® plus Avastin®. Abraxane®, either alone or in combination, was administered at 10 mg/kg/day daily for 5 days in two cycles separated by 1 week. Some groups were administered Abraxane® at 10 mg/kg daily for 5 days for only one cycle. Avastin® was administered following the two cycles of Abraxane® at dosages of 2 mg/kg, 4 mg/kg or 8 mg/kg twice a week for 6 weeks. Avastin® alone was administered at a dosage of 4 mg/kg at the same time as mice in combination therapy. Mice were monitored for tumor growth and drug toxicity. Mice were sacrificed when the mean tumor volume in the saline-treated control group reached 2000 mm$^3$.

TABLE 6

| Treatment | Avastin® Dose | Mean Tumor Volume (mm$^3$) | % TGI | % Complete Regression[3] |
|---|---|---|---|---|
| Saline control | | 2391 ± 432 | | 0 |
| Abraxane® (ABX) | | 117 ± 38 | 95.11 | 0 |
| Avastin® | 4 mg/kg | 2089 ± 251 | 12.56 | 0 |
| ABX + Avastin® | 2 mg/kg | 138 ± 42 | 94.23 | 20 (1/5) |
| ABX + Avastin® | 4 mg/kg | 60 ± 17 | 97.49 | 40 (2/5) |
| ABX + Avastin® | 8 mg/kg | 36 ± 16 | 98.49 | 40 (2/5) |

No toxicity was observed in any treatment group. Tumor growth inhibition (TGI) was calculated by comparing mean tumor volume of test groups to that of the control group at the last measurement of the control group. As shown in Table 6 and in FIG. 9, Avastin® at a dose of 4 mg/kg did not significantly inhibit growth of primary tumors (12.56% inhibition). Abraxane® and Avastin® combination therapy, particularly with 2 cycles of Abraxane®, yielded a significantly better outcome than Avastin® alone, with tumor inhibition ranging from 94.23% to 98.49%. Abraxane® in combination with Avastin® at the two highest doses, yielded a better outcome that Abraxane® alone (97.49 or 98.49% compared to 95.11% inhibition). Abraxane® and Avastin® in combination resulted in regression of tumors in treated mice wherein complete regression referred to mice with no measurable tumors at day 65. Five of fifteen (30%) mice treated with a combination of Abraxane® and Avastin® showed complete tumor regression; tumors in the remaining mice were reduced by 90% compared with controls.

At these doses, Avastin® alone did not significantly inhibit primary tumors. The efficacy of Abraxane® was much higher than that of Avastin® and was substantially improved by adding a second cycle of Abraxane®. Only the combination of Abraxane® and Avastin® eradicated primary tumors in 30% of the mice.

Example 19

Abraxane® (ABI-007) in Combination with Avastin® Reduces Tumor Metastasis in MDA-MB-231 Tumor Xenografts As described in Example 25, luciferase-expressing MDA-MB-231 human breast cancer xenografts were orthotopically implanted in the mammary fat pads of female nude (nu/nu) mice. When the average tumor volume reached 230 mm$^3$, mice were randomized into groups and treated with saline (n=10), Abraxane® (n=5), Avastin® (n=5), or a combination of Abraxane® plus Avastin® (n=5). Abraxane®, either alone or in combination, was administered at 10 mg/kg/day daily for 5 days in two cycles separated by 1 week. Some groups were administered Abraxane® at 10 mg/kg daily for 5 days for only one cycle. Avastin® was administered following the two cycles of Abraxane® at dosages of 2 mg/kg, 4 mg/kg or 8 mg/kg twice a week for 6 weeks. Avastin® alone was administered at a dosage of 4 mg/kg at the same time as mice in combination therapy. Mice were sacrificed when the mean tumor volume in the saline-treated control group reached 2000 mm$^3$. Axillary lymph nodes and both lobes of the lungs were removed from each mouse and cellular extracts were prepared. The presence of MDA-MB-231 cells in these tissues was evaluated by analysis of luciferase activity and was an indicator of metastasis from the primary tumor. Luciferase activity was measured in extracts from 10 lymph nodes and both lobes of the lungs on the day of sacrifice (day 65 after tumor implantation). A value greater than 500 light units per 20 µl lysate was rated as positive for presence of MDA-MB-231 cells and for incidence of metastasis.

TABLE 7

| Treatment | Avastin ® Dose | Lymph Node Metastasis | | Pulmonary Metastasis | |
|---|---|---|---|---|---|
| | | Incidence | P Value | Incidence | P Value |
| Saline control | | 10/10 (100%) | | 7/10 (70%) | |
| Abraxane ® (ABX) | | 5/5 (100%) | — | 4/5 (80%) | — |
| Avastin ® | 4 mg/kg | 5/5 (100%) | — | 3/5 (60%) | NS |
| ABX + Avastin ® | 2 mg/kg | 5/5 (100%) | — | 1/5 (20%) | 0.045 |
| ABX + Avastin ® | 4 mg/kg | 2/5 (40%) | 0.022 | 2/5 (40%) | NS |
| ABX + Avastin ® | 8 mg/kg | 2/5 (40%) | 0.022 | 0/5 (0%) | 0.025 |

As shown in Table 7, treatment with Abraxane® or Avastin® alone appeared to have no effect on the incidence of tumor metastasis to the lymph nodes as analyzed by luciferase activity in cellular extracts. As used herein, incidence refers to the presence of luciferase activity in tissue from each mouse. Abraxane® in combination with Avastin® did demonstrate a significant effect on tumor metastasis, particularly with 2 cycles of Abraxane®. Incidence of metastases fell to 40% in groups treated with Abraxane® and Avastin® at the two highest dosages of 4 mg/kg and 8 mg/kg. (P value=0.022; wherein the P value was generated by the analysis of difference between test and control groups with Fisher's exact test; NS refers to non-significant.) Abraxane® or Avastin® alone appeared to have little effect on incidence of tumor metastasis to the lungs as shown in Table 6. Abraxane® in combination with Avastin® demonstrated an effect on the incidence of lung metastases. Incidence of metastases fell to 20%, 40% and 0% with combinations of Abraxane® and Avastin® at dosages of 2 mg/kg, 4 mg/kg and 8 mg/kg, respectively.

Tumor metastasis to the lymph nodes and lungs as evaluated by luciferase activity in tissue extracts is shown in FIGS. 10A and 10B. The combination of Abraxane® and Avastin® had a synergistic effect on reducing lymph node metastases (FIG. 10A) and lung metastases (FIG. 10B) of the MDA-MB-231 tumor cells. At these doses, Avastin® alone did not significantly inhibit metastasis. The efficacy of Abraxane® was much higher than that of Avastin® and was substantially improved by adding a second cycle of Abraxane®. Only the combination of Abraxane® and Avastin® eliminated regional and distant metastases in a proportion of the treated mice.

Example 20

Abraxane® (ABI-007) in Combination with Avastin® for Treatment of Metastatic Breast Cancer The combination of bevacizumab (Avastin®) and paclitaxel has significant activity in metastatic breast cancer. Abraxane® is less toxic and has demonstrated a better tumor delivery than paclitaxel, therefore the combination of Abraxane® and Avastin® was used to treat women with metastatic breast cancer.

27 women with metastatic breast cancer were treated with a combination of Abraxane® and Avastin®. Abraxane® was administered at 80-125 mg/m$^2$ on day 1, 8 and 15 (once a week for 3 weeks) or 170-200 mg/m$^2$ every 14 days (once every 2 weeks) on a 28 day cycle, Avastin® was administered at 10 mg/m$^2$ every 14 days (once every 2 weeks). A minimum of two cycles (2 months) was given to each patient. All of the women had previously received a minimum of three chemotherapy regimens including anthracyclines (26/27) and taxanes (24/27). The patients were monitored for response to treatment using physical exams, tumor markers, and PET/CT fusion scanning. All patients were consistently monitored for any clinical signs of toxicity or adverse effects.

Three patients had complete responses (11%), 13 patients had partial responses (48%), resulting in an overall response rate of 59%. Seven patents had stable disease and four patients progressed. Overall toxicity was acceptable, however 6 patients had side effects with one patient being withdrawn from the treatment.

The combination of Abraxane® and Avastin® was very active in a population of heavily pre-treated women with metastatic breast cancer. The results demonstrated an objective clinical response rate of 59% (3 complete response and 13 partial response).

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

All references, including publications, patent applications, and patents, cited herein are hereby incorporated by reference to the same extent as if each reference were individually and specifically indicated to be incorporated by reference and were set forth in its entirety herein.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for treating breast cancer in an individual, the method comprising:
    (a) determining hormone receptor status of estrogen receptor and progesterone receptor;
    (b) administering to the individual an effective amount of a composition comprising nanoparticles comprising paclitaxel and an albumin, and
    (c) administering to the individual an effective amount of epirubicin and cyclophosphamide,
wherein the hormone receptor status of the individual is negative for both estrogen receptor and progesterone receptor.

2. The method of claim 1, wherein the average diameter of the nanoparticles in the composition is no greater than about 200 nm.

3. The method of claim 1, wherein the albumin is human serum albumin.

4. The method of claim 1, wherein the weight ratio of the albumin and the paclitaxel in the nanoparticle composition is about 9:1 or less.

5. The method of claim 1, wherein the individual is human.

6. The method of claim 1, wherein the hormone receptor status of estrogen receptor and progesterone receptor is determined by immunohistochemistry.

7. The method of claim 1, wherein the breast cancer expresses HER2 (HER2+).

8. The method of claim 1, wherein the dosage of paclitaxel in the nanoparticle composition is 50-300 mg/m$^2$.

9. The method of claim 1, wherein the method is for treatment of breast cancer in a neoadjuvant setting.

10. The method of claim 1, wherein the dosage of paclitaxel in the nanoparticle composition is 125 mg/m$^2$.

11. The method of claim 1, wherein the average diameter of the nanoparticles in the composition is no greater than about 150 nm.

12. The method of claim 1, wherein the average diameter of the nanoparticles in the composition is about 130 nm.

13. The method of claim 1, wherein the paclitaxel is coated with albumin.

14. The method of claim 2, wherein the weight ratio of the albumin and the paclitaxel in the nanoparticle composition is about 9:1 or less, wherein the paclitaxel is coated with albumin.

15. The method of claim 2, wherein the method is for treatment of breast cancer in a neoadjuvant setting.

16. The method of claim 2, wherein the dosage of paclitaxel in the nanoparticle composition is 50-300 mg/m$^2$.

17. The method of claim 14, wherein the dosage of paclitaxel in the nanoparticle composition is 50-300 mg/m$^2$.

18. The method of claim 11, wherein the weight ratio of the albumin and the paclitaxel in the nanoparticle composition is about 9:1 or less, wherein the paclitaxel is coated with albumin.

19. The method of claim 12, wherein the weight ratio of the albumin and the paclitaxel in the nanoparticle composition is about 9:1 or less, wherein the paclitaxel is coated with albumin.

* * * * *